United States Patent
Cho et al.

(10) Patent No.: US 10,835,130 B2
(45) Date of Patent: Nov. 17, 2020

(54) NONINVASIVE BLOOD GLUCOSE MEASUREMENT METHOD AND APPARATUS

(71) Applicant: Samsung Electronics Co., Ltd., Suwon-si (KR)

(72) Inventors: Chul-ho Cho, Yongin-si (KR); Kwang-bok Kim, Incheon (KR); Seong-je Cho, Suwon-si (KR); Seung-min Lee, Seoul (KR); Jeong-gun Lee, Seoul (KR); Sun-tae Jung, Yongin-si (KR); Jae-geol Cho, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 772 days.

(21) Appl. No.: 14/977,032

(22) Filed: Dec. 21, 2015

(65) Prior Publication Data

US 2016/0174853 A1    Jun. 23, 2016

(30) Foreign Application Priority Data

Dec. 19, 2014   (KR) ........................ 10-2014-0184966

(51) Int. Cl.
*A61B 5/0205*       (2006.01)
*A61B 5/00*         (2006.01)
(Continued)

(52) U.S. Cl.
CPC ........ *A61B 5/02055* (2013.01); *A61B 5/0002* (2013.01); *A61B 5/0024* (2013.01);
(Continued)

(58) Field of Classification Search
CPC . A61B 5/02055; A61B 5/4261; A61B 5/0205; A61B 5/0024; A61B 5/7278;
(Continued)

(56) References Cited

U.S. PATENT DOCUMENTS 5,703,364 A    12/1997   Rosenthal
5,725,480 A    3/1998    Oosta et al.
(Continued)

FOREIGN PATENT DOCUMENTS

CN    1732841 A      2/2006
CN    101005798 A    7/2007
(Continued)

OTHER PUBLICATIONS

International Search Report dated Mar. 28, 2016 corresponding to International Patent Application No. PCT/KR2015/013724.
(Continued)

*Primary Examiner* — Jacqueline Cheng
*Assistant Examiner* — Tho Q Tran
(74) *Attorney, Agent, or Firm* — Nixon & Vanderhye P.C.

(57) ABSTRACT

A blood glucose measurement apparatus includes: a control unit configured to determine a user's blood glucose level based on a concentration of body fluid secreted from the user; and a biometric information acquisition unit configured to acquire biometric information indicating a status of a user's autonomic nervous system. The control unit is configured to correct the determined blood glucose level based on the biometric information.

16 Claims, 53 Drawing Sheets

(51) Int. Cl.
*A61B 5/024* (2006.01)
*A61B 5/01* (2006.01)
*A61B 5/02* (2006.01)
*A61B 5/08* (2006.01)
*A61B 5/11* (2006.01)
*A61B 5/145* (2006.01)
*A61B 10/00* (2006.01)
*A61B 5/053* (2006.01)
*A61B 3/10* (2006.01)
*A61B 3/11* (2006.01)

(52) U.S. Cl.
CPC ........ *A61B 5/0205* (2013.01); *A61B 5/14532* (2013.01); *A61B 5/4035* (2013.01); *A61B 5/4261* (2013.01); *A61B 5/4266* (2013.01); *A61B 5/4277* (2013.01); *A61B 5/443* (2013.01); *A61B 5/7278* (2013.01); *A61B 10/007* (2013.01); *A61B 10/0051* (2013.01); *A61B 10/0064* (2013.01); *A61B 3/101* (2013.01); *A61B 3/112* (2013.01); *A61B 5/01* (2013.01); *A61B 5/024* (2013.01); *A61B 5/02007* (2013.01); *A61B 5/02416* (2013.01); *A61B 5/0533* (2013.01); *A61B 5/082* (2013.01); *A61B 5/112* (2013.01); *A61B 2010/0067* (2013.01)

(58) Field of Classification Search
CPC ............ A61B 10/0051; A61B 10/0064; A61B 5/14532; A61B 10/007; A61B 5/4035; A61B 5/4266; A61B 5/4277; A61B 5/0002; A61B 5/443
See application file for complete search history.

(56) References Cited

U.S. PATENT DOCUMENTS

| | | |
|---|---|---|
| 5,795,305 A | 8/1998 | Cho et al. |
| 5,890,489 A | 4/1999 | Elden |
| 5,924,996 A | 7/1999 | Cho et al. |
| 5,945,676 A | 8/1999 | Khalil et al. |
| 5,961,449 A | 10/1999 | Toida et al. |
| 6,016,435 A | 1/2000 | Maruo et al. |
| 6,044,285 A | 3/2000 | Chaiken et al. |
| 6,064,898 A | 5/2000 | Aldrich |
| 6,066,847 A | 5/2000 | Rosenthal |
| 6,067,463 A | 5/2000 | Jeng et al. |
| 6,175,752 B1 | 1/2001 | Say et al. |
| 6,236,047 B1 | 5/2001 | Malin et al. |
| 6,312,393 B1 | 11/2001 | Abreu |
| 6,400,972 B1 | 6/2002 | Fine |
| 6,405,069 B1 | 6/2002 | Oraevsky et al. |
| 6,424,850 B1 | 7/2002 | Lambert et al. |
| 6,441,388 B1 | 8/2002 | Thomas et al. |
| 6,477,392 B1 | 11/2002 | Honigs et al. |
| 6,477,394 B2 | 11/2002 | Rice et al. |
| 6,487,429 B2 | 11/2002 | Hockersmith et al. |
| 6,528,809 B1 | 3/2003 | Thomas et al. |
| 6,587,704 B1 | 7/2003 | Fine et al. |
| 6,640,116 B2 | 10/2003 | Diab |
| 6,640,117 B2 | 10/2003 | Makarewicz et al. |
| 6,788,965 B2 | 9/2004 | Ruchti et al. |
| 6,816,742 B2 | 11/2004 | Kim et al. |
| 6,876,931 B2 | 4/2005 | Lorenz et al. |
| 6,954,661 B2 | 10/2005 | Cho et al. |
| 6,954,662 B2 | 10/2005 | Freger et al. |
| 6,990,364 B2 | 1/2006 | Ruchti et al. |
| 6,993,372 B2 | 1/2006 | Fin et al. |
| 6,998,247 B2 | 2/2006 | Monfre et al. |
| 7,020,506 B2 | 3/2006 | Fin et al. |
| 7,039,446 B2 | 5/2006 | Ruchti et al. |
| 7,043,289 B2 | 5/2006 | Fin et al. |
| 7,098,037 B2 | 8/2006 | Haas et al. |
| 7,120,478 B2 | 10/2006 | Cho et al. |
| 7,133,710 B2 | 11/2006 | Acosta et al. |
| 7,215,983 B2 | 5/2007 | Cho et al. |
| 7,251,514 B2 | 7/2007 | Cho et al. |
| 7,251,515 B2 | 7/2007 | Cho et al. |
| 7,251,517 B2 | 7/2007 | Cho et al. |
| 7,254,426 B2 | 8/2007 | Cho et al. |
| 7,254,428 B2 | 8/2007 | Cho et al. |
| 7,254,429 B2 | 8/2007 | Shurman et al. |
| 7,254,430 B2 | 8/2007 | Cho et al. |
| 7,254,432 B2 | 8/2007 | Fine |
| 7,266,400 B2 | 9/2007 | Fine et al. |
| 7,317,938 B2 | 1/2008 | Lorenz et al. |
| 7,317,939 B2 | 1/2008 | Fine et al. |
| RE40,316 E | 5/2008 | Gobeli et al. |
| 7,386,336 B2 | 6/2008 | Fine et al. |
| 7,438,855 B2 | 10/2008 | Sota et al. |
| 7,509,153 B2 | 3/2009 | Blank et al. |
| 7,526,329 B2 | 4/2009 | Hogan et al. |
| 7,623,988 B2 | 11/2009 | Bedard et al. |
| 7,664,605 B2 | 2/2010 | Chaiken et al. |
| 7,698,105 B2 | 4/2010 | Ruchti et al. |
| 7,729,734 B2 | 6/2010 | Mandelis et al. |
| 7,809,416 B2 | 10/2010 | Ota et al. |
| 7,822,452 B2 | 10/2010 | Schurman et al. |
| 7,933,005 B2 | 4/2011 | MacIntyre et al. |
| 8,036,727 B2 | 10/2011 | Schurman et al. |
| 8,135,450 B2 | 3/2012 | Esenaliev et al. |
| 8,140,139 B2 | 3/2012 | Grata et al. |
| 8,306,593 B2 | 11/2012 | Hwang et al. |
| 8,452,360 B2 | 5/2013 | Mandelis et al. |
| 8,515,509 B2 | 8/2013 | Bruinsma et al. |
| 8,523,785 B2 | 9/2013 | Kaushal et al. |
| 8,570,503 B2 | 10/2013 | Vo et al. |
| 8,577,432 B2 | 11/2013 | Hogan et al. |
| 8,597,208 B2 | 12/2013 | MacIntyre et al. |
| 8,684,900 B2 | 4/2014 | Tran |
| 8,805,465 B2 | 8/2014 | Hodge et al. |
| 9,060,700 B2 | 6/2015 | Cho et al. |
| 9,827,389 B2 | 11/2017 | Farrugia |
| 2001/0023324 A1 | 9/2001 | Pronovost et al. |
| 2004/0106163 A1 | 6/2004 | Workman, Jr. et al. |
| 2005/0038674 A1* | 2/2005 | Braig ............... G06F 19/3418 705/2 |
| 2005/0043630 A1 | 2/2005 | Buchert |
| 2005/0101847 A1 | 5/2005 | Routt et al. |
| 2005/0187442 A1 | 8/2005 | Cho et al. |
| 2005/0192492 A1 | 9/2005 | Cho et al. |
| 2005/0250999 A1 | 11/2005 | Cho et al. |
| 2006/0004271 A1* | 1/2006 | Peyser ............... A61B 5/14521 600/362 |
| 2006/0029991 A1 | 2/2006 | Hagino et al. |
| 2006/0063986 A1 | 3/2006 | Hogan |
| 2006/0079742 A1 | 4/2006 | Cho et al. |
| 2006/0084853 A1 | 4/2006 | Cho et al. |
| 2006/0084854 A1 | 4/2006 | Cho et al. |
| 2006/0116562 A1 | 6/2006 | Acosta et al. |
| 2006/0167350 A1 | 7/2006 | Monfre et al. |
| 2006/0173255 A1 | 8/2006 | Acosta et al. |
| 2006/0183983 A1 | 8/2006 | Acosta et al. |
| 2006/0211927 A1 | 9/2006 | Acosta et al. |
| 2006/0226991 A1 | 10/2006 | Rivas |
| 2006/0281982 A1 | 12/2006 | Grata et al. |
| 2007/0078312 A1 | 4/2007 | Fine et al. |
| 2008/0045825 A1* | 2/2008 | Melker ............... A61B 5/083 600/365 |
| 2008/0117416 A1 | 5/2008 | Hunter et al. |
| 2008/0200783 A9 | 8/2008 | Blank et al. |
| 2008/0218696 A1 | 9/2008 | Mir |
| 2008/0249393 A1 | 10/2008 | Finarov et al. |
| 2009/0221886 A1 | 9/2009 | Kaushal et al. |
| 2009/0270700 A1 | 10/2009 | Van Herpen et al. |
| 2009/0290161 A1* | 11/2009 | Atkin ................. G01N 21/00 356/433 |
| 2010/0004517 A1 | 1/2010 | Bryenton et al. |
| 2010/0030040 A1 | 2/2010 | Poeze et al. |
| 2010/0036221 A1 | 2/2010 | Lee et al. |
| 2010/0160750 A1 | 6/2010 | White et al. |
| 2010/0234712 A1 | 9/2010 | Sugenoya et al. |

(56) References Cited

U.S. PATENT DOCUMENTS

| | | |
|---|---|---|
| 2010/0324398 A1 | 12/2010 | Tzyy-Ping |
| 2011/0028806 A1 | 2/2011 | Merritt et al. |
| 2011/0230744 A1 | 9/2011 | Ribas Ripoll et al. |
| 2012/0059237 A1 | 3/2012 | Amir et al. |
| 2012/0095303 A1 | 4/2012 | He |
| 2012/0166092 A1 | 6/2012 | Maruo |
| 2012/0172686 A1 | 7/2012 | Esenaliev et al. |
| 2012/0277557 A1 | 11/2012 | Li et al. |
| 2013/0006072 A1 | 1/2013 | Xu |
| 2013/0102018 A1* | 4/2013 | Schentag ............... G01N 21/17 435/25 |
| 2013/0217979 A1 | 8/2013 | Blackadar et al. |
| 2013/0268204 A1 | 10/2013 | Maier |
| 2014/0058218 A1 | 2/2014 | Randlov et al. |
| 2014/0120564 A1 | 5/2014 | Workman et al. |
| 2014/0148658 A1 | 5/2014 | Zalevsky et al. |

FOREIGN PATENT DOCUMENTS

| | | | |
|---|---|---|---|
| CN | 101194838 A | 6/2008 | |
| CN | 101854858 A | 10/2010 | |
| CN | 102014998 A | 4/2011 | |
| CN | 102323310 A | 1/2012 | |
| KR | 10-2009-0098800 | 9/2009 | |
| KR | 20090118314 A * | 11/2009 | ......... A61B 5/14532 |
| KR | 10-2012-0043189 A | 5/2012 | |
| WO | WO2007/051796 | 5/2007 | |
| WO | WO 2009/139522 | 11/2009 | |

OTHER PUBLICATIONS

Kundu, Samar K. et al., Breath Acetone Analyzer: Diagnostic Tool to Monitor Dietary Fat Loss, Clin. Chem. 39/1, 87-92 (1993).

Task Force of the European Society of Cardiology and the North American Society of Pacing andElectrophysiology, Heart Rate Variability, European Heart Journal (1996).

Chowdhury, Md Koushik et al., Challenges & Countermeasures in Optical Noninvasive Blood Glucose Detection, International Journal of Innovative Research in Science, Engineering and Technology, vol. 2, Issue 1, Jan. 2013.

Lee, Hyo Eun, MD, et al., Hyperhidrosis and Hypohidrosis, Journal of Pain and Autonomic Disorders, Jun. 2013.

Smith, John L., The Pursuit of Noninvasive Glucose: "Hunting the Deceitful Turkey," 2013.

Office Action for CN Application No. 201580068798.6 dated Oct. 26, 2018.

Chinese Office Action dated Jul. 2, 2019 for CN Application No. 201580068798.6.

Chinese Office Action dated Jan. 13, 2020 for CN Application No. 201580068798.6.

* cited by examiner

| EFFECTOR ORGAN | UPON ACTIVATION OF SYMPATHETIC NERVE | UPON ACTIVATION OF PARASYMPATHETIC NERVE |
|---|---|---|
| TEAR | – | SECRETION ACCELERATION |
| SWEAT | SECRETION ACCELERATION | – |
| SALIVA | SECRETION DECREASE | SECRETION INCREASE |

FIG. 7A

| EFFECTOR ORGAN | | UPON ACTIVATION OF SYMPATHETIC NERVE | UPON ACTIVATION OF PARASYMPATHETIC NERVE |
|---|---|---|---|
| EYE | IRIS | PUPIL EXPANSION | PUPIL CONTRACTION |
| | CILIARY MUSCLE | RELAXATION | CONTRACTION |
| HEART | HEART RATE | INCREASE | DECREASE |
| | HEART CONDUCTIVITY | INCREASE | DECREASE |
| BLOOD VESSEL | | CONTRACTION | – |

| 925 — STATUS OF AUTONOMIC NERVOUS SYSTEM | 930 — SWEAT SECRETION VELOCITY (mg/cm2/min) |
|---|---|
| -2.5 | 0.3 |
| -1.1 | 0.3 |
| 0 | 0.3 |
| 1.0 | 1.1 |
| 1.6 | 1.4 |
| 2.5 | 2.6 |

| 925 — STATUS OF AUTONOMIC NERVOUS SYSTEM | 940 — SALIVA SECRETION VELOCITY (ml/min) |
|---|---|
| 3.2 | 0.1 |
| 1.6 | 0.2 |
| 0 | 0.3 |
| -1.1 | 0.4 |
| -2.3 | 0.5 |
| -3.6 | 0.6 |

| 925 — STATUS OF AUTONOMIC NERVOUS SYSTEM | 950 — TEAR SECRETION VELOCITY (μl/min) |
|---|---|
| 2.3 | 1.2 |
| 1.0 | 1.2 |
| 0 | 1.2 |
| -2.5 | 2.4 |
| -3.3 | 3.1 |
| -4.0 | 3.4 |

NONINVASIVE BLOOD GLUCOSE MEASUREMENT METHOD AND APPARATUS

RELATED APPLICATION

This application claims the benefit of Korean Patent Application No. 10-2014-0184966, filed on Dec. 19, 2014, in the Korean Intellectual Property Office, the disclosure of which is incorporated herein in its entirety by reference.

BACKGROUND

The present disclosure relates to methods and apparatuses for measuring a user's blood glucose level by using a user's biometric data.

Diabetes is a disease in which an amount of glucose in a blood is excessively small or excessively large. The diabetes may be developed when insulin is not made or not sufficiently made in a pancreas. The insulin is a hormone that helps cells to produce energy by using glucose. In addition, the diabetes may be developed when the secreted insulin does not normally work in the cells and glucose is not normally absorbed into the cells.

A blood glucose level may be measured by collecting a blood sample and measuring a concentration of glucose in the collected blood sample. However, a user feels pain when a user's skin is stuck by a lancet, for example, during the collection of the blood sample.

Therefore, disclosed are a method of measuring a blood glucose level without collecting any blood sample, and a method capable of solving inaccurate measurement that may occur since a blood glucose level is not directly measured from a blood sample.

SUMMARY

Provided are methods and apparatuses for correcting a user's blood glucose level by using a user's biometric data.

Additional aspects will be set forth in part in the description which follows and, in part, will be apparent from the description, or may be learned by practice of the presented exemplary embodiments.

According to an aspect of an exemplary embodiment, a blood glucose measurement apparatus includes: a control unit configured to determine a user's blood glucose level based on a concentration of body fluid secreted from the user; and a biometric information acquisition unit configured to acquire biometric information indicating a status of a user's autonomic nervous system, wherein the control unit is configured to correct the determined blood glucose level based on the biometric information.

The control unit may be configured to determine the status of the autonomic nervous system based on the biometric information, determine a secretion velocity of the body fluid based on the determined status of the autonomic nervous system, and correct the determined blood glucose level based on the determined secretion velocity of the body fluid.

The body fluid may include at least one of a user's sweat, tear, saliva, and urine.

The status of the autonomic nervous system may include an activity degree of at least one of a user's sympathetic nerve and parasympathetic nerve.

The biometric information indicating the status of the autonomic nervous system may include at least one of a user's heart rate, a user's galvanic skin response, a contraction degree of a user's blood vessel, a size of a user's pupil, an amount of a user's sweat, an amount of a user's tear, an amount of a user's saliva, and a user's body temperature.

The biometric information acquisition unit may include a communication unit configured to receive the biometric information indicating the status of the user's autonomic nervous system from a sensor attached to the user.

According to an aspect of another exemplary embodiment, a blood glucose measurement apparatus includes: a control unit configured to determine a user's blood glucose level based on a concentration of biomarker gas in a user's expiration; and a biometric information acquisition unit configured to acquire biometric information indicating a user's motion quantity, wherein the control unit is configured to correct the determined blood glucose level based on the biometric information.

The biomarker gas may be a gas that is discharged through the user's expiration when a user's body fat is decomposed.

The biometric information indicating the user's motion quantity may include at least one of a user's step count, a user's moving speed, a user's heart rate, a users' skin hydration, and a user's body temperature.

The control unit may be configured to determine a user's motion quantity per unit time based on the biometric information and correct the determined blood glucose level based on the determined motion quantity per unit time.

According to an aspect of another exemplary embodiment, a blood glucose measurement method includes: determining a user's blood glucose level based on a concentration of body fluid secreted from the user; acquiring biometric information indicating a status of a user's autonomic nervous system; and correcting the determined blood glucose level based on the biometric information.

The correcting of the determined blood glucose level based on the biometric information may include: determining the status of the autonomic nervous system based on the biometric information; determining a secretion velocity of the body fluid based on the determined status of the autonomic nervous system; and correcting the determined blood glucose level based on the determined secretion velocity of the body fluid.

The acquiring of the biometric information indicating the status of the user's autonomic nervous system may include receiving the biometric information indicating the status of the user's autonomic nervous system from a sensor attached to the user.

According to an aspect of another exemplary embodiment, a blood glucose measurement method includes: determining a user's blood glucose level based on a concentration of biomarker gas in a user's expiration; acquiring biometric information indicating a user's motion quantity; and correcting the determined blood glucose level based on the biometric information.

The correcting of the determined blood glucose level based on the biometric information may include: determining the user's motion quantity per unit time based on the biometric information; and correcting the determined blood glucose level based on the determined motion quantity per unit time.

BRIEF DESCRIPTION OF THE DRAWINGS

These and/or other aspects will become apparent and more readily appreciated from the following description of the exemplary embodiments, taken in conjunction with the accompanying drawings in which:

FIGS. 7A to 7D are diagrams for describing a method by which a blood glucose measurement apparatus determines a secretion velocity of body fluid based on a status of a user's autonomic nervous system, according to an exemplary embodiment;

FIGS. 8A to 8D are diagrams for describing a method by which a blood glucose measurement apparatus determines a status of a user's autonomic nervous system based on a user's biometric information, according to an exemplary embodiment;

FIG. 10 is a diagram for describing a method by which a blood glucose measurement apparatus determines a secretion velocity of body fluid based on a status of a user's autonomic nervous system, according to another exemplary embodiment;

DETAILED DESCRIPTION

Figure 1:
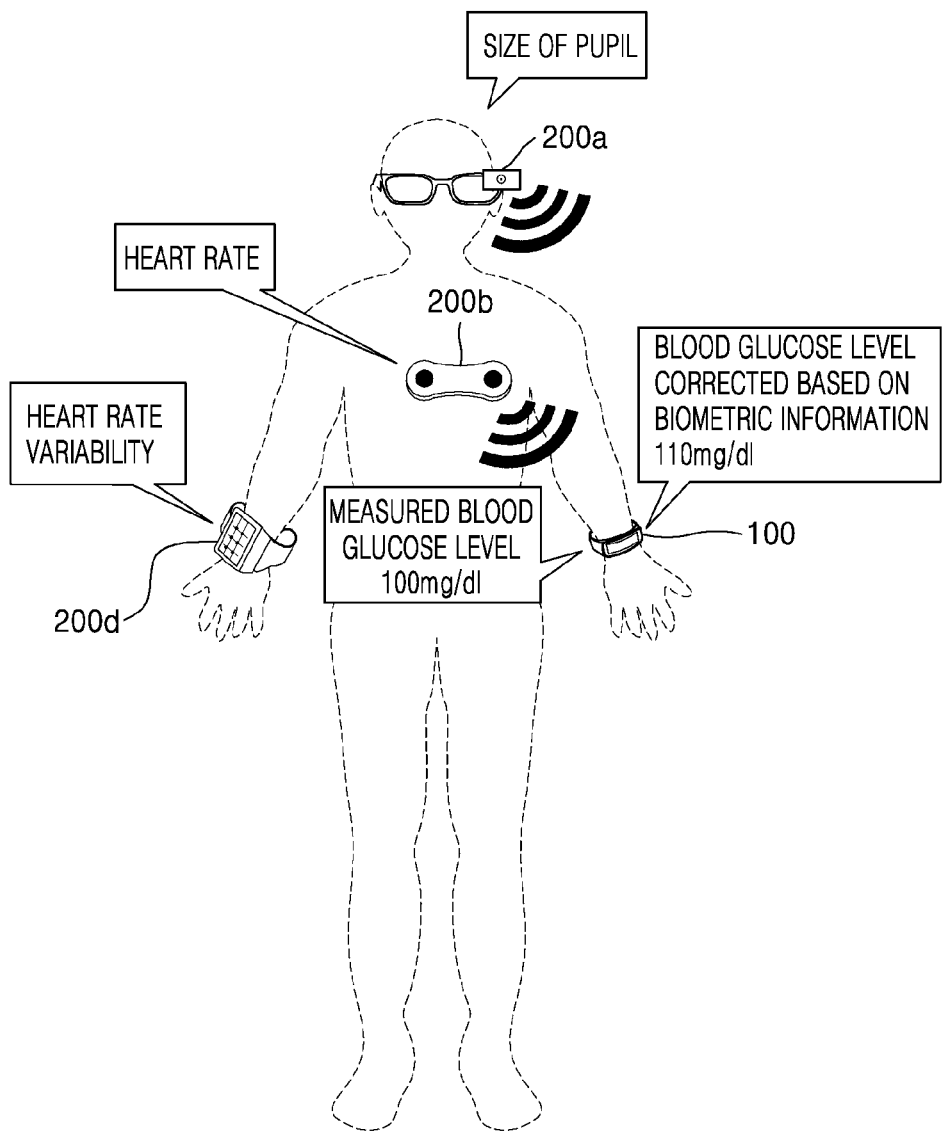
FIG. 1 is a diagram for describing a method by which a blood glucose measurement apparatus corrects a user's blood glucose level based on a user's biometric information, according to an exemplary embodiment.

The terms used in the present disclosure will be described briefly and exemplary embodiments will then be described in detail.

The terms used in the present disclosure are those general terms currently widely used in the art in consideration of functions in regard to the inventive concept, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the present disclosure should be understood not as simple names but based on the meaning of the terms and the overall description of the inventive concept.

It will also be understood that the terms "comprises", "includes", and "has", when used herein, specify the presence of stated elements, but do not preclude the presence or addition of other elements, unless otherwise defined. Also, the terms "unit" and "module" used herein represent a unit for processing at least one function or operation, which may be implemented by hardware, software, or a combination of hardware and software.

In this specification, the term "blood glucose level" may mean a concentration of glucose in a user's blood.

The exemplary embodiments will be described with reference to the accompanying drawings in such a manner that the exemplary embodiments may be easily carried out by a person of ordinary skill in the art. However, the inventive concept may be implemented in various forms and is not limited to the exemplary embodiments. In addition, descriptions of well-known functions and constructions will be omitted for clarity and conciseness, and similar reference numerals are assigned to similar elements throughout the specification.

FIG. 1 is a diagram for describing a method by which a blood glucose measurement apparatus 100 corrects a blood glucose level based on biometric information, according to an exemplary embodiment.

Referring to FIG. 1, the blood glucose measurement apparatus 100 may measure a user's blood glucose level. Also, the blood glucose measurement apparatus 100 may measure a user's blood glucose level by using a concentration of glucose in body fluid secreted from the user. In addition, the blood glucose measurement apparatus 100 may measure a user's blood glucose level by using a concentration of biomarker gas in a user's expiration. In a case where the user's blood glucose level is determined based on the concentration of glucose in the body fluid, the concentration of glucose may be changed due to a change in a secretion velocity of the body fluid even when the blood glucose level is constant.

In a case where the user's blood glucose level is determined based on the concentration of the biomarker gas in the user's expiration, the concentration of the biomarker gas in the user's expiration may be changed due to a change in a user's motion quantity per unit time even when the blood glucose level is constant.

The blood glucose measurement apparatus 100 may correct the measured blood glucose level based on acquired biometric information.

In a case where the user's blood glucose level is determined based on the concentration of glucose in the body fluid, the blood glucose measurement apparatus 100 may determine a secretion velocity of the body fluid based on the acquired biometric information and correct the measured blood glucose level based on the determined secretion velocity of the body fluid. The secretion velocity of the body fluid may be determined based on a status of a user's autonomic nervous system. In addition, the status of the user's autonomic nervous system may be determined based on the biometric information.

For example, the blood glucose measurement apparatus 100 may determine the user's blood glucose level based on a concentration of glucose in a user's sweat. In addition, the blood glucose measurement apparatus 100 may receive information about a size of a pupil from glasses 200a with a built-in camera. The blood glucose measurement apparatus 100 may determine an activated degree of a user's sympathetic nerve based on the received information about the size of the pupil. The blood glucose measurement apparatus 100 may determine a secretion velocity of the sweat based on the activated degree of the use's sympathetic nerve. When the secretion velocity of the sweat is high, the blood glucose measurement apparatus 100 may determine the user's blood glucose level to be higher than the measured blood glucose level.

In addition, In a case where the user's blood glucose level is determined based on the concentration of the biomarker gas in the user's expiration, the blood glucose measurement apparatus 100 may determine a user's motion quantity per unit time based on the acquired biometric information and correct the measured blood glucose level based on the measured motion quantity per unit time. The user's motion quantity may be determined based on the biometric information.

For example, the blood glucose measurement apparatus 100 may determine the user's blood glucose level based on the concentration of the biomarker gas in the user's expiration. In addition, the blood glucose measurement apparatus 100 may receive a user's heart rate data from an electrocardiogram (ECG) sensor 200b. The blood glucose measurement apparatus 100 may determine the user's motion quantity per unit time based on the received heart rate data. For example, the user's motion quantity per unit time may be highly determined in proportion to the heart rate. When the user's motion quantity per unit time is large, the blood glucose measurement apparatus 100 may determine the user's blood glucose level to be lower than the measured blood glucose level.

The blood glucose measurement apparatus 100 may measure a user's biometric information by using a sensor provided therein. In addition, the blood glucose measurement apparatus 100 may receive the user's biometric information from a sensor attached to the user.

Examples of the sensor may include the glasses 200*a* with a built-in camera, the ECG sensor 200*b*, a photoplethysmogram (PPG) sensor 220*d*, a galvanic skin response sensor 200*c*, and a thermometer 200*e*, but are not limited thereto.

Figure 2A:
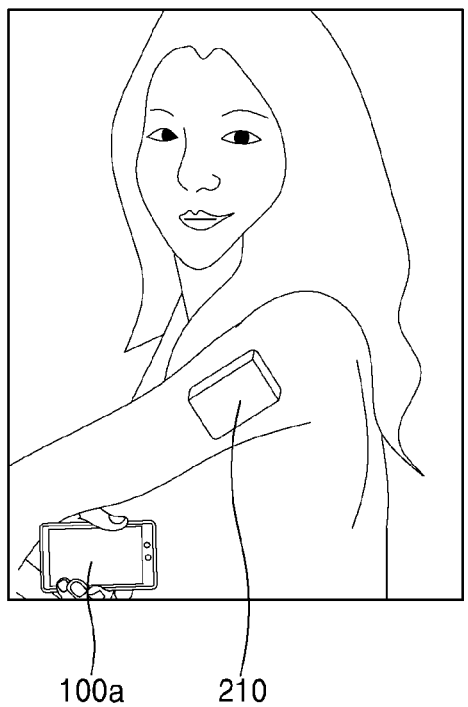
FIGS. 2A to 2E are diagrams for describing a method by which a blood glucose measurement apparatus determines a user's blood glucose level based on a concentration of glucose in a user's sweat, according to an exemplary embodiment.
Figure 2B:
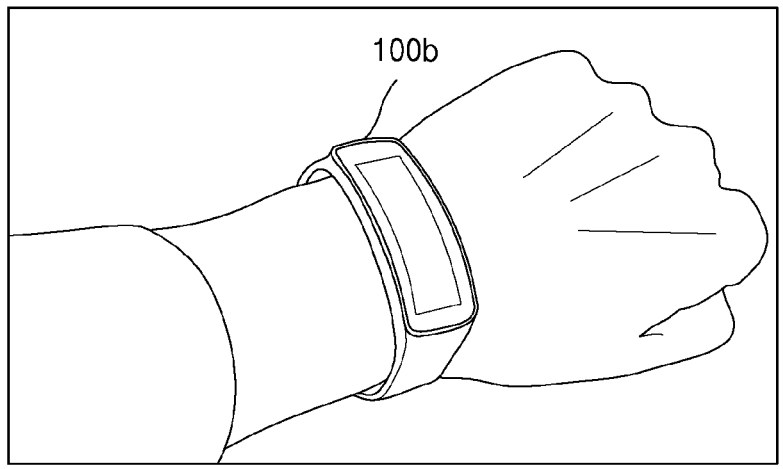
Figure 2C:
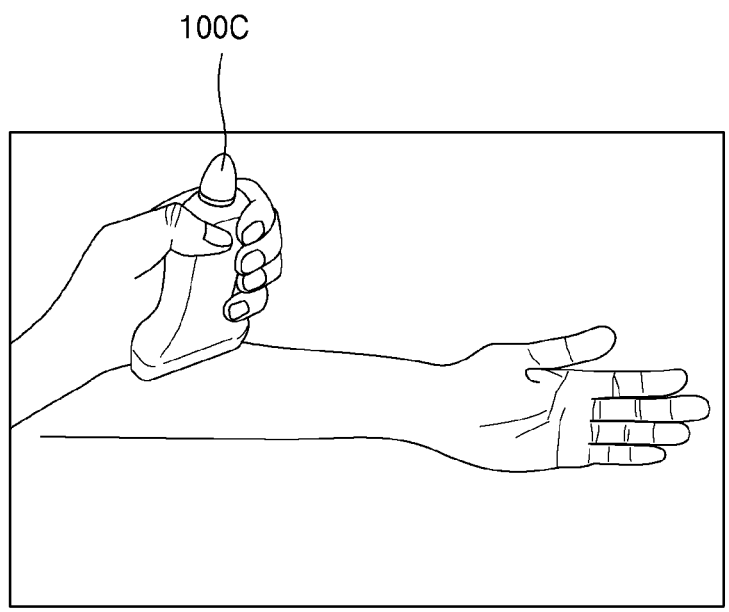

FIGS. 2A to 2C are diagrams for describing a method by which the blood glucose measurement apparatus 100 determines a user's blood glucose level based on a concentration of glucose in a user's sweat, according to an exemplary embodiment.

Referring to FIG. 2A, the blood glucose measurement apparatus 100 may include a patch 210 attached to a user's skin and configured to extract glucose from the user's sweat, and a display unit 100*a* configured to receive information about a blood glucose level transmitted from the patch 210.

The patch 210 may include glucose oxidase. As the sweat is excreted, glucose in the sweat may react with glucose oxidase in the patch 210 to generate a compound.

The blood glucose measurement apparatus 100 may receive an amount of the compound generated from the patch 210 and determine an amount of glucose excreted per unit time from the body based on the received amount of the compound. The blood glucose measurement apparatus 100 may calculate a concentration of glucose in the body based on the amount of glucose excreted per unit time from the body.

Referring to FIG. 2B, a blood glucose measurement apparatus 100*b* may measure an amount of glucose in a sweat based on reverse iontophoresis. In this case, the blood glucose measurement apparatus 100*b* may be worn on a user's wrist in a watch type and come into contact with a user's skin.

For example, when an anode and a cathode are attached to a user's skin and current is supplied between the anode and the cathode, sodium ions and chloride ions in a blood vessel under the skin, to which the anode and the cathode are attached, may be respectively moved to the cathode and the anode. At this time, uncharged glucose may also be moved outside the body through the skin together with the sodium ions. This phenomenon may be referred to as "electro-osmosis".

As glucose is moved outside the body together with the sodium ions, glucose may be oxidized by glucose oxidase to generate $H_2O_2$. Due to the generation of $H_2O_2$, two electrons may be released from an electrode in $H_2O_2$, and thus, two electrons may be generated per a glucose molecule. Therefore, the blood glucose measurement apparatus 100*b* may determine a concentration of glucose based on an amount of current generated.

Referring to FIG. 2C, a blood glucose measurement apparatus 100*c* may irradiate ultrasonic wave on a user's skin so as to easily discharge glucose from the body. As low-frequency ultrasonic wave (for example, about 20 kHz to about 100 kHz) is irradiated, permeability of the skin may increase due to cavitation. In addition, the blood glucose measurement apparatus 100*c* may increase permeability of the skin by using a solvent such as ethanol or ether.

Figure 2D:
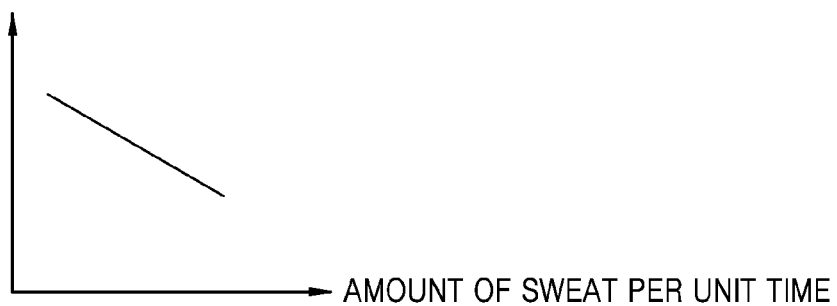
Figure 2E:
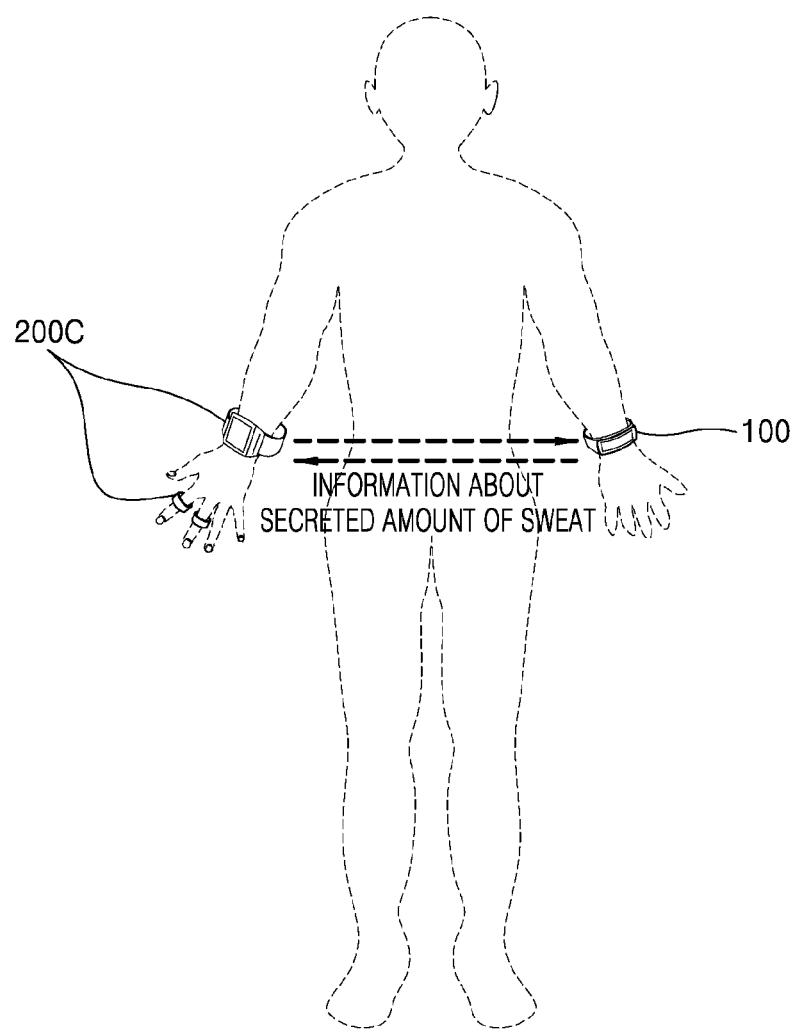

FIGS. 2D and 2E are diagrams for describing a method by which the blood glucose measurement apparatus 100 of FIG. 1 corrects a measured blood glucose level based on a concentration of glucose in a user's sweat, according to an exemplary embodiment.

Referring to FIG. 2D, an amount of glucose discharged per unit time through the user's sweat may be changed according to an amount of sweat that the user excretes, as well as a concentration of glucose in the body.

For example, as a secretion velocity of the sweat increases, a velocity at which tissue fluid is excreted through the sweat may be faster than a velocity at which glucose in a blood moves to the tissue fluid. Therefore, as the secretion velocity of the sweat increases, the concentration of glucose may be reduced. Therefore, when the user's blood glucose level is constant, the concentration of glucose in the sweat may be in inverse proportion to the secretion velocity of the sweat.

Referring to FIG. 2E, the blood glucose measurement apparatus 100*c* may directly acquire a secretion velocity of a sweat and correct a measured concentration of glucose based on the acquired secretion velocity of the sweat. For example, the blood glucose measurement apparatus 100 may receive a user's galvanic skin response from a galvanic skin response sensor 200C attached to a user's skin. The blood glucose measurement apparatus 100 may determine a secretion velocity of a sweat based on the galvanic skin response according to time. The blood glucose measurement apparatus 100 may correct a measured blood glucose level based on the secretion velocity of the sweat.

Figure 3A:
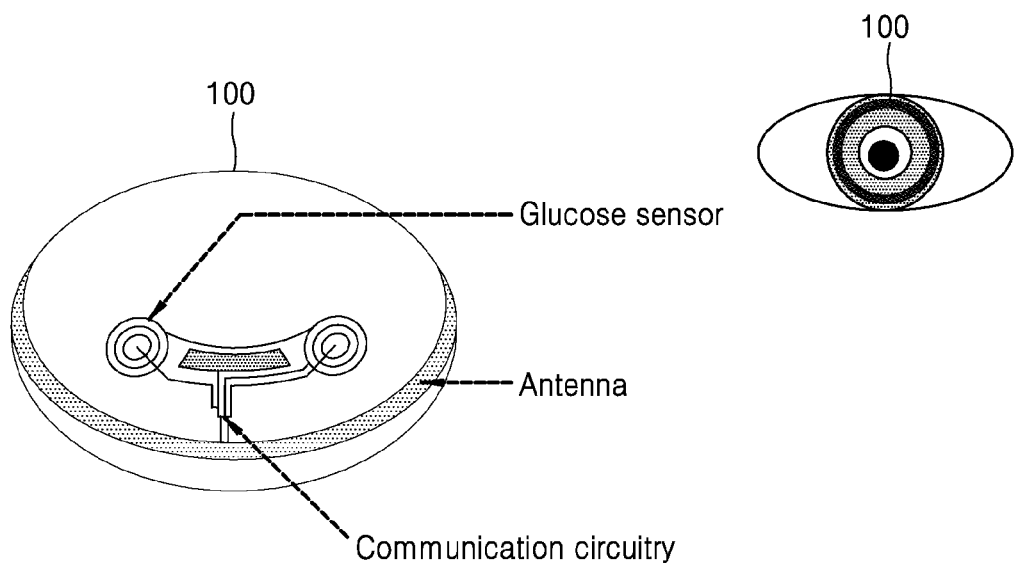
FIGS. 3A and 3B are diagrams for describing a method by which a blood glucose measurement apparatus determines a user's blood glucose level based on a concentration of glucose in a user's tear, according to an exemplary embodiment.
Figure 3B:
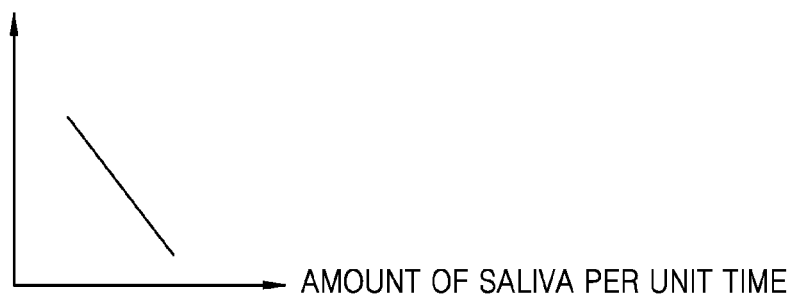

FIGS. 3A and 3B are diagrams for describing a method by which a blood glucose measurement apparatus 100 determines a user's blood glucose level based on a concentration of glucose in a user's tear, according to an exemplary embodiment.

Referring to FIG. 3A, the blood glucose measurement apparatus 100 may be a contact lens 100.

The contact lens 100 may include a glucose sensor, an antenna, and a wireless communication circuit. The glucose sensor may include glucose oxidase.

As the user sheds a tear, glucose in the tear may react with the glucose oxidase to generate hydrogen peroxide. Due to the generation of the hydrogen peroxide, the contact lens 100 may determine an amount of hydrogen peroxide generated per unit time and determine a concentration of glucose in the tear In addition, the contact lens 100 may determine the user's blood glucose level based on the concentration of glucose in the tear.

A color of the contact lens 100 may change according to the determined blood glucose level. In addition, the contact lens 100 may transmit information about the calculated blood glucose level to preset other devices by using the antenna and the wireless communication circuit.

Referring to FIG. 3B, the concentration of glucose in the tear may be changed according to a secretion velocity of the tear as well as a concentration of glucose in a body. For example, when the user's blood glucose level is constant, the concentration of glucose in the tear may be in inverse proportion to the secretion velocity of the tear. Therefore, the contact lens 100 may measure the secretion velocity of the tear and correct the measured blood glucose level based on the measured amount of the tear.

Figure 4A:
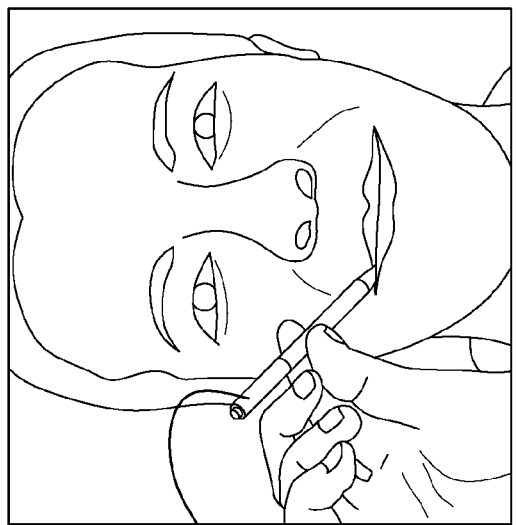
FIGS. 4A and 4B are diagrams for describing a method by which a blood glucose measurement apparatus determines a user's blood glucose level based on a concentration of glucose in a user's saliva, according to an exemplary embodiment.
Figure 4A:
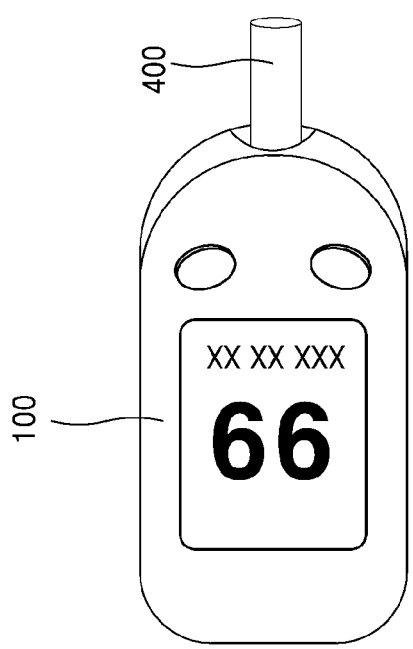
Figure 4B:
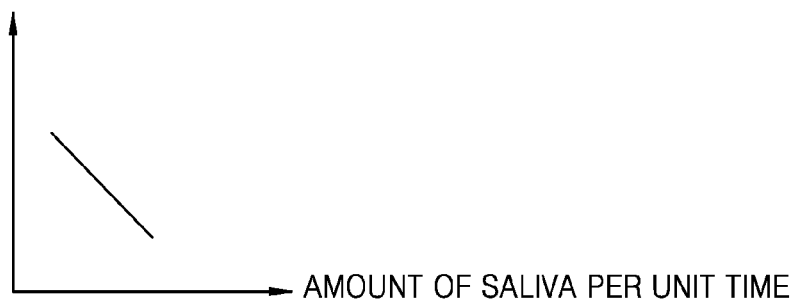

FIGS. 4A and 4B are diagrams for describing a method by which a blood glucose measurement apparatus 100 determines a user's blood glucose level based on a concentration of glucose in a user's saliva, according to an exemplary embodiment.

Referring to FIG. 4, the blood glucose measurement apparatus 100 may include a collector 400 configured to collect a user's saliva In addition, the blood glucose measurement apparatus 100 may include glucose oxidase.

When the collector 400 collecting the user's saliva is mounted on the blood glucose measurement apparatus 100, glucose in the saliva collected in the collector 400 may react with the glucose oxidase in the blood glucose measurement apparatus 100 to generate a compound. The blood glucose measurement apparatus 100 may determine an amount of glucose in the saliva based on an amount of the generated compound. When the amount of glucose included in the collector is determined, the blood glucose measurement apparatus 100 may calculate a user's blood glucose amount based on the determined amount of glucose.

Referring to FIG. 4B, the concentration of glucose in the saliva may be changed according to a secretion velocity of the saliva as well as a concentration of glucose in a body. For example, when the user's blood glucose level is constant, the concentration of glucose in the saliva may be in inverse proportion to the secretion velocity of the saliva. Therefore, the blood glucose measurement apparatus 100 may measure the secretion velocity of the saliva and correct the measured blood glucose level based on the measured amount of the tear.

Figure 5:
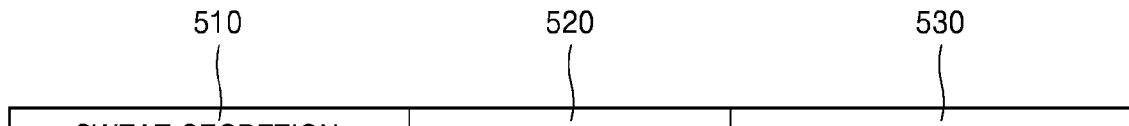
FIG. 5 is a table for describing a method by which a blood glucose measurement apparatus determines a blood glucose calculation model based on a secreted amount of body fluid, according to an exemplary embodiment.

FIG. 5 is a table for describing a method by which a blood glucose measurement apparatus 100 determines a blood glucose calculation model based on a secreted amount of body fluid, according to an exemplary embodiment.

Referring to the table of FIG. 5, a sweat secretion velocity 510 may be a measured amount of a user's sweat secreted per unit time in unit area. In addition, a measured blood glucose level 520 may be a blood glucose level measured based on a concentration of glucose in a user's sweat by the blood glucose measurement apparatus 100. In addition, a "blood glucose level in a blood" 530 may be a blood glucose level in a user's blood, which is measured in an invasive manner.

Even when the blood glucose levels in the user's blood are equal to each other, an amount of glucose included in body fluid may be changed according to a secreted amount of the body fluid. Therefore, even when the blood glucose levels in the user's blood are equal to each other, the blood glucose measurement apparatus 100 may measure a different amount of glucose according to the secreted amount of the body fluid.

An influence of the secretion velocity of the body fluid on the blood glucose measurement value may be calculated based on regression analysis. For example, the influence of the secretion velocity of the sweat on the blood glucose measurement value may be expressed as Formula 1 below:

$$\text{Glucose\_Blood} = (a*\text{BodyFluid\_level} + 1)*\text{Glucose\_measure} \quad (1)$$

In Formula 1, "Glucose_Blood" may mean a user's blood glucose level. The user's blood glucose level may mean a concentration of glucose in a user's blood. The user's blood glucose level may be acquired by collecting a user's blood sample and measuring a concentration of glucose in a user's blood based on the collected blood sample.

The blood glucose measurement apparatus 100 may receive a user's input of inputting the measured concentration of glucose in the user's blood. In addition, the blood glucose measurement apparatus 100 may receive a concentration of glucose in a user's blood from an invasive blood glucose measurement apparatus.

"Glucose_measure" may mean a blood glucose level calculated based on a concentration of glucose in a secreted blood fluid that is determined by the blood glucose measurement apparatus 100.

"BodyFluid_level" may means a secretion velocity of the body fluid. The secretion velocity of the body fluid may be an amount of body fluid measured by the blood glucose measurement apparatus 100 at the same site as a user's site where a concentration of glucose is measured. In addition, the measured amount of the body fluid may be an amount of body fluid measured by the blood glucose measurement apparatus 100, based on the same area as an area where an amount of glucose is measured.

The blood glucose measurement apparatus 100 may receive a user's input of inputting a secretion velocity of body fluid. In addition, the blood glucose measurement apparatus 100 may receive an amount of a user's body fluid from a body fluid sensor according to time.

"a" may be a variable indicating an influence of a secretion velocity of body fluid on a concentration of glucose when a user's blood glucose level is constant. The blood glucose measurement apparatus 100 may calculate the variable "a" based on regression analysis. For example, the blood glucose measurement apparatus 100 may acquire the blood glucose level 530 in the blood and the secretion velocity 510 of the body fluid, which are measured at different time, and calculate the variable "a" based on the acquired blood glucose level 530 in the blood, the acquired secretion velocity 510 of the body blood, and the blood glucose level 520 measured by the blood glucose measurement apparatus 100.

Figure 6:
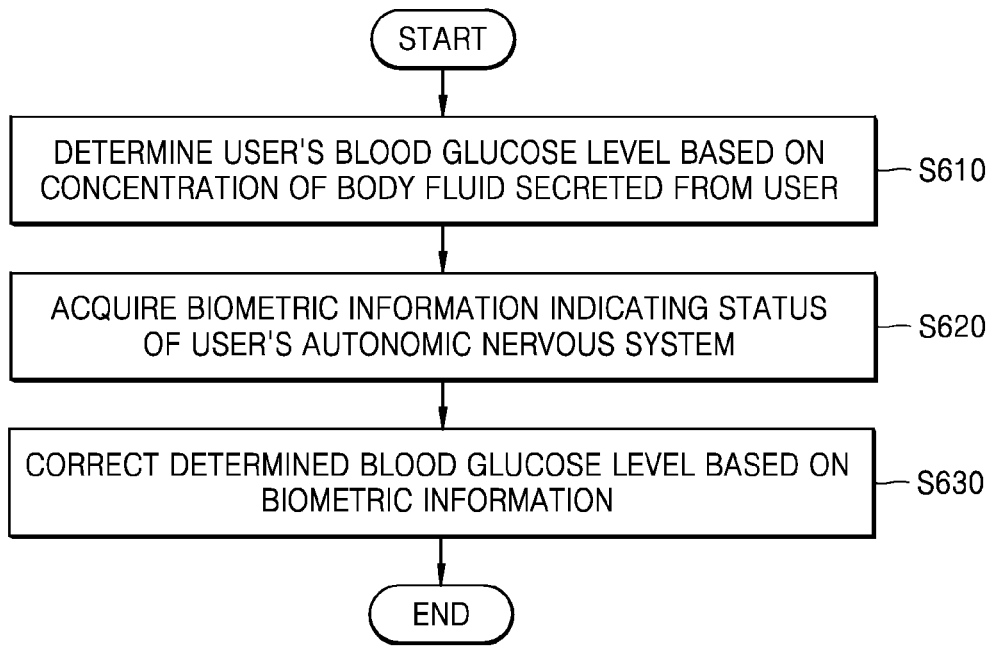
FIG. 6 is a flowchart of a method by which a blood glucose measurement apparatus corrects a user's blood glucose level based on a user's biometric information, according to an exemplary embodiment.

FIG. 6 is a flowchart of a method by which a blood glucose measurement apparatus 100 corrects a user's blood glucose level based on a user's biometric information, according to an exemplary embodiment.

In operation S610, the blood glucose measurement apparatus 100 may determine a user's blood glucose level based on a concentration of body fluid secreted from a user.

The blood glucose measurement apparatus 100 may collect body fluid secreted from the user. The body fluid may include at least one of a user's sweat, tear, saliva, and urine.

The blood glucose measurement apparatus 100 may measure a concentration of glucose in a user's sweat, tear, saliva, or urine and determine a user's blood glucose level based on the measured concentration of glucose.

In operation S620, the blood glucose measurement apparatus 100 may acquire biometric information indicating a status of a user's autonomic nervous system.

The status of the user's autonomic nervous system may mean an activity degree of at least one of a user's sympathetic nerve and parasympathetic nerve. In addition, the biometric information indicating the status of the user's autonomic nervous system may include at least one of a user's heart rate, a user's galvanic skin response, a contraction degree of a blood vessel, a size of a pupil, an amount of sweat, an amount of tear, an amount of saliva, and a body temperature.

For example, the blood glucose measurement apparatus 100 may measure a user's biometric information by using a sensor 200 provided therein. In addition, the blood glucose measurement apparatus 100 may receive the user's biometric information from a sensor 200 attached to the user.

In operation S630, the blood glucose measurement apparatus 100 may correct the determined blood glucose level based on the biometric information.

The blood glucose measurement apparatus 100 may determine the status of the user's autonomic nervous system based on the biometric information. The blood glucose measurement apparatus 100 may determine a secretion velocity of body fluid based on the determined status of the user's autonomic nervous system. The blood glucose measurement apparatus 100 may correct the determined blood glucose level based on the determined secretion velocity of the body fluid.

FIGS. 7A to 7D are diagrams for describing a method by which the blood glucose measurement apparatus 100 determines the secretion velocity of the body fluid based on the status of the user's autonomic nervous system, according to an exemplary embodiment.

Referring to FIG. 7A, the autonomic nervous system and the secretion velocity of the body fluid may exhibit a constant correlation.

Figure 7B:
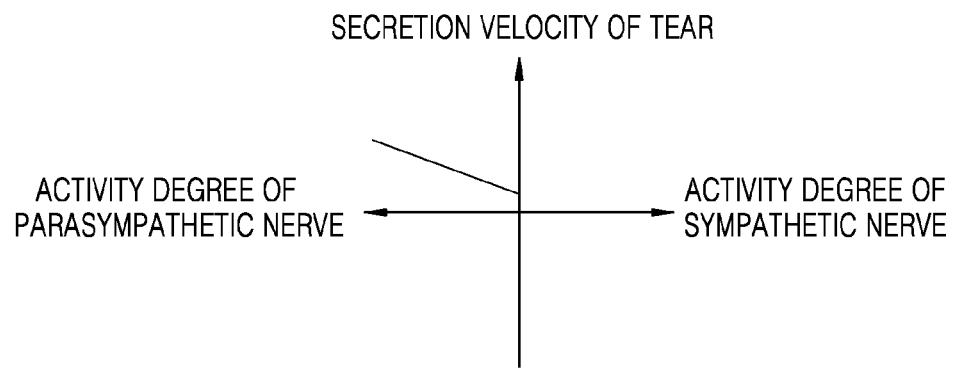
Figure 7C:
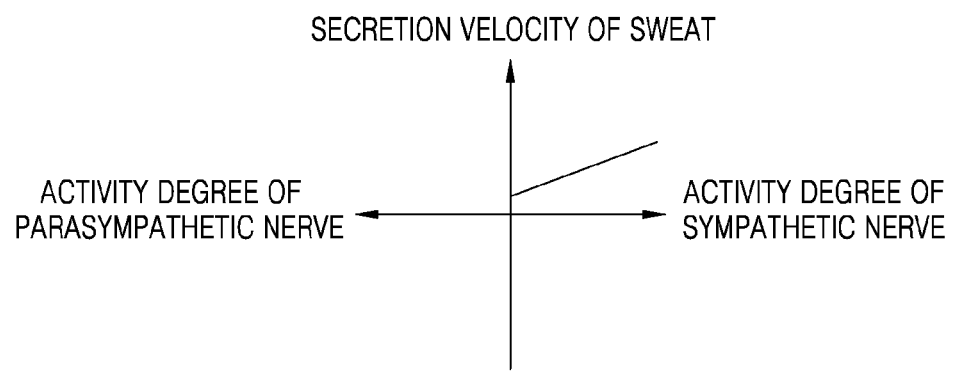
Figure 7D:
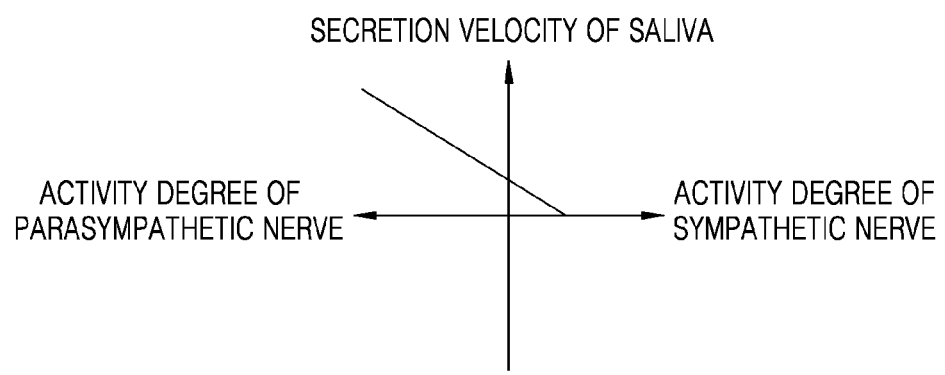

For example, referring to FIG. 7B, as an activity degree of a parasympathetic nerve increases, the secretion velocity of the tear may increase. Referring to FIG. 7C, as an activity degree of a sympathetic nerve increases, the secretion velocity of the tear may increase. Referring to FIG. 7D, as the activity degree of the sympathetic nerve increases, the secretion velocity of the saliva may decrease, and as the activity degree of the parasympathetic nerve increases, the secretion velocity of the saliva may increase.

Therefore, even when the blood glucose measurement apparatus 100 directly measure or does not receive the secretion velocity of the body fluid or the secreted amount of the body fluid, the blood glucose measurement apparatus 100 may measure the activity degree of the sympathetic nerve or the activity degree of the parasympathetic nerve and acquire the secretion velocity of the body fluid or the secreted amount of the body fluid based on the measured activity degree of the sympathetic nerve or the measured activity degree of the parasympathetic nerve.

FIGS. 8A to 8D are diagrams for describing a method by which the blood glucose measurement apparatus 100 determines the status of the user's autonomic nervous system based on the user's biometric information, according to an exemplary embodiment.

Referring to FIG. 8A, specific body organs exhibit a status of a sympathetic nervous system. According to exemplary embodiments, the body organs exhibiting the status of the autonomic nervous system may be referred to as effector organs.

Figure 8B:
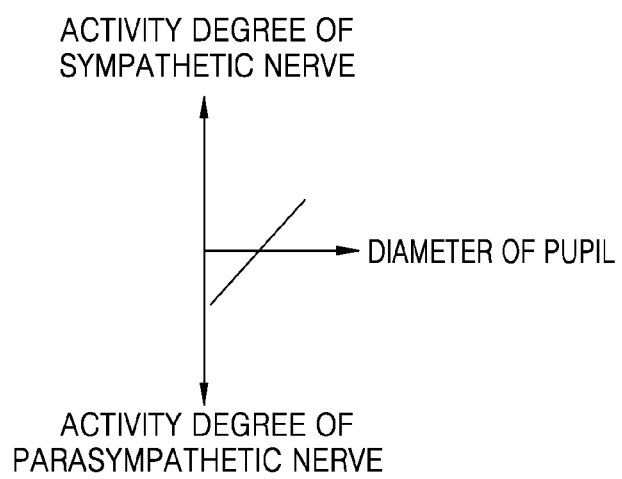
Figure 8C:
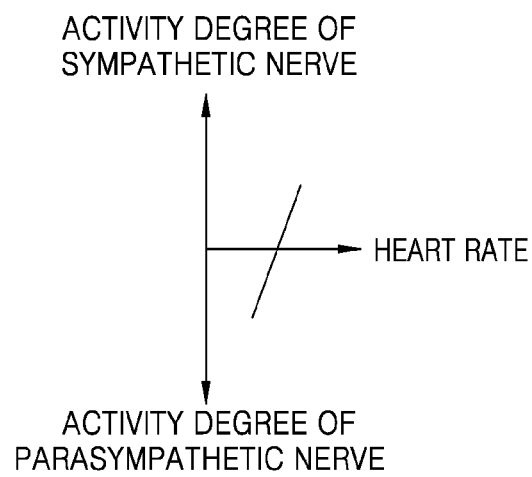
Figure 8D:
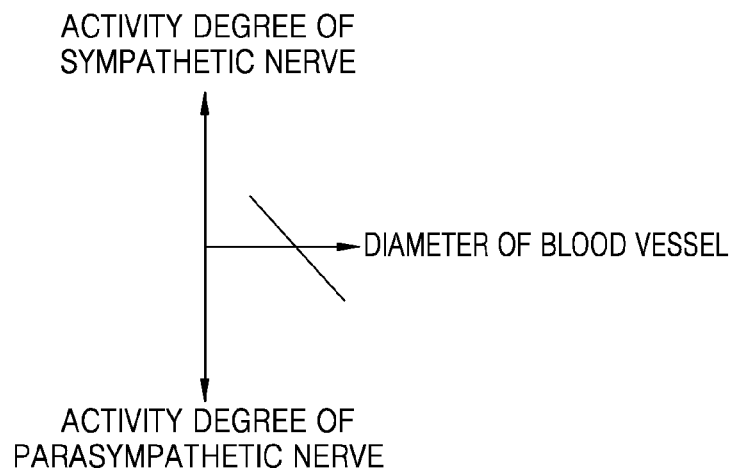

For example, referring to FIG. 8B, a diameter of a pupil may increase when a sympathetic nerve is activated and may decrease when a parasympathetic nerve is activated. For example, referring to FIG. 8C, a heart rate or a heart conductivity may increase when the sympathetic nerve is activated and may decrease as the parasympathetic nerve is activated. In addition, referring to FIG. 8D, a diameter of a blood vessel may increase when the sympathetic nerve is activated.

Therefore, the blood glucose measurement apparatus 100 may receive the user's biometric information from the sensor 200 provided therein or from the sensor 200 worn on the user, and determine the status of the user's autonomic nervous system based on the received biometric information.

Figure 9:
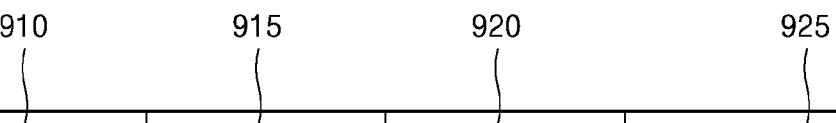
FIG. 9 is a table for describing a method by which a blood glucose measurement apparatus determines a status of a user's autonomic nervous system based on a user's biometric information, according to another exemplary embodiment.

FIG. 9 is a table for describing a method by which the blood glucose measurement apparatus 100 determines the status of the user's autonomic nervous system based on the user's biometric information, according to another exemplary embodiment. The blood glucose measurement apparatus 100 may store a method of determining the status of the user's autonomic nervous system by using at least one piece of the biometric information as a variable. For example, the method of determining the status of the user's autonomic nervous system by using at least one piece of the biometric information as a variable may be expressed as Formula 2 below.

$$\text{Autonomic\_nervous\_status} = 1/n * \Sigma[b_n * \text{Body\_data}_n] \quad (2)$$

In Formula 2, "Autonomic_nervous_status" may mean the status of the user's autonomic nervous system. When the status of the user's autonomic nervous system is a positive number, it represents an activity degree of a sympathetic nerve, and when the status of the user's autonomic nervous system is a negative number, it represents an activity degree of a parasympathetic nerve.

"Body_data$_n$" may mean the user's biometric information. For example, Body_data$_n$ may be at least one of a user's heart rate, a user's galvanic skin response, a contraction degree of a blood vessel, a size of a pupil, an amount of sweat, an amount of tear, an amount of saliva, and a body temperature.

"$b_n$" may be a coefficient indicating an influence of the biometric information on the status of the user's autonomic nervous system. "$b_n$" may be different for each user in a reference range. In addition, "$b_n$" may be determined by regression analysis. "$b_n$" may be experimentally measured and prestored and may be updated according to a user's condition.

Referring to FIG. 9, the blood glucose measurement apparatus 100 may determine the status of the user's autonomic nervous system based on the biometric information. For example, the blood glucose measurement apparatus 100 may receive a heart rate 910 from the ECG sensor 200b, receive information 915 about heart rate variability (HRV) from the PPG sensor 200d, and receive information 920 about a diameter of a pupil from the glasses 200a with a built-in camera. The blood glucose measurement apparatus 100 may determine a status 925 of a user's autonomic nervous system according to the model of Formula 2, based on the received heart rate, the received information about the HRV, and the received information about the diameter of the pupil.

FIG. 10 is a table for describing a method by which the blood glucose measurement apparatus 100 determines a secretion velocity of body fluid based on the status 925 of the user's autonomic nervous system, according to another exemplary embodiment.

Referring to FIG. 10, the blood glucose measurement apparatus 100 may determine the secretion velocity of the body based on the status 925 of the user's autonomic nervous system. For example, the blood glucose measurement apparatus 100 may determine a sweat secretion velocity 930, a saliva secretion velocity 940, or a tear secretion velocity 950 based on the status 925 of the user's autonomic nervous system.

The blood glucose measurement apparatus 100 may store a method of determining the secretion velocity of the body fluid based on the status 925 of the user's autonomic nervous system. For example, the method of determining the secretion velocity of the body fluid based on the status 925 of the user's autonomic nervous system may be expressed as Formula 3 below.

$$\text{BodyFluid\_velocity} = c * \text{Autonomic\_nervous\_status} \quad (3)$$

In Formula 3, "BodyFluid_velocity" may mean the secretion velocity of the body fluid.

"Autonomic_nervous_status" may mean the status 925 of the user's autonomic nervous system.

"c" may be a coefficient indicating the secretion velocity of the body fluid based on the status 925 of the user's autonomic nervous system. "c" may be different according to a kind of the body fluid. "c" may be different for each user in a reference range and may be determined based on regression analysis. "c" may be experimentally measured and prestored and may be updated according to a user's condition.

The blood glucose measurement apparatus 100 may determine the secretion velocity of the body fluid based on the status 925 of the user's autonomic nervous system. For example, the blood glucose measurement apparatus 100 may determine the secretion velocity of the sweat, the tear, or the saliva by substituting a value of the status 925 of the autonomic nervous system into the model of Formula 3.

Figure 11:
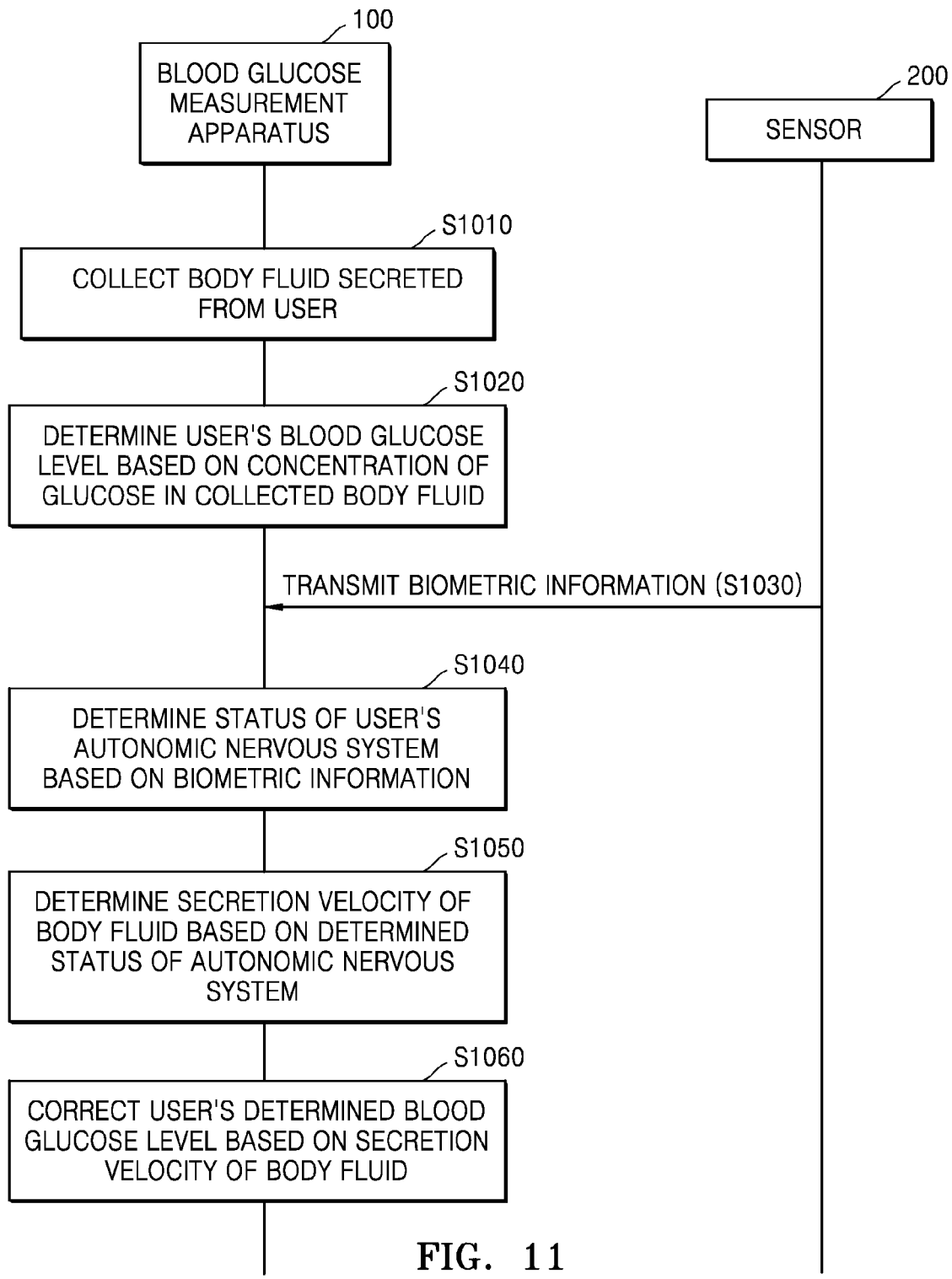
FIG. 11 is a flowchart of a method by which a blood glucose measurement apparatus receives a user's biometric information from a biometric sensor and corrects a calculated blood glucose level based on the received biometric information, according to an exemplary embodiment.

FIG. 11 is a flowchart of a method by which the blood glucose measurement apparatus 100 receives a user's biometric information from a biometric sensor 200 and corrects a calculated blood glucose level based on the received biometric information, according to an exemplary embodiment.

In operation S1010, the blood glucose measurement apparatus 100 may collect body fluid secreted from a user.

The body fluid may include at least one of a user's sweat, tear, saliva, and urine.

In operation S1020, the blood glucose measurement apparatus 100 may determine a user's blood glucose level based on a concentration of glucose in the collected body fluid.

The blood glucose measurement apparatus 100 may measure a concentration of glucose in the user's sweat, tear, saliva, or urine and determine the user's blood glucose level based on the measured concentration of glucose in the user's sweat, tear, saliva, or urine.

In operation S1030, the sensor 200 may transmit the user's biometric information to the blood glucose measurement apparatus 100. The sensor 200 may be attached to a user's body and configured to measure the user's biometric information. Examples of, the sensor 200 may include an ECG sensor 200*b*, a GSR sensor 200*c*, and a thermometer 200*e*, but are not limited thereto.

The sensor 200 may transmit the user's biometric information to the blood glucose measurement apparatus 100 in response to a reception of a request from the blood glucose measurement apparatus 100. In addition, the sensor 200 may transmit the measured biometric information to the blood glucose measurement apparatus 100 in response to an occurrence of a preset event. In this case, the sensor 200 may transmit, to the blood glucose measurement apparatus 100, a type of the biometric information, the time at which the biometric information has been measured, and information about a user from whom the biometric information has been measured, together with the biometric information.

The sensor 200 may transmit the measured biometric information to the blood glucose measurement apparatus 100 by using a short-range wireless communication. For example, the sensor 200 may transmit the measured biometric information to the blood glucose measurement apparatus 100 by using near field communication (NFC) or Bluetooth communication.

In operation S1040, the blood glucose measurement apparatus 100 may determine the status of the user's autonomic nervous system based on the biometric information.

The status of the user's autonomic nervous system may mean an activity degree of at least one of a user's sympathetic nerve and parasympathetic nerve.

In operation S1050, the blood glucose measurement apparatus 100 may determine a secretion velocity of body fluid based on the determined status of the user's autonomic nervous system.

In operation S1060, the blood glucose measurement apparatus 100 may correct the determined blood glucose level based on the secretion velocity of the body fluid.

Figure 12A:
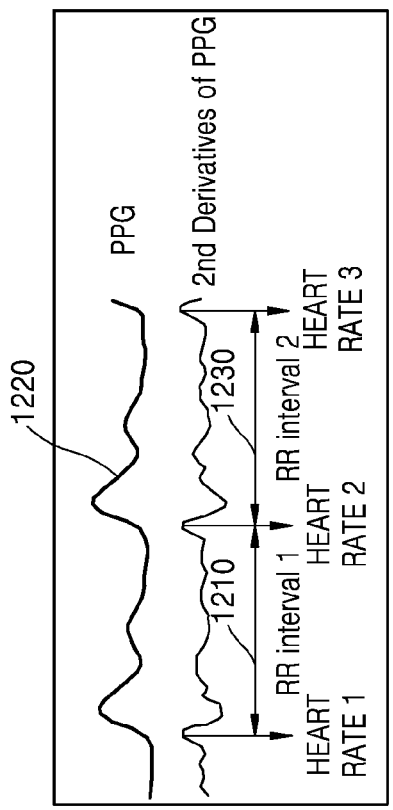
FIGS. 12A and 12B are diagrams for describing a method by which a blood glucose measurement apparatus determines a status of a user's autonomic nervous system based on biometric information about a heart beat, according to an exemplary embodiment.
Figure 12A:
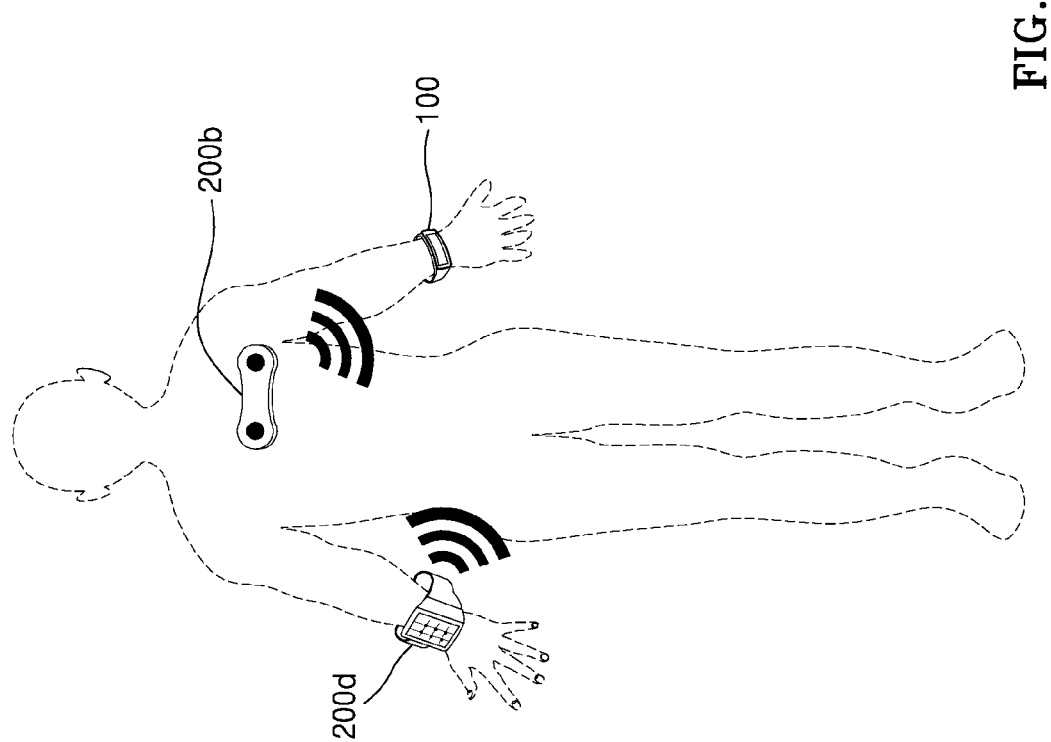
Figure 12B:
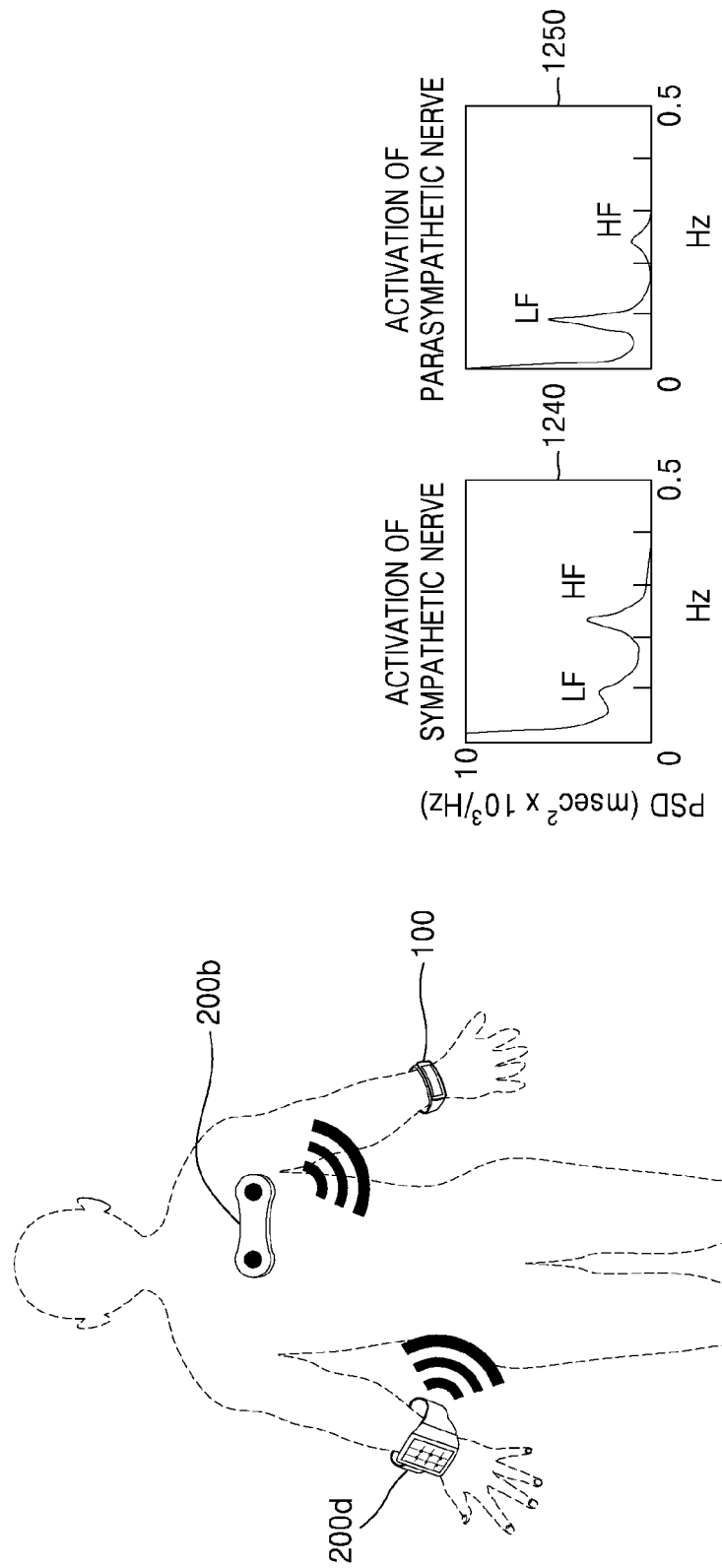

FIGS. 12A and 12B are diagrams for describing a method by which the blood glucose measurement apparatus 100 determines a status of a user's autonomic nervous system based on biometric information about a heart beat, according to an exemplary embodiment.

Referring to FIG. 12A, the blood glucose measurement apparatus 100 may receive biometric information about a user's heart beat from a PPG sensor 200*d* or an ECG sensor 200*b*.

The PPG sensor 200*d* may irradiate light of a specific wavelength band on a body, detect reflected or transmitted light from the body, measure a blood flow rate in a blood vessel, which is increased or decreased by the heart beat, and measure a user's pulse wave 1210 based on the measured blood flow rate.

In addition, the PPG sensor 200*d* may calculate information about a user's heart beat based on the measured pulse wave 1210. For example, the PPG sensor 200*d* may determine a heart beat time point by differentiating the pulse wave 1210. When the heart beat time point is determined, the PPG sensor 200*d* may calculate a heart rate per minute into inter-beat (RR) intervals 1220 and 1230. The PPG sensor 200*d* may calculate inter-beat intervals 1220 and 1230 based on the determined heart beat time point.

The blood glucose measurement apparatus 100 may receive information about a user's heart rate from the PPG sensor 200*d*. The blood glucose measurement apparatus 100 may determine the status of the user's autonomic nervous system based on the received information about the user's heart rate.

Referring to FIG. 12B, the PPG sensor 200*d* may calculate heart rate variability (HRV) 1240 and 1250 by modulating the inter-beat intervals in a frequency domain.

A low frequency band LF (about 0.04 Hz to about 0.15 Hz) in the HRV 1240 and 1250 may indicate an activity degree of a sympathetic nerve. In addition, a high frequency band HF (about 0.15 Hz to about 0.4 Hz) in the HRV 1240 and 1250 may indicate an activity degree of a parasympathetic nerve. For example, when the parasympathetic nerve is activated, the HRV 1240 may increase in the high frequency band HF and decrease in the low frequency band LF. In addition, when the sympathetic nerve is activated, the HRV 1250 may decrease in the high frequency band HF and increase in the low frequency band LF.

Furthermore, an LF/HF ratio of the low frequency band to the high frequency band may exhibit a balance of the sympathetic nerve and the parasympathetic nerve.

The blood glucose measurement apparatus 100 may receive information about a user's inter-beat intervals or HRV from the PPG sensor 200*d*. When the information about the user's inter-beat intervals or HRV is received from the PPG sensor 200*d*, the blood glucose measurement apparatus 100 may determine the status of the user's autonomic nervous system based on the information about the user's inter-beat intervals or HRV.

Figure 13A:
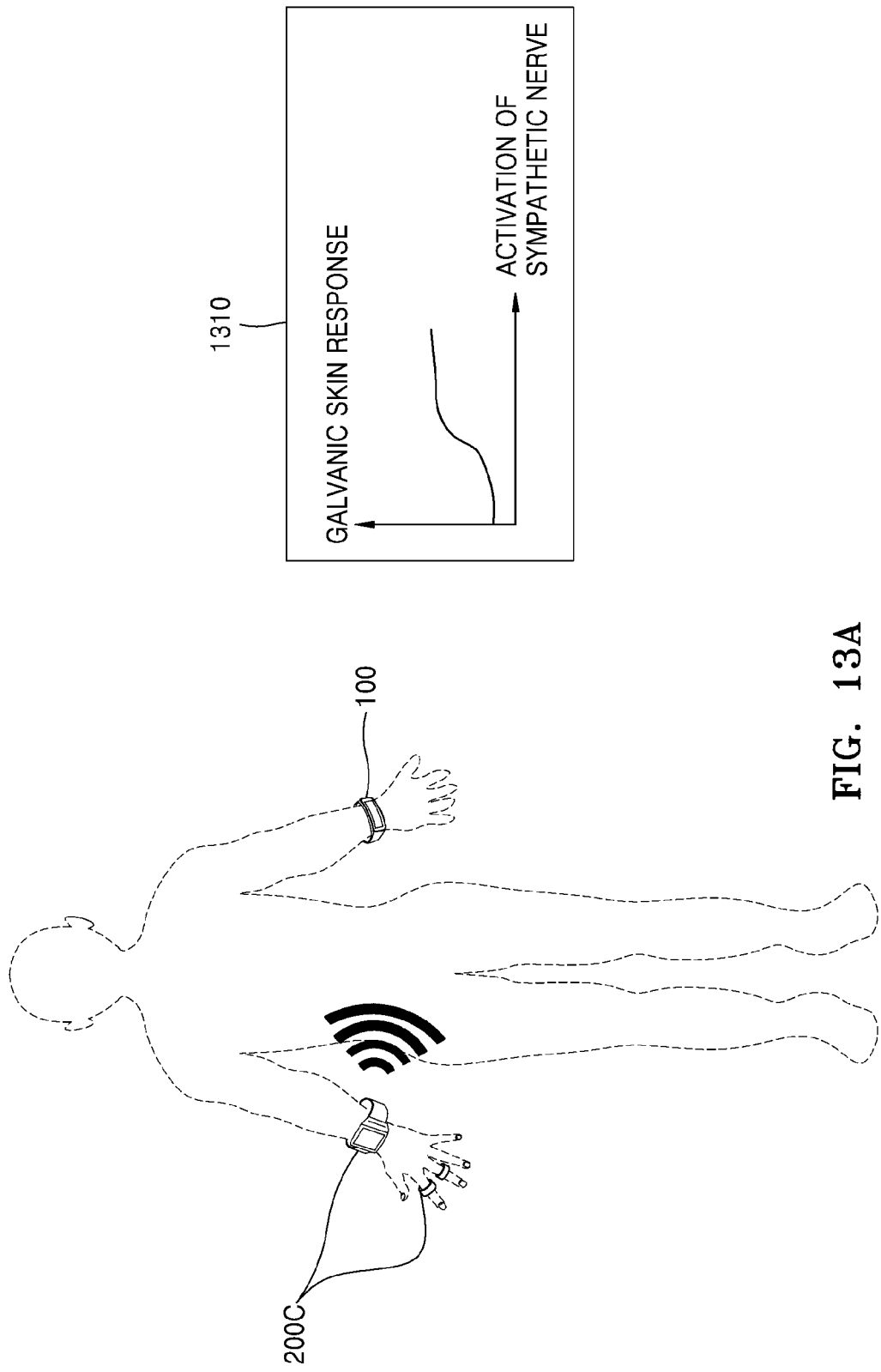
FIGS. 13A and 13B are diagrams for describing a method by which a blood glucose measurement apparatus determines a status of a user's autonomic nervous system based on a galvanic skin response (also known as a skin conductance), according to another exemplary embodiment.
Figure 13B:
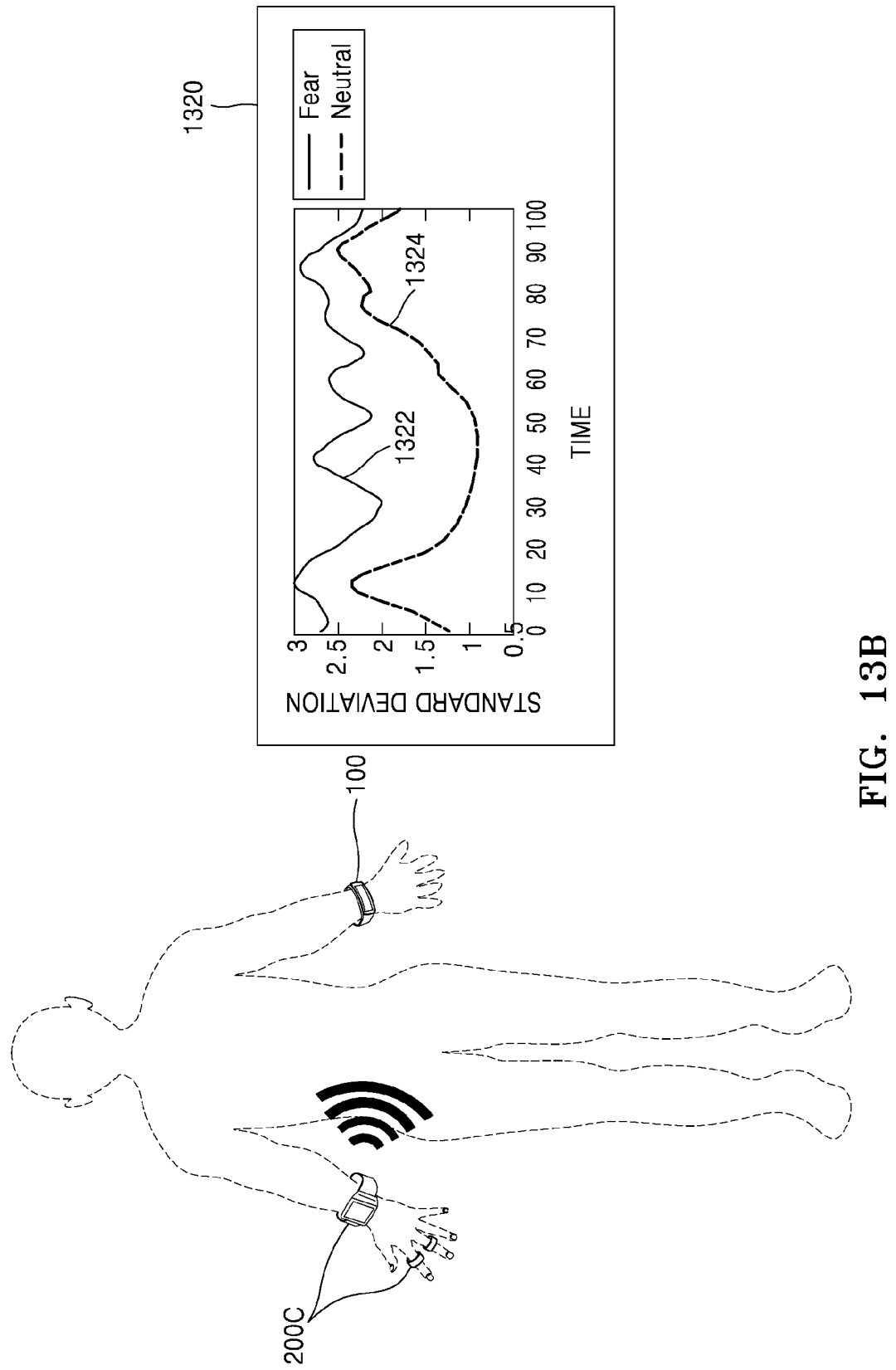

FIGS. 13A and 13B are diagrams for describing a method by which a blood glucose measurement apparatus 100 determines a status of a user's autonomic nervous system based on biometric information about a user's galvanic skin response, according to another exemplary embodiment.

Referring to FIG. 13A, the blood glucose measurement apparatus 100 may receive the biometric information about the user's galvanic skin response from a GSR sensor 200*c*.

The GSR sensor 200*c* may be a sensor using characteristics that an electrical conductance of a skin changes according to a moisture level of the skin. For example, as sweat increases, electrical skin resistance may decrease. In addition, as the skin becomes drier, the electrical skin resistance may increase.

As illustrated in a graph 1310 showing a change in the galvanic skin response according to sympathetic nerve activation, the galvanic skin response increases as the sympathetic nerve is further activated.

At this time, the blood glucose measurement apparatus 100 may determine the status of the user's autonomic nervous system based on the user's galvanic skin response. For example, the blood glucose measurement apparatus 100 may determine that the sympathetic nerve is further activated as the galvanic skin response increases.

Referring to FIG. 13B, standard deviation of the galvanic skin response exhibit a status of an autonomic nervous system. For example, referring to a graph 1320 showing a change in standard deviations 1322 and 1324 of the galvanic skin response according to the time, the standard deviation 1322 may increase when a sympathetic nerve is activated, and the standard deviation 1324 may decrease when a parasympathetic nerve is activated.

Accordingly, the blood glucose measurement apparatus 100 may calculate the standard deviation of the galvanic skin response according to the time. The blood glucose measurement apparatus 100 may determine that the sympathetic nerve is further activated as the standard deviation of the galvanic skin response according to the time increases.

Figure 14:
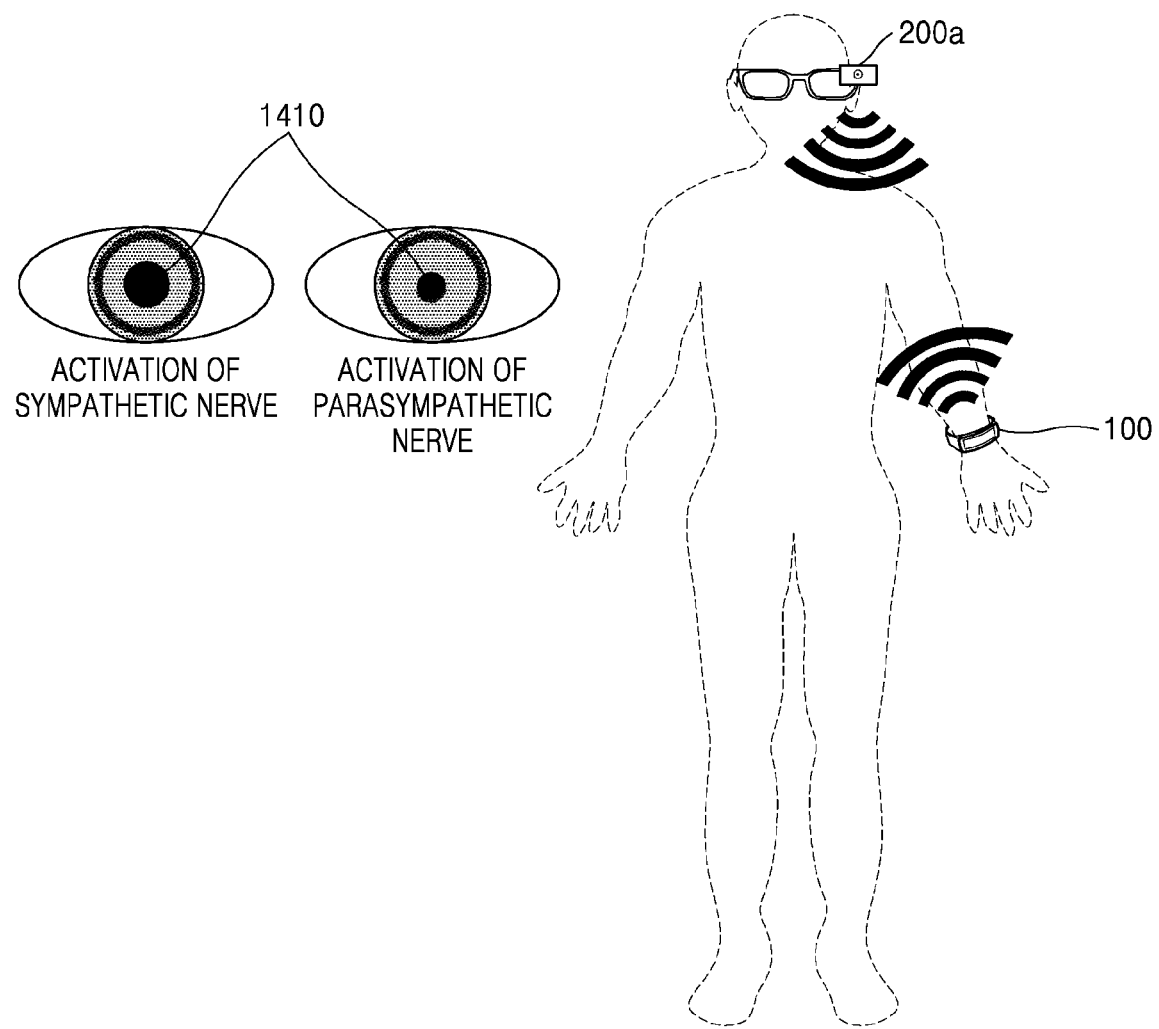
FIG. 14 is a diagram for describing a method by which a blood glucose measurement apparatus determines a status of a user's autonomic nervous system based on biometric information about a diameter of a pupil, according to an exemplary embodiment.

FIG. 14 is a diagram for describing a method by which a blood glucose measurement apparatus 100 determines a status of a user's autonomic nervous system based on biometric information about a diameter of a pupil 1410, according to an exemplary embodiment.

Referring to FIG. 14, the blood glucose measurement apparatus 100 may receive the information about the diameter of the user's pupil 1410 from glasses 200a that a user wears.

The glasses 200a may include a camera configured to capture an image of a user's eye. The glasses 200a may periodically capture the image of the user's eye through the camera and identify the pupil 1410 from the captured image. When the user's pupil 1410 is identified, the glasses 200a may measure the diameter of the pupil 1410.

The glasses 200a may transmit information about the measured diameter of the pupil 1410 to the blood glucose measurement apparatus 100.

The blood glucose measurement apparatus 100 may determine a status of a user's autonomic nervous system based on the information about the diameter of the pupil 1410. For example, the blood glucose measurement apparatus 100 may determine that an activity degree of a sympathetic nerve is higher as the diameter of the pupil 1410 is larger than a reference diameter and an activity degree of a parasympathetic nerve is higher as the diameter of the pupil 1410 is smaller than the reference diameter.

Figure 15:
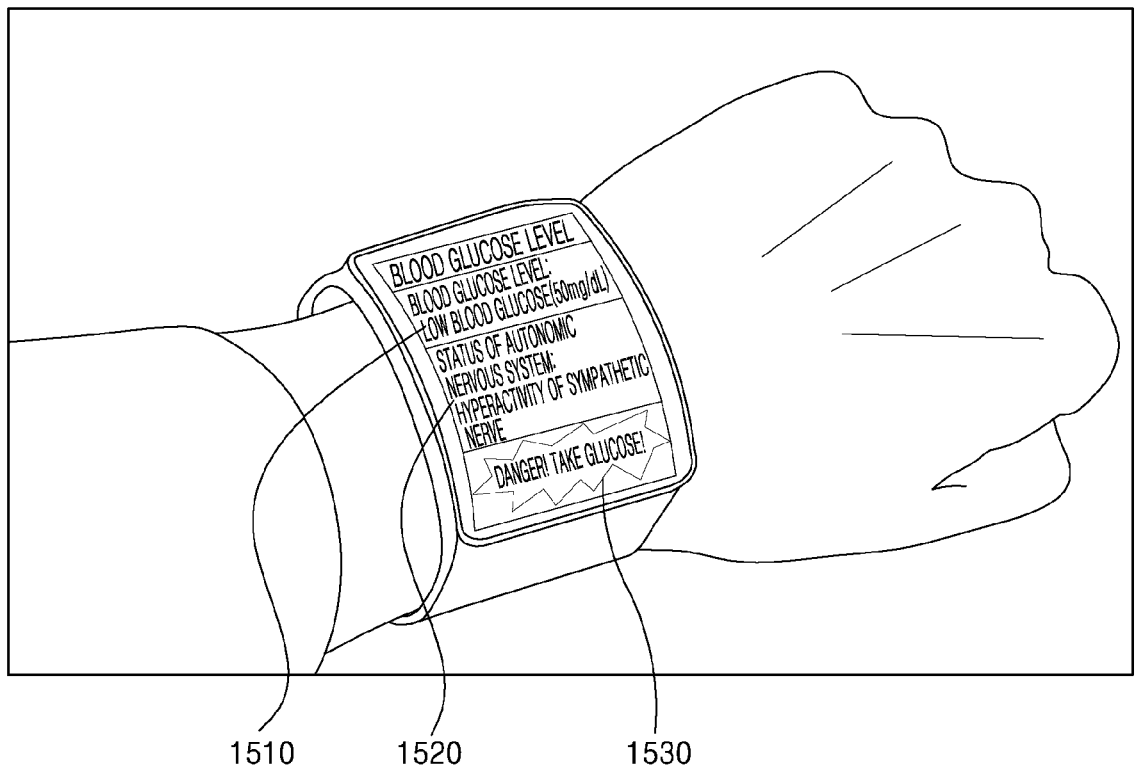
FIG. 15 is a diagram for describing a method by which a blood glucose measurement apparatus displays a status of a user's autonomic nervous system and a user's blood glucose level, according to an exemplary embodiment.

FIG. 15 is a diagram for describing a method by which a blood glucose measurement apparatus 100 displays a status of a user's autonomic nervous system and a user's blood glucose level, according to an exemplary embodiment.

Referring to FIG. 15, the blood glucose measurement apparatus 100 may display a user's blood glucose level 1510, a status of a user's autonomic nervous system 1520, and a notice message 1530 (e.g., a warning message) associated with a blood glucose level.

In addition, when the user's blood glucose level is out of a preset normal range, the blood glucose measurement apparatus 100 may generate a signal notifying the user of danger. For example, the blood glucose measurement apparatus 100 may generate a vibration or a sound so as to notify that the blood glucose level is not in the normal range.

In addition, when the user's blood glucose level is maintained for a predetermined period in a state of being out of the preset normal range, the blood glucose measurement apparatus 100 may generate the signal notifying the user of danger. For example, even a person who is in a normal condition may exceed a blood glucose level of 200 mg/dl 30 minutes after meal. However, in the case of the person who is in the normal condition, when the blood glucose level increases, insulin may be normally secreted to reduce the blood glucose level. However, since a diabetic patient does not normally secrete insulin, the diabetic patient may maintain a blood glucose level of 200 mg/dl or more for a longer time than a reference period. Therefore, only when the user's blood glucose level is maintained for a preset period in a state of being out of the preset normal range, the blood glucose measurement apparatus 100 may generate the signal notifying the user of danger.

In addition, when it is expected that the user's blood glucose level will be out of the preset normal range, the blood glucose measurement apparatus 100 may generate the signal notifying the user of danger. For example, when a decreasing speed of the user's blood glucose level is higher than a reference speed or an increasing speed of the user's blood glucose level is higher than the reference speed, the blood glucose measurement apparatus 100 may generate the signal notifying the user of danger before the user's blood glucose level departs from the normal range.

Figure 16A:
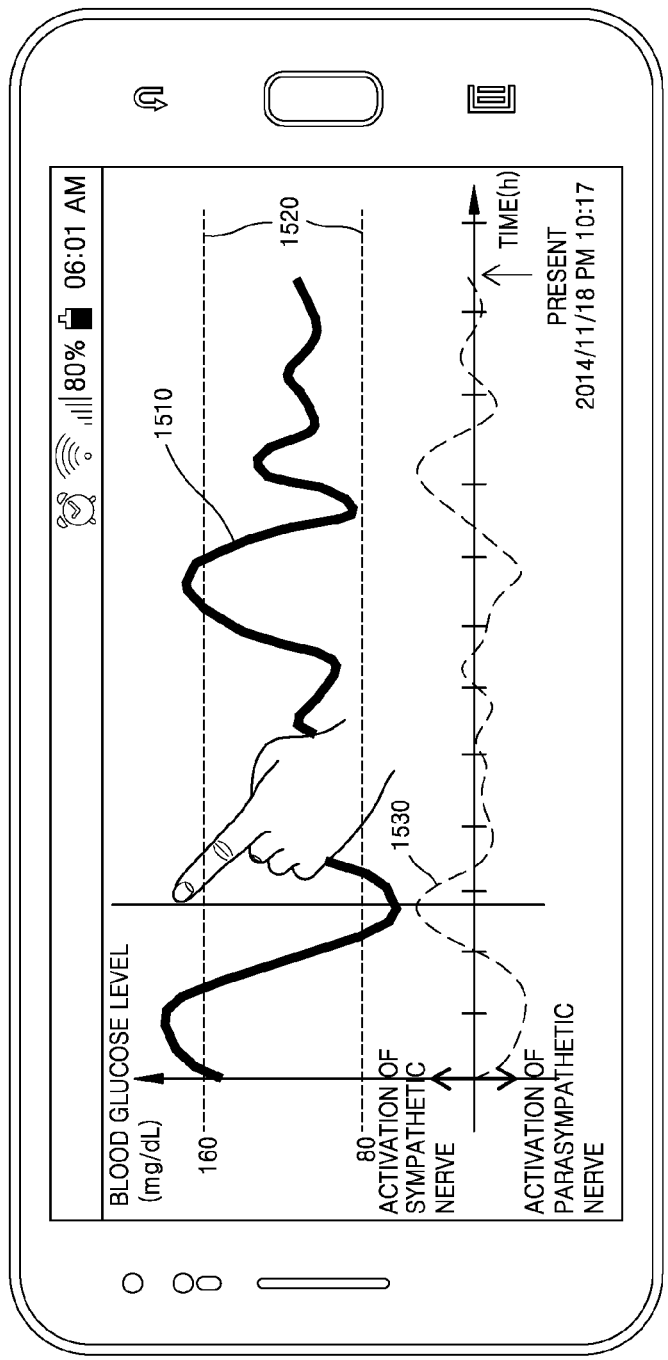
FIGS. 16A to 16C are diagrams for describing a method by which a blood glucose measurement apparatus displays a status of a user's autonomic nervous system and a user's blood glucose level, according to another exemplary embodiment.
Figure 16B:
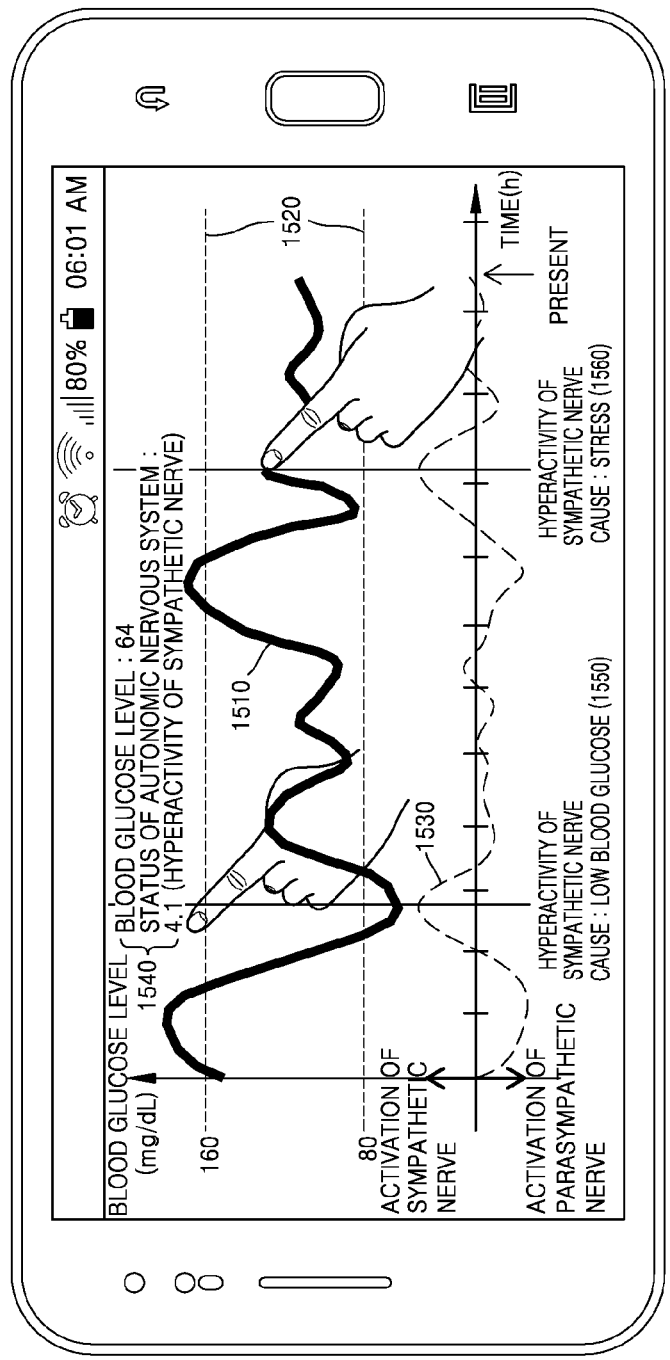
Figure 16C:
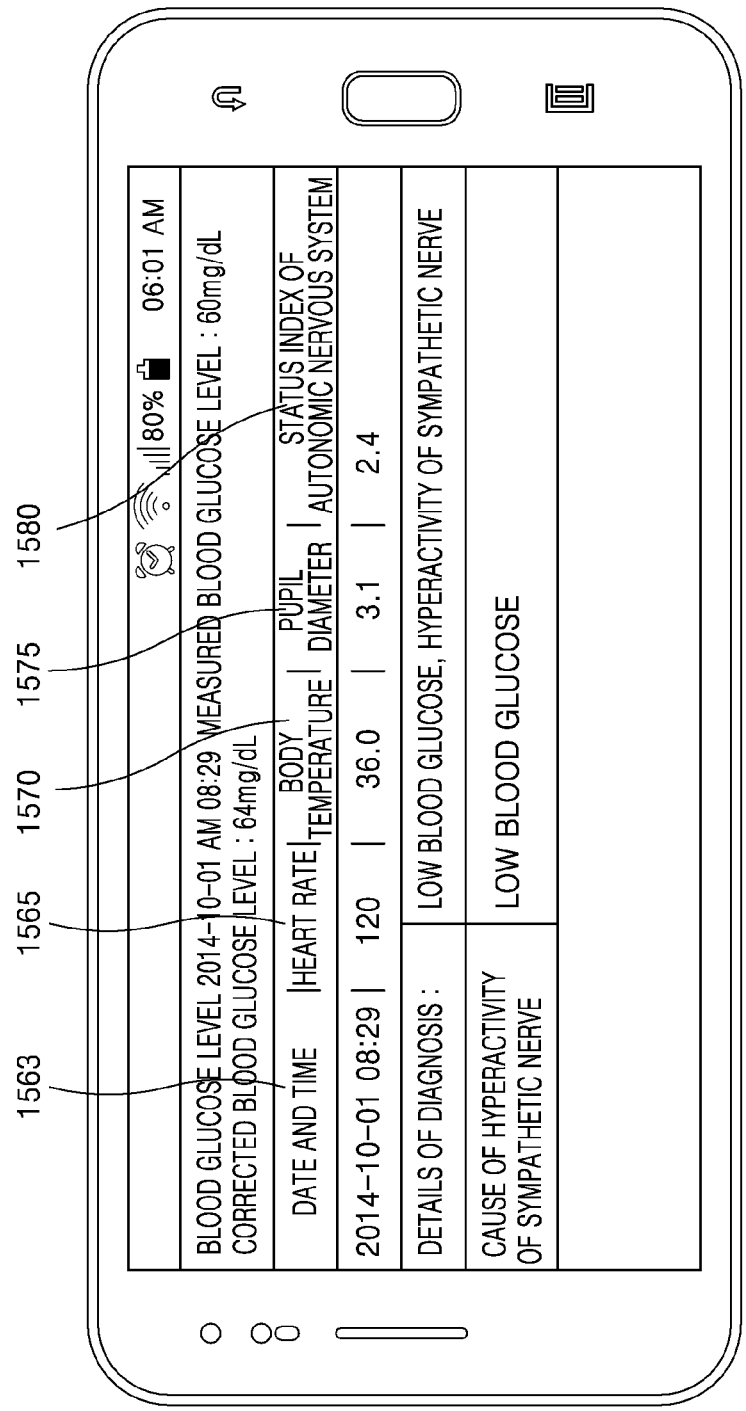

FIGS. 16A to 16C are diagrams for describing a method by which the blood glucose measurement apparatus displays a status of a user's autonomic nervous system and a user's blood glucose level, according to another exemplary embodiment.

Referring to FIG. 16A, the blood glucose measurement apparatus 100 may display a graph 1510 showing a change in the blood glucose level according to the time.

In addition, the blood glucose measurement apparatus 100 may display a normal range of the blood glucose level 1520 together with the graph 1510 showing the change in the blood glucose level. For example, the blood glucose measurement apparatus 100 may display limit lines showing a maximum value and a minimum value of the normal range 1520 on the graph 1510 showing the change in the blood glucose level.

In addition, the blood glucose measurement apparatus 100 may display a graph 1530 showing a status of a user's autonomic nervous system together with the graph 1510 showing the change in the blood glucose level.

Referring to FIG. 16B, the blood glucose measurement apparatus 100 may display details of diagnosis made at a time point selected by the user.

When receiving a user's input of selecting one time point on the graph 1510 showing the change in the blood glucose level, the blood glucose measurement apparatus 100 may display information 1540 about the blood glucose level and the autonomic nervous system at the selected time point.

For example, the blood glucose measurement apparatus 100 may display details about the blood glucose level and status of the autonomic nervous system. For example, when the blood glucose level at the selected time point is lower than the preset normal range, the blood glucose measurement apparatus 100 may display information indicating that the blood glucose level is low at the selected time point.

In addition, the blood glucose measurement apparatus 100 may display details of diagnosis about the status of the autonomic nervous system based on a status index of the autonomic nervous system. For example, when the status index of the autonomic nervous system is higher than a preset normal range, the blood glucose measurement apparatus 100 may display information indicating that the sympathetic nerve has been activated.

In addition, when the status index of the autonomic nervous system is out of the preset normal range, the blood glucose measurement apparatus 100 may display information 1550 and 1560 about causes that the status index of the autonomic nervous system is out of the preset normal range.

For example, the cause of activation of the sympathetic nerve may be a low blood glucose level, motion, excitement, or tension. In addition, the cause of activation of the parasympathetic nerve may be a high blood glucose level or a rest. Accordingly, the blood glucose measurement apparatus 100 may display information about the causes that the status index of the autonomic nervous system is out of the preset normal range, based on the user's blood glucose level and the user's biometric information.

For example, when it is determined that the user's blood glucose level is low, the user's motion quantity is a reference value or less, and the sympathetic nerve has been activated, the blood glucose measurement apparatus 100 may determine that the cause of the activation of the sympathetic nerve is the low blood glucose level. In addition, when it is determined that the user's blood glucose level is normal, the user's motion quantity is a reference value or less, and the sympathetic nerve has been activated, the blood glucose measurement apparatus 100 may determine that the cause of the activation of the sympathetic nerve is a stress.

Referring to FIG. 16C, the blood glucose measurement apparatus 100 may display details of a blood glucose level measured at a time point selected by the user.

When receiving a user's input of selecting one time point on the graph of FIG. 16B, the blood glucose measurement apparatus 100 may display details of the blood glucose level measured at the selected time point.

For example, the blood glucose measurement apparatus 100 may display a date and time 1563 of the selected time point. In addition, the blood glucose measurement apparatus 100 may display biometric data used for correcting the blood glucose level at the selected time point. For example, when the biometric data used for correcting the blood glucose level is a heart rate, a body temperature, and a pupil diameter, the blood glucose measurement apparatus 100 may display measured values of a heart rate 1565, a body temperature 1570, and a pupil diameter 1575. The status index of the autonomic nervous system 1580 may also be displayed for the selected time point.

Figure 17A:
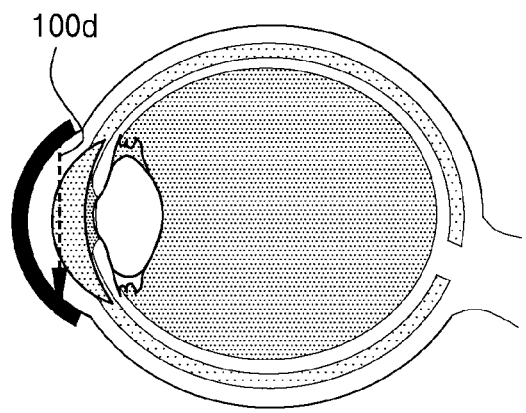
FIGS. 17A and 17B are diagrams for describing a method by which a blood glucose measurement apparatus corrects a user's blood glucose level based on a status of a user's autonomic nervous system, according to another exemplary embodiment.
Figure 17B:
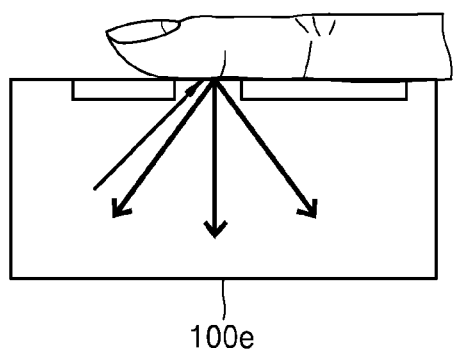

FIGS. 17A and 17B are diagrams for describing a method by which the blood glucose measurement apparatus 100d corrects a user's blood glucose level based on a status of a user's autonomic nervous system, according to another exemplary embodiment. The blood glucose measurement apparatus 100d may measure a user's blood glucose level by using optical characteristics of glucose.

A method of determining a user's blood glucose level by using optical methods may include infrared spectroscopy, Raman spectroscopy, optical coherence tomography (OCT), polarization, fluorescence, occlusion spectroscopy), and photoacoustic spectroscopy.

Referring to FIG. 17A, the infrared spectroscopy may be a method of measuring a concentration of glucose by using near infrared spectroscopy (NIR) having a wavelength of about 750 nm to about 2,000 nm or mid infrared spectroscopy (MIR) having a wavelength of about 2,500 to about 1,000 nm. For example, the blood glucose measurement apparatus 100d may irradiate NIR or MIR on an aqueous humor in a user's eyeball, measure an energy of a specific frequency emitted by collision of the irradiated NIR or MIR with glucose molecules, and calculate a concentration of glucose based on intensity of the measured energy.

Referring to FIG. 17B, the Raman spectroscopy may be a method of measuring a concentration of glucose by using characteristics of Raman spectrum of glucose.

The blood glucose measurement apparatus 100e may irradiate monochromatic light, such as a laser beam, on a user's finger. When the monochromatic light collides with various molecules in the body, the various molecules may become an excited state and then return to a ground state. In this case, the blood glucose measurement apparatus 100e may acquire spectrums of light emitted when the various molecules return from the excited state to the ground state. The blood glucose measurement apparatus 100e may measure a concentration of glucose based on intensity of light at a frequency at which Raman spectrum prominently appears among the acquired spectrums.

Even in the case of an optical blood glucose measurement method, the blood glucose measurement apparatus 100e may correct the measured blood glucose level based on the user's biometric information. Since the optical blood glucose measurement method measures a concentration of glucose by irradiating light on a body and analyzing light emitted from a material including glucose, it may be affected by a user's blood pressure, a user's body temperature, a humidity of a skin, a pulsatility of an artery, and an expansion of a blood vessel.

The blood glucose measurement apparatus 100e may acquire biometric information and correct the blood glucose level based on the acquired biometric information. For example, the blood glucose measurement apparatus 100e may receive information about a heart rate, a blood pressure, and a diameter of a blood vessel from a PPG sensor, receives a humidity of a skin from a GSR sensor, and correct a measured blood glucose level.

In addition, when it is impossible to acquire necessary biometric information, the blood glucose measurement apparatus 100e may determine a status of a user's autonomic nervous system from the acquired biometric information and acquire necessary biometric information based on the determined status of the user's autonomic nervous system.

For example, when the measured blood glucose level is affected by the galvanic skin response but it is impossible to acquire the galvanic skin response, the blood glucose measurement apparatus 100e may receive information about the heart rate, the blood pressure, and the diameter of the blood vessel from the PPG sensor, determine the status index of the autonomic nervous system from the received information about the heart rate, the blood pressure, and the diameter of the blood vessel, and determine the galvanic skin response from the status index of the autonomic nervous system. Therefore, the blood glucose measurement apparatus 100e may correct the measured blood glucose level based on the determined galvanic skin response.

Figure 18A:
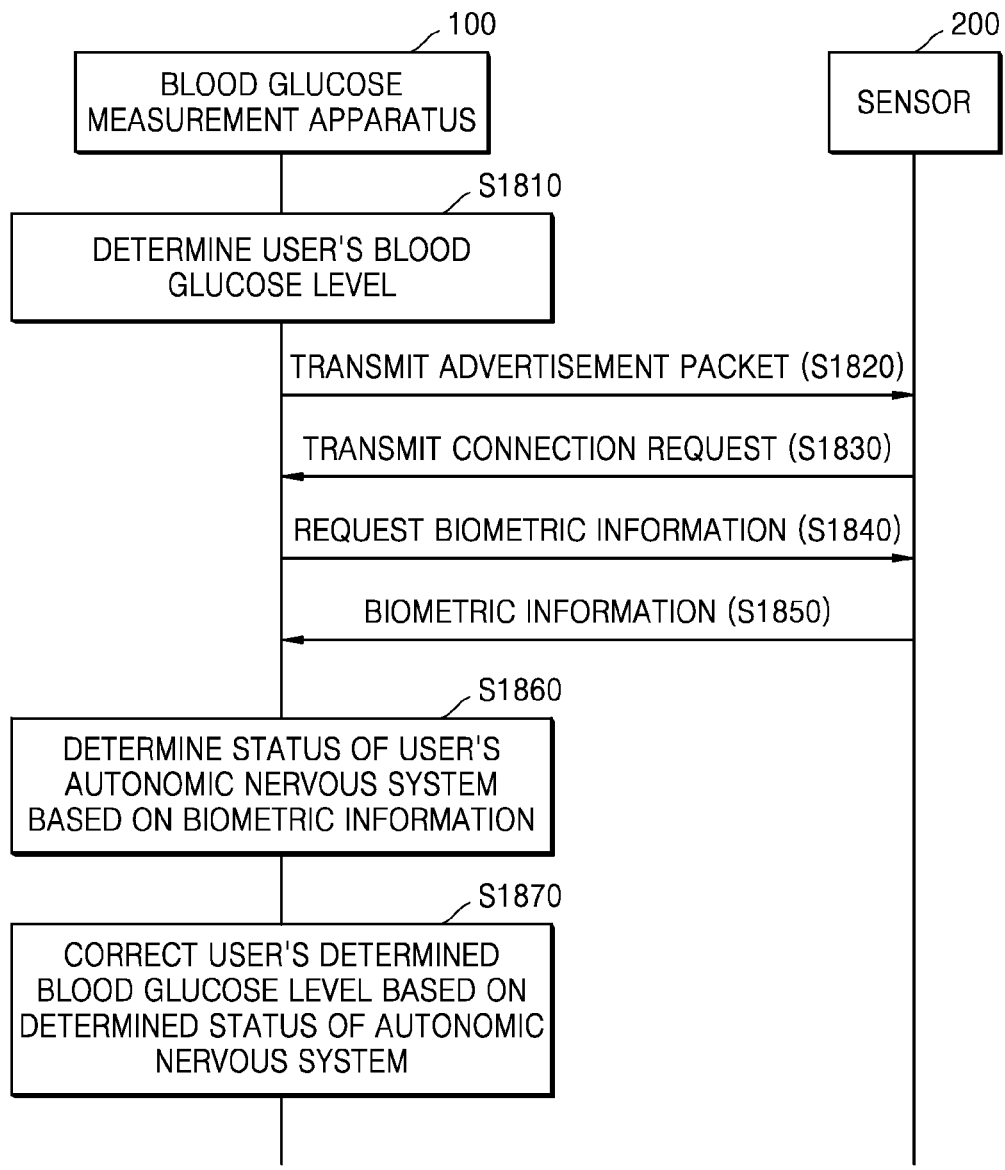
FIG. 18A is a flowchart of a method by which a blood glucose measurement apparatus receives biometric information from a sensor, according to an exemplary embodiment.

FIG. 18A is a flowchart of a method by which the blood glucose measurement apparatus 100 receives biometric information from the sensor 200, according to an exemplary embodiment.

In operation S1810, the blood glucose measurement apparatus 100 may determine a user's blood glucose level. The blood glucose measurement apparatus 100 may be a stationary measurement apparatus. When the blood glucose measurement apparatus 100 comes into contact with a body part of a user and receives a user's input of starting a blood glucose measurement, the blood glucose measurement apparatus 100 may measure a user's blood glucose level. The blood glucose measurement apparatus 100 may include an optical measurement apparatus, an electrochemical measurement apparatus, and a gas-type measurement apparatus.

In operation S1820, the blood glucose measurement apparatus 100 may transmit an advertisement packet. The blood glucose measurement apparatus 100 may include a Bluetooth beacon. When receiving the user's input of starting the blood glucose measurement, the blood glucose measurement apparatus 100 may broadcast an advertisement packet including identification information of the blood glucose measurement apparatus 100.

In operation S1830, the sensor 200 may transmit a connection request to the blood glucose measurement apparatus 100.

The sensor 200 may include a Bluetooth beacon. When receiving the advertisement packet transmitted by the blood glucose measurement apparatus 100, the sensor 200 may transmit a Bluetooth connection request to the blood glucose measurement apparatus 100 based on the identification information of the blood glucose measurement apparatus 100 which is included in the advertisement packet. The connection request may include a type of the sensor 200 and identification information of the sensor 200.

In operation S1840, the blood glucose measurement apparatus 100 may request biometric information from the sensor 200. The sensor 200 may be attached to a user's body and configured to measure the user's biometric information. The blood glucose measurement apparatus 100 may request the sensor 200 to transmit the biometric information measured by the sensor 200, based on the type of the sensor 200 which is received from the sensor 200. For example, when the sensor 200 is an ECG sensor 200b, the blood glucose measurement apparatus 100 may request information about a heart rate from the sensor 200.

In operation S1850, the sensor 200 may transmit the biometric information to the blood glucose measurement apparatus 100. The sensor 200 may transmit the user's biometric information to the blood glucose measurement apparatus 100.

In operation S1860, the blood glucose measurement apparatus 100 may determine the status of the user's autonomic nervous system based on the biometric information.

The status of the user's autonomic nervous system may include an activity degree of a user's sympathetic nerve and an activity degree of a user's parasympathetic nerve.

In operation S1870, the blood glucose measurement apparatus 100 may correct the determined blood glucose level based on the determined status of the user's autonomic nervous system. For example, the blood glucose measurement apparatus 100 may determine a secretion velocity of body fluid based on the activity degree of the use's sympathetic nerve. The secretion velocity of the body fluid based on the activity degree of the sympathetic nerve may be previously determined in the blood glucose measurement apparatus 100. When the secretion velocity of the body fluid is determined, the blood glucose measurement apparatus 100 may correct the determined blood glucose level based on the determined status of the user's autonomic nervous system.

Figure 18B:
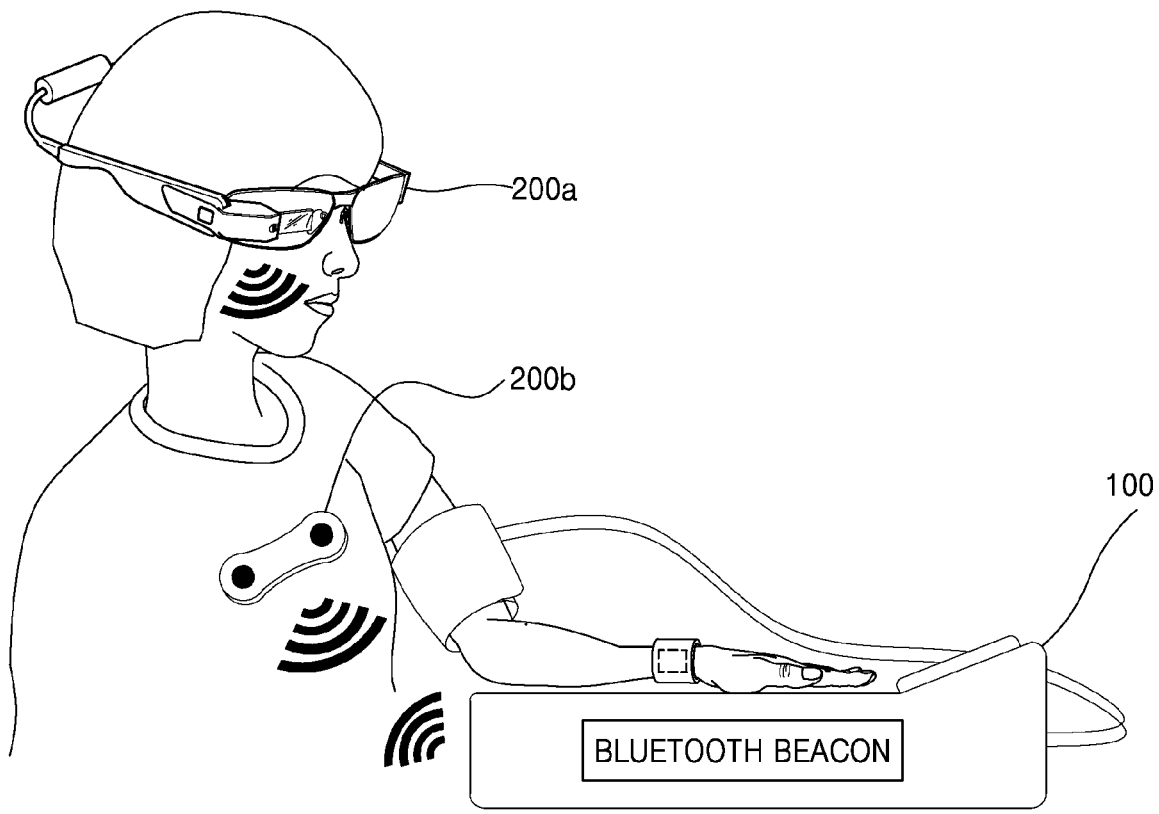
FIG. 18B is a diagram for describing a method by which a blood glucose measurement apparatus receives biometric information from a sensor when a user to whom the sensor is attached approaches the blood glucose measurement apparatus, according to an exemplary embodiment.

FIG. 18B is a diagram for describing a method by which the blood glucose measurement apparatus 100 receives biometric information from sensors 200 when a user to whom the sensors 200 (e.g., 200a and 200b) are attached approaches the blood glucose measurement apparatus 100, according to an exemplary embodiment.

Referring to FIG. 18B, the blood glucose measurement apparatus 100 and the sensors 200 may include a Bluetooth beacon function. The blood glucose measurement apparatus 100 may serve as an access point to periodically broadcast an advertisement packet.

When the user approaches to a preset range from the blood glucose measurement apparatus 100, the sensors 200 attached to the user may receive the advertisement packet from the blood glucose measurement apparatus 100. The advertisement packet may include a media access control (MAC) address of the blood glucose measurement apparatus 100.

When the MAC address is received from the blood glucose measurement apparatus 100, the sensors 200 may transmit a Bluetooth connection request to the blood glucose measurement apparatus 100 based on the MAC address of the blood glucose measurement apparatus 100. The Bluetooth connection request may include types of the sensors 200 and MAC addresses of the sensors 200.

The blood glucose measurement apparatus 100 may request the sensors 200 to transmit the user's biometric information, based on the types of the sensors 200 and the MAC addresses of the sensors 200 which are received from the sensors 200.

The blood glucose measurement apparatus 100 may determine the status of the user's autonomic nervous system based on the user's biometric information received from the sensors 200. The blood glucose measurement apparatus 100 may calculate a secretion velocity of a user's body fluid based on the determined status of the user's autonomic nervous system.

When the blood glucose measurement apparatus 100 comes into contact with the user and receives a user's input of starting a blood glucose measurement, the blood glucose measurement apparatus 100 may calculate the user's blood glucose level. In addition, the blood glucose measurement apparatus 100 may correct the calculated blood glucose level based on the determined secretion velocity of the body fluid.

Therefore, the blood glucose measurement apparatus 100 may receive the user's biometric information and correct the calculated blood glucose level based on the received biometric information.

Figure 19A:
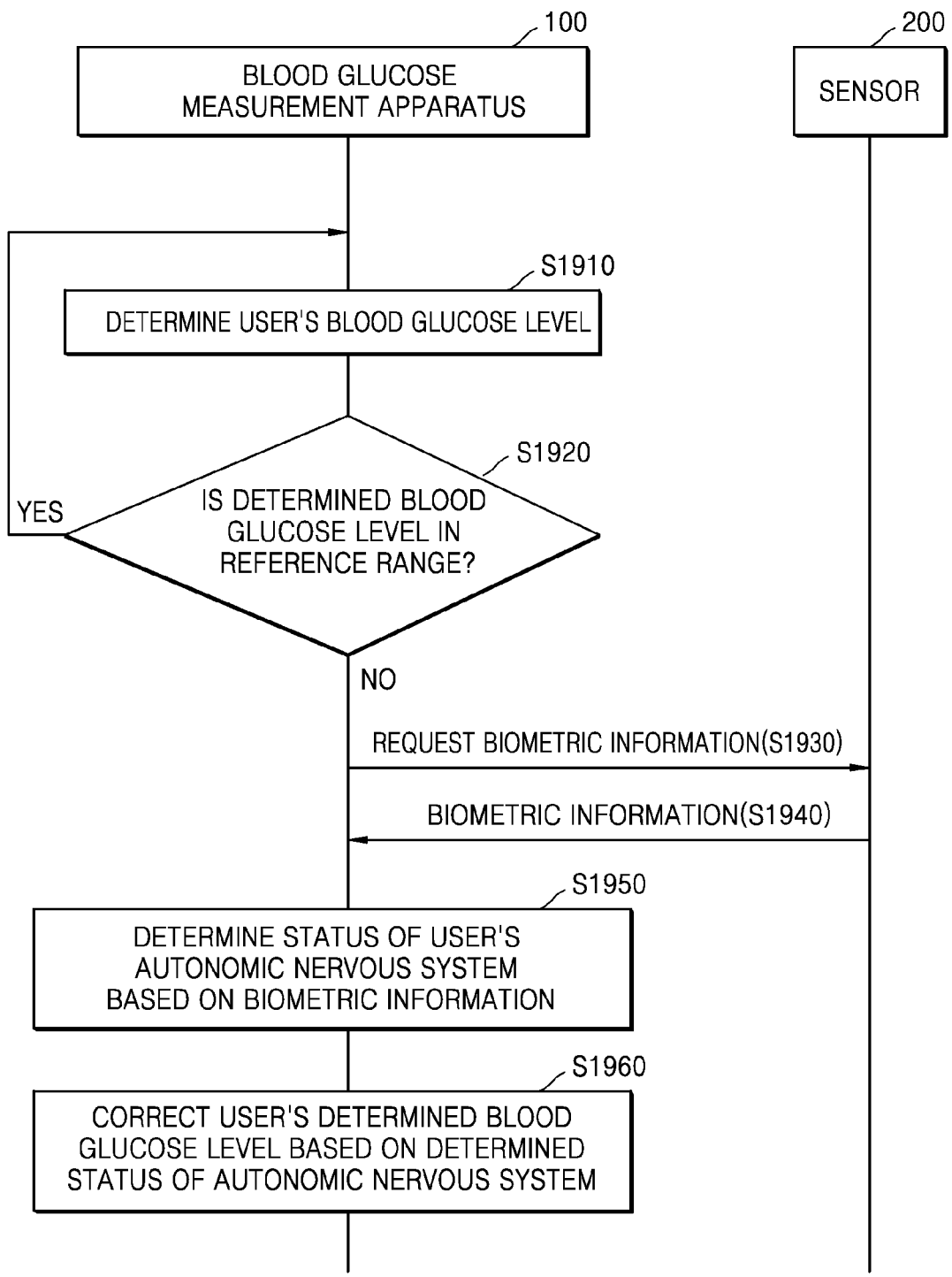
FIG. 19A is a flowchart of a method by which a blood glucose measurement apparatus receives biometric information from a sensor when a user's blood glucose level is out of a reference range, according to an exemplary embodiment.

FIG. 19A is a flowchart of a method by which the blood glucose measurement apparatus 100 receives biometric information from the sensor 200 when a user's blood glucose level is out of a reference range, according to an exemplary embodiment.

In operation S1910, the blood glucose measurement apparatus 100 may determine the user's blood glucose level.

The blood glucose measurement apparatus 100 may be a wearable apparatus that is attachable to a user's body. The blood glucose measurement apparatus 100 may periodically measure the user's blood glucose level. The blood glucose measurement apparatus 100 may include an optical measurement apparatus, an electrochemical measurement apparatus, and a gas-type measurement apparatus.

In operation S1920, the blood glucose measurement apparatus 100 may determine whether the determined blood glucose level is in the reference range.

The reference range of the blood glucose level may mean a normal blood glucose level of a person who is in a normal condition. For example, the reference range of the blood glucose level may be between about 80 mg/dL to about 160 mg/dL.

The reference range of the blood glucose level may be stored in the blood glucose measurement apparatus 100. For example, the blood glucose measurement apparatus 100 may receive a user's input of setting the reference range of the blood glucose level and store the received reference range of the blood glucose level. In addition, the blood glucose measurement apparatus 100 may receive the reference range of the blood glucose level from an external device.

When the measured blood glucose level is in the reference range, the blood glucose measurement apparatus 100 may measure the user's blood glucose level again after a preset time.

In operation S1930, when it is determined in operation S1920 that the determined blood glucose level is out of the reference range, the blood glucose measurement apparatus 100 may request biometric information from the sensor 200.

The identification information of the sensor 200 may be stored in the blood glucose measurement apparatus 100. For example, the blood glucose measurement apparatus 100 may receive a user's input of setting the sensor 200 as a Bluetooth node. When the user's input of setting the sensor 200 as the Bluetooth node is received, the blood glucose measurement apparatus 100 may receive the identification information of the sensor 200 from the sensor 200.

When the determined blood glucose level is out of the reference range, the blood glucose measurement apparatus 100 may request biometric information from at least one sensor 200 based on the identification information of the sensor 200 which is stored in the blood glucose measurement apparatus 100.

In operation S1940, the sensor 200 may transmit the biometric information to the blood glucose measurement apparatus 100.

The sensor 200 may transmit the measured biometric information to the blood glucose measurement apparatus 100. In this case, the sensor 200 may also transmit information about a type of the measured biometric information, a measured amount, and a measurement time to the blood glucose measurement apparatus 100.

In operation S1950, the blood glucose measurement apparatus 100 may determine the status of the user's autonomic nervous system based on the biometric information.

In operation S1960, the blood glucose measurement apparatus 100 may correct the determined blood glucose level based on the determined status of the user's autonomic nervous system.

Figure 19B:
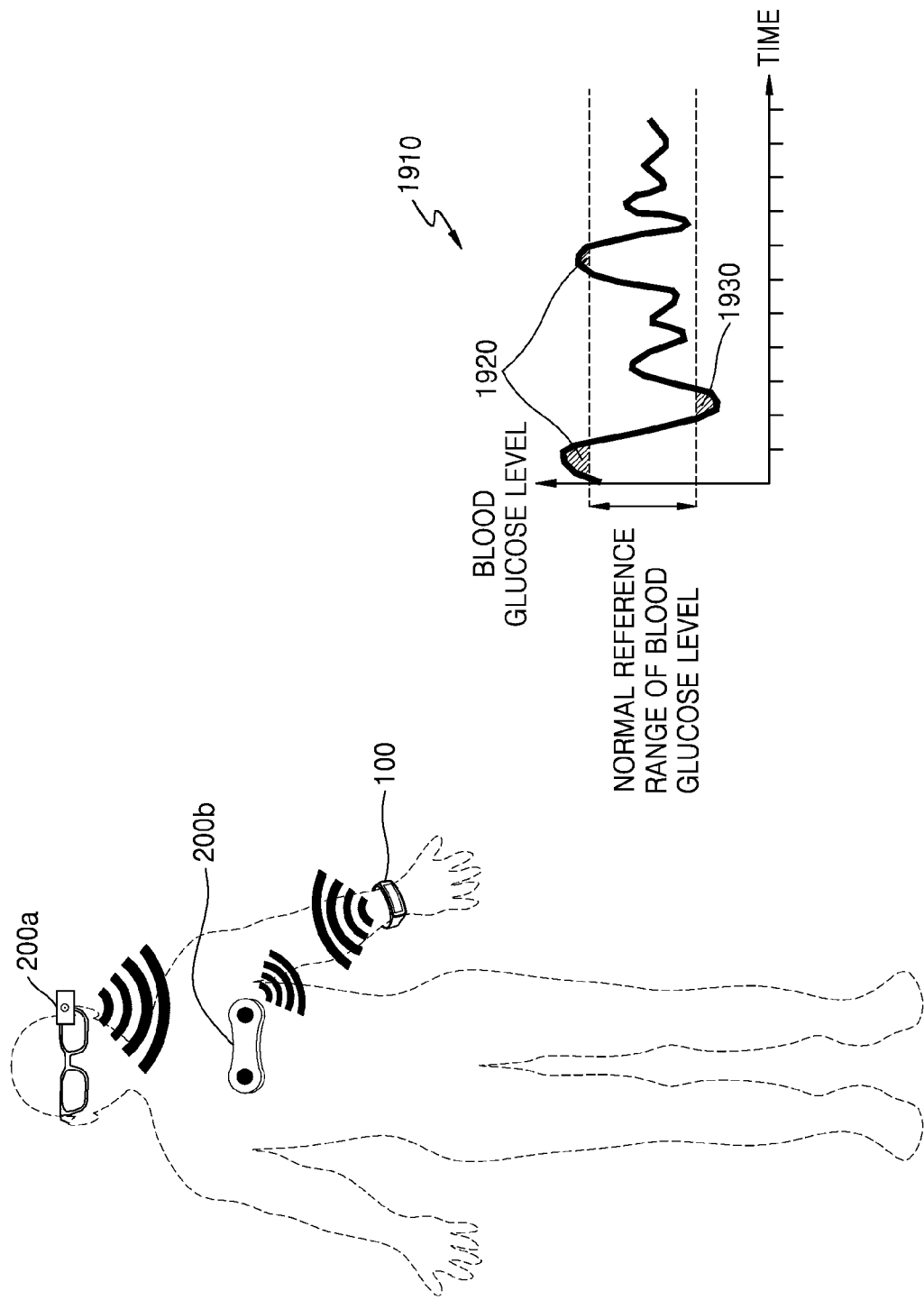
FIG. 19B is a diagram for describing a method by which a blood glucose measurement apparatus receives biometric information from a sensor when a user's blood glucose level is out of a reference range, according to an exemplary embodiment.

FIG. 19B is a diagram for describing a method by which the blood glucose measurement apparatus 100 receives biometric information from the sensor 200 when the user's blood glucose level is out of the reference range, according to an exemplary embodiment.

Referring to FIG. 19B, when the measured blood glucose level is out of a preset normal reference range, the blood glucose measurement apparatus 100 may collect a user's biometric information from the sensor 200.

A graph 1910 of FIG. 19B may be an example of a graph showing a user's blood glucose level measured for a day by the blood glucose measurement apparatus 100. As illustrated in FIG. 19B, the user's measured blood glucose level may be out of the normal reference range.

When the user's measured blood glucose level is out of the normal reference range, the blood glucose measurement apparatus 100 may request biometric information from at least one preset sensor 200. For example, when the user's measured blood glucose level enters a high blood glucose level range 1920 or a low blood glucose level range 1930, the blood glucose measurement apparatus 100 may request biometric information from at least one preset sensor 200.

When the request for the biometric information is received from the blood glucose measurement apparatus 100, the sensor 200 may measure the biometric information. For example, glasses 200a with a built-in camera may measure a size of a user's pupil and calculate a change in the size of the pupil. The glasses 200a with the built-in camera may transmit, to the blood glucose measurement apparatus 100, information indicating that the corresponding information is associated with the size of the pupil, information about the change in the size of the pupil, and information about the time for which the size of the pupil has been measured.

The blood glucose measurement apparatus 100 may correct the measured blood glucose level based on the biometric information received from the sensor 200. For example, the blood glucose measurement apparatus 100 may determine the status of the user's autonomic nervous system based on the size of the pupil, and correct the measured blood glucose level based on the determined status of the user's autonomic nervous system.

Figure 20A:
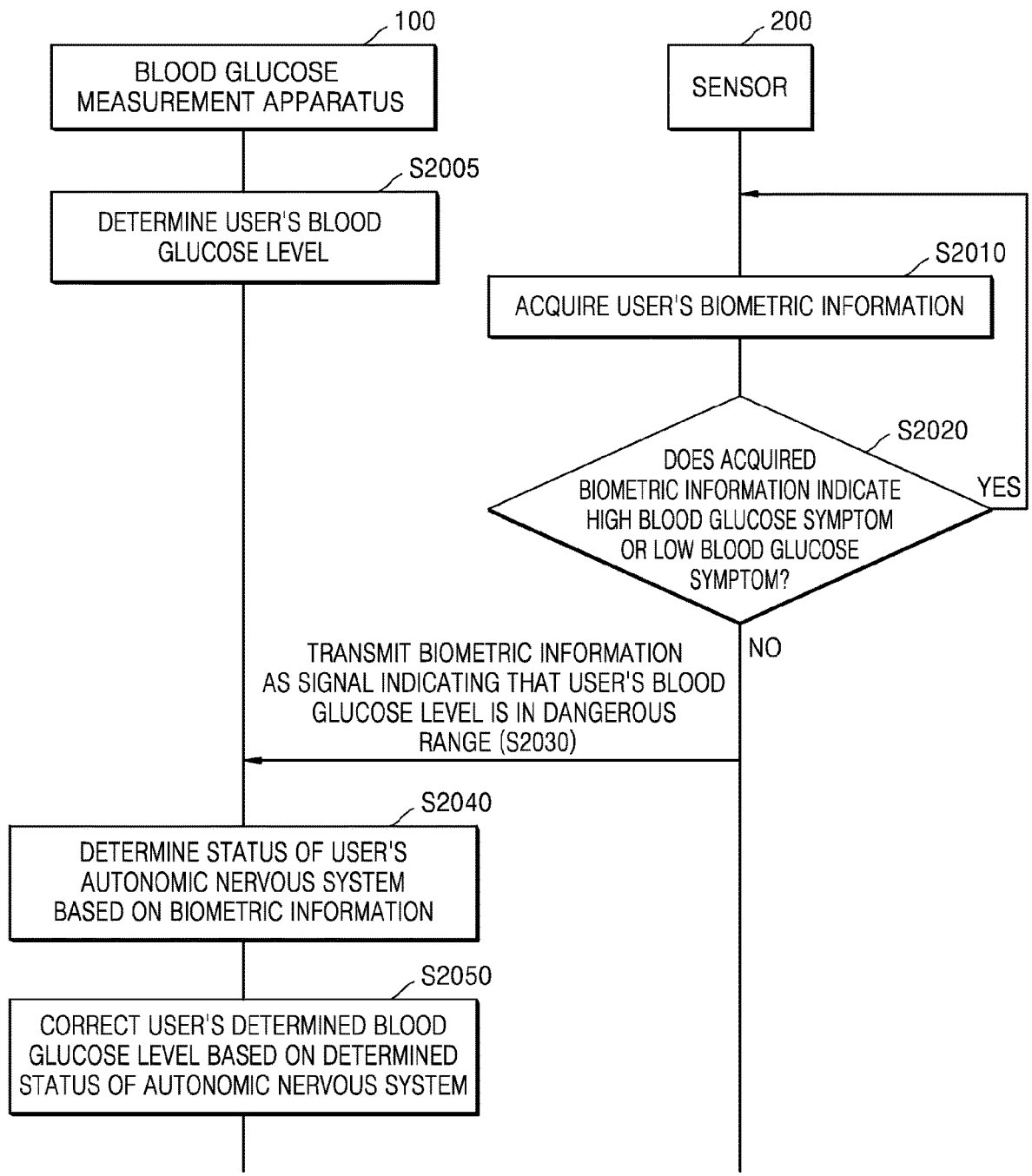
FIG. 20A is a flowchart of a method by which a blood glucose measurement apparatus receives biometric information from a sensor when biometric data indicates a high blood glucose symptom or a low blood glucose symptom, according to an exemplary embodiment.

FIG. 20A is a flowchart of a method by which a blood glucose measurement apparatus 100 receives biometric information from a sensor 200 when biometric data indicates a high blood glucose symptom or a low blood glucose symptom, according to an exemplary embodiment.

In operation S2005, the blood glucose measurement apparatus 100 may determine the user's blood glucose level.

The blood glucose measurement apparatus 100 may periodically measure the user's blood glucose level. The blood glucose measurement apparatus 100 may include an optical measurement apparatus, an electrochemical measurement apparatus, and a gas-type measurement apparatus.

In operation S2010, the sensor 200 may acquire user's biometric information.

The sensor 200 may be attached to a user's body. The sensor 200 may receive a user's biometric data from the user based on a preset period, and acquire a user's biometric information based on the received biometric data.

In operation S2020, the sensor 200 may determine whether the acquired biometric information indicates a high blood glucose symptom or a low blood glucose symptom. The sensor 200 may store a range of a normal blood glucose condition corresponding to biometric information to be measured. The range of the normal blood glucose condition may mean a range of biometric information which a body indicates when a user's blood glucose level is in a normal range. For example, the range of the normal blood glucose condition corresponding to the size of the pupil may mean the size range of the pupil when the user's blood glucose level is in a normal range.

When the acquired biometric information is out of the range of the normal blood glucose condition, the blood glucose measurement apparatus 100 may determine whether the acquired biometric information indicates a high blood glucose symptom or a low blood glucose symptom. When the acquired blood glucose level is in the range of the normal blood glucose condition, the sensor 200 may measure the user's biometric information again after a preset time.

In operation S2030, when it is determined in operation S2020 that the acquired biometric information is out of the range of the normal blood glucose condition, the sensor 200 may transmit biometric information to the blood glucose measurement apparatus 100 as a signal indicating that the user's blood glucose level is out of a normal range (e.g., a dangerous range).

The identification information of the blood glucose measurement apparatus 100 may be stored in the sensor 200.

When the acquired blood glucose level is out of the range of the normal blood glucose condition, the sensor 200 may transmit the acquired biometric information to the blood glucose measurement apparatus 100 based on the identification information of the blood glucose measurement apparatus 100. In this case, the sensor 200 may transmit information about a type of the measured biometric information, a measured amount, and a measurement time to the blood glucose measurement apparatus 100.

In operation S2040, the blood glucose measurement apparatus 100 may determine the status of the user's autonomic nervous system based on the biometric information. The status of the user's autonomic nervous system may include an activity degree of a user's sympathetic nerve and an activity degree of a user's parasympathetic nerve.

In operation S2050, the blood glucose measurement apparatus 100 may correct the determined blood glucose level based on the determined status of the user's autonomic nervous system. For example, the blood glucose measurement apparatus 100 may determine a secretion velocity of body fluid based on the activity degree of the use's sympathetic nerve. When the secretion velocity of the body fluid is determined, the blood glucose measurement apparatus 100 may correct the user's blood glucose level based on the secretion velocity of the body fluid.

Therefore, the blood glucose measurement apparatus 100 may receive the user's biometric information from the sensor 200, and also, when the user's blood glucose level is out of a normal range (e.g., a dangerous range). may receive the corresponding notification from the sensor 200.

Figure 20B:
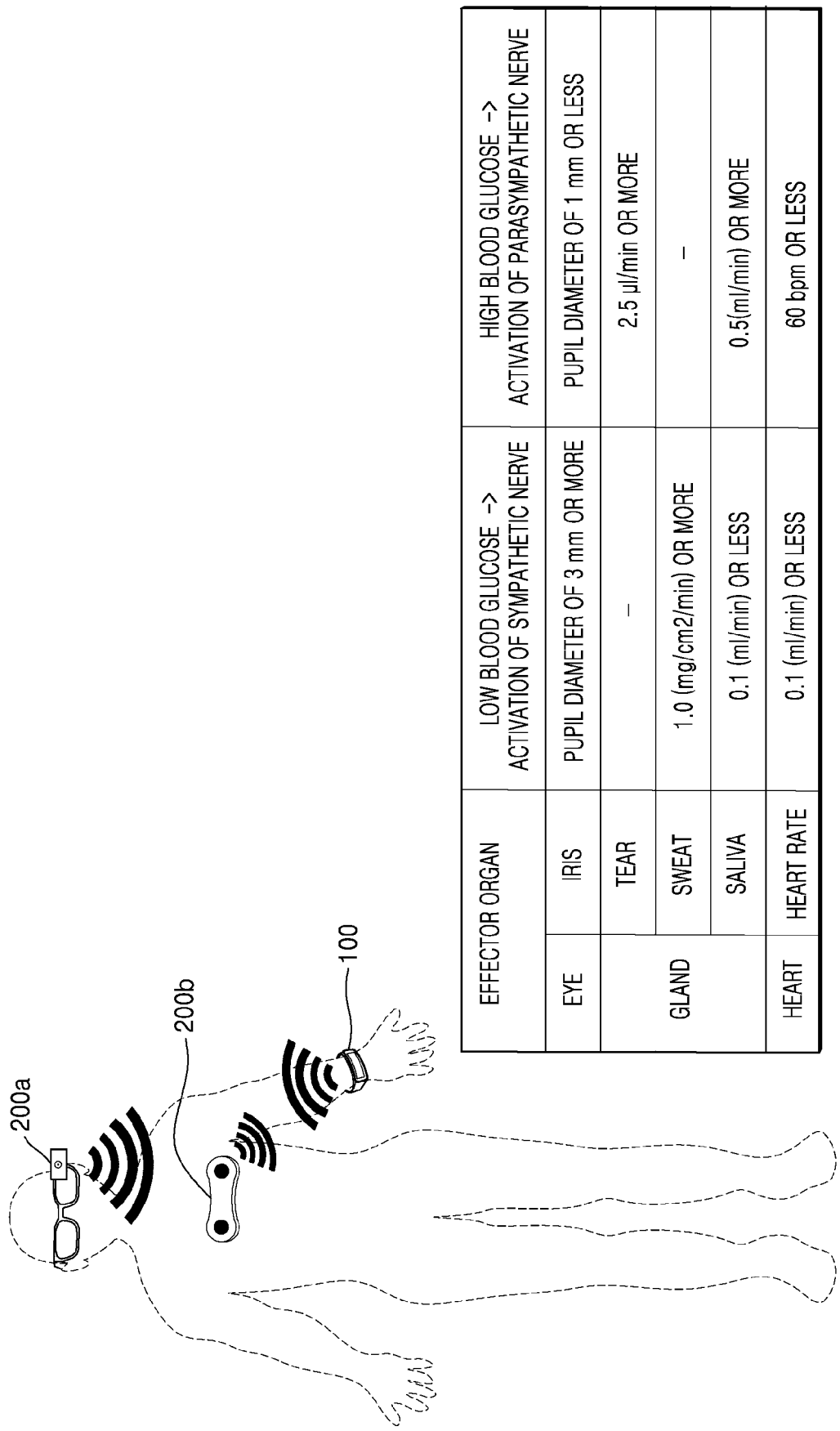
FIG. 20B is a diagram for describing a method by which a blood glucose measurement apparatus receives biometric information from a sensor when biometric data indicates a high blood glucose symptom or a low blood glucose symptom, according to an exemplary embodiment.

FIG. 20B is a diagram for describing a method by which the blood glucose measurement apparatus 100 receives biometric information from the sensor 200 when biometric data indicates a high blood glucose symptom or a low blood glucose symptom, according to another exemplary embodiment.

Referring to FIG. 20B, when the biometric data indicates a high blood glucose symptom or a low blood glucose symptom, the sensor 200 may transmit biometric information to the blood glucose measurement apparatus 100.

In a high blood glucose condition, a body may activate a parasympathetic nerve so as to maintain glucose homeostasis. Due to the activation of the parasympathetic nerve, glucose in a blood is stored as glycogen in a liver, reducing a blood glucose level in a body. In addition, in a low blood glucose condition, a body may activate a sympathetic nerve so as to maintain glucose homeostasis. Due to the activation of the sympathetic nerve, glycogen is converted into glucose in a liver. The glucose is discharged into a blood, increasing a blood glucose level.

When the sympathetic nerve or the parasympathetic nerve is activated, body organs may exhibit the effects according to the activation of the sympathetic nerve or the parasympathetic nerve. For example, the activation of the sympathetic nerve may expand the pupil, accelerate the secretion of the sweat, and increase the heart rate. A degree of a change occurring in the body organs may be determined according to an activity degree of the sympathetic nerve or the parasympathetic nerve.

Therefore, the sensor 200 may determine a high blood glucose symptom or a low blood glucose symptom based on the degree of the change in the body organs. For example, referring to a table of FIG. 20B, a range of biometric data that is exhibited in a high blood glucose condition or a low blood glucose condition may be stored in the sensor 200. When the measured range of the biometric data indicates the high blood glucose symptom or the low blood glucose symptom, the sensor 200 may transmit biometric information to the blood glucose measurement apparatus 100 as a signal indicating that the user's blood glucose level is in the dangerous range.

For example, a heart rate sensor 200b may periodically measure a user's heart rate. When the heart rate is 120 bpm or more, the heart rate sensor 200b may transmit, to the blood glucose measurement apparatus 100, information indicating that the user shows a low blood glucose symptom and a measured heart rate.

Figure 21A:
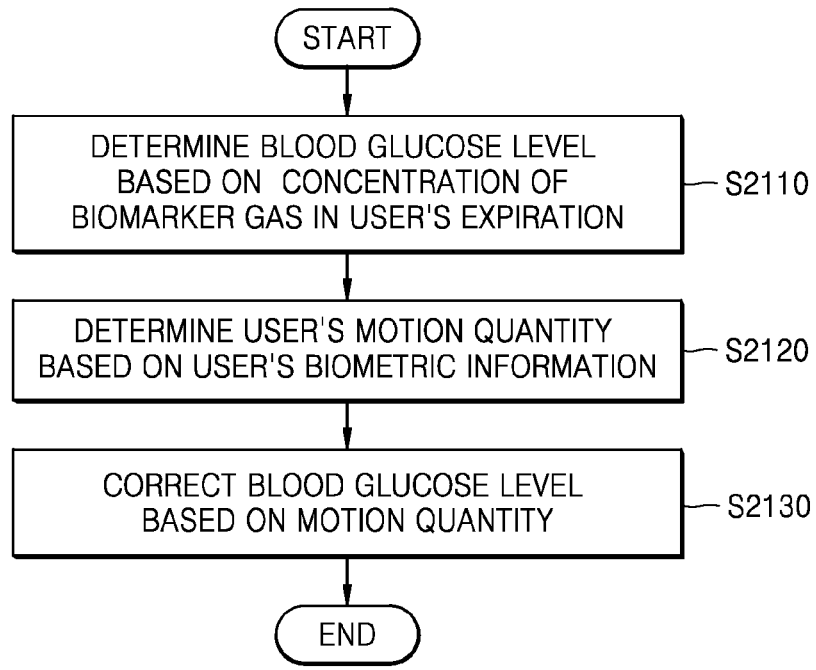
FIGS. 21A and 21B are respectively a flowchart and a diagram for describing a method by which a blood glucose measurement apparatus corrects a user's blood glucose level based on a motion quantity, according to an exemplary embodiment.
Figure 21B:
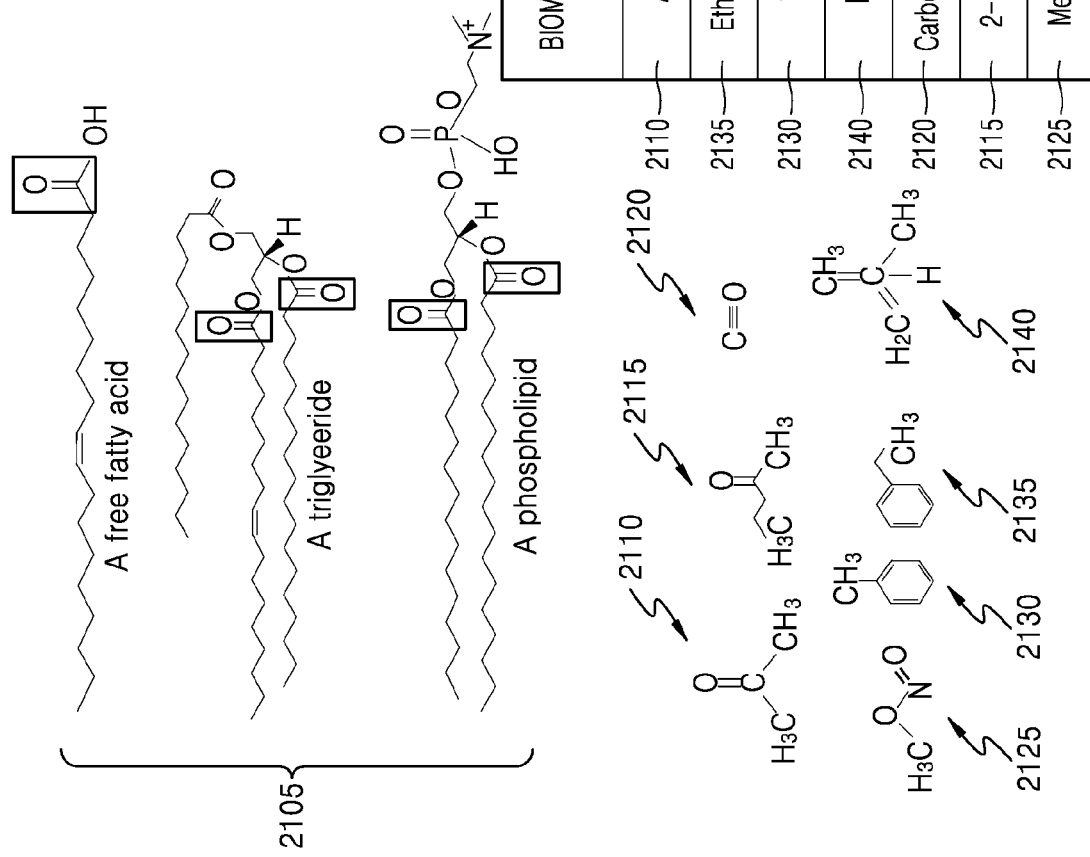

FIGS. 21A and 21B are respectively a flowchart and a diagram for describing a method by which the blood glucose measurement apparatus 100 corrects a user's blood glucose level based on a motion quantity, according to an exemplary embodiment.

In operation S2110, the blood glucose measurement apparatus 100 may measure the user's blood glucose level based on a concentration of biomarker gas in a user's expiration.

The biomarker gas indicating the blood glucose level may be a gas component whose concentration discharged through expiration is changed according to the blood glucose level among a plurality of gas components included in the expiration. The biomarker gas indicating the blood glucose level may be a gas component that is discharged through expiration when a body fat 2105 is decomposed.

For example, referring to FIG. 21B, since cells in the body cannot absorb glucose in a high blood glucose condition, body fat instead of glucose may be used as energy source. Since a fat is incompletely burnt, gas such as acetone may be generated when the body fat 2105 is decomposed. Therefore, when the blood glucose level in the body increases, the biomarker gas indicating the blood glucose level may be more discharged.

The biomarker gas indicating the blood glucose level may include acetone 2110, 2-pentanone 2115, carbon monoxide 2120, methyl nitrate 2125, toluene 2130, ethyl benzene 2135, and isoprene 2140, but is not limited thereto.

The blood glucose measurement apparatus 100 may measure a concentration of the biomarker gas and determine a blood glucose level based on the measured concentration of the biomarker gas. For example, the blood glucose level based on the concentration of the biomarker gas may be expressed as Formula 4 below.

$$\text{Glucose\_Blood} = d * \text{BiomarkerGas\_Concentration} \quad (4)$$

In Formula 4, "BiomarkerGas_Concentration" may mean the concentration of the biomarker gas in expiration. In addition, "Glucose_Blood" may mean the user's blood glucose level when user's motion quantity is below a reference. For example, "Glucose_Blood" may mean a blood glucose level in a blood, which is measured in an invasive manner in a state in which there is almost no movement of the user.

A coefficient "d" indicating a correlation between the concentration of the biomarker gas and the blood glucose level may be calculated by regression analysis. For example, the coefficient "d" indicating the correlation between the concentration of the biomarker gas and the blood glucose level may be calculated by measuring the blood glucose level in the blood in an invasive manner, assuming the measured blood glucose level as "Glucose_Blood", measuring the concentration of the biomarker gas in the expiration, and setting the measured concentration of the biomarker gas as "BiomarkerGas_Concentration".

In operation S2120, the blood glucose measurement apparatus 100 may determine the user's motion quantity based on the user's biometric information. The blood glucose measurement apparatus 100 may measure a user's biometric information indicating the user's motion quantity by using the sensor 200 provided therein. In addition, the blood glucose measurement apparatus 100 may measure the user's motion quantity by receiving the user's biometric information from the sensor 200 configured to measure the user's motion quantity.

The blood glucose measurement apparatus 100 may store a method of determining the user's motion quantity by using at least one piece of the biometric information as a variable. For example, the method of determining the user's motion quantity by using at least one piece of the biometric information as a variable may be expressed as Formula 5 below.

$$\text{Motion\_quantity} = 1/n * \Sigma [e_n * \text{Body\_data}_n] \quad (5)$$

In Formula 5, "Motion_quantity" may mean a user's motion quantity. "Body_data$_n$" may mean biometric information indicating the user's motion quantity. For example, the biometric information indicating the user's motion quantity may include a body temperature, a step count, a heart rate, and an amount of sweat.

"$e_n$" may be a coefficient indicating an influence of the biometric information on the user's motion quantity. "$e_n$" may be different for each user in a reference range. In addition, "$e_n$" may be determined by regression analysis. "$e_n$" may be experimentally measured and prestored and may be updated according to a user's condition.

The sensor 200 configured to measure the user's motion quantity may include a thermometer 200e, a pedometer 200f, an ECG sensor 200b, a PPG sensor 200d, a GSR sensor 200c, and a global positioning system (GPS) sensor 200g.

When the biometric information indicating the user's motion quantity is received, the blood glucose measurement apparatus 100 may measure the user's motion quantity based on the received biometric information. For example, it may be determined that the user's motion quantity is higher as the heart rate is higher, the amount of sweat is larger, and the body temperature is higher.

In operation S2130, the blood glucose measurement apparatus 100 may correct the blood glucose level based on the determined motion quantity.

The biomarker gases in the expiration, the concentration of which increases as the blood glucose level increases, may increase as the motion quantity increases. The body may use a fat as energy source. Since a fat is incompletely burnt, gas such as acetone may be generated when the fat is decomposed. As the motion quantity increases, the body may burn a larger amount of body fat, thus discharging a larger amount of the biomarker gas.

The blood glucose measurement apparatus 100 may correct the blood glucose level by determining an amount of the biomarker gas discharged by the motion with respect to the entire amount of the biomarker gas in the expiration, based on the determined motion quantity. A correlation between the motion quantity and the blood glucose level may be expressed as Formula 6 below.

$$\text{Glucose\_Blood} = \text{Glucose\_measure} - f * \text{Motion\_quantity} \quad (6)$$

In Formula 5, "Glucose_Blood" may mean the user's blood glucose level corrected based on the motion quantity. In addition, "Glucose_measure" may mean the blood glucose level measured by the blood glucose measurement apparatus 100. "Motion_quantity" may mean the motion quantity measured by the blood glucose measurement apparatus 100.

A coefficient "f" indicating the correlation between the motion quantity and the blood glucose level may be calculated by regression analysis. For example, the coefficient "f" may be calculated by measuring the blood glucose level in the blood in an invasive manner (assuming the measured blood glucose level as "Glucose_Blood") measuring the blood glucose level based on the concentration of the biomarker gas in the expiration, setting the measured blood glucose level as "Glucose_measure", and setting the calculated motion quantity as "Motion_quantity".

Figure 22A:
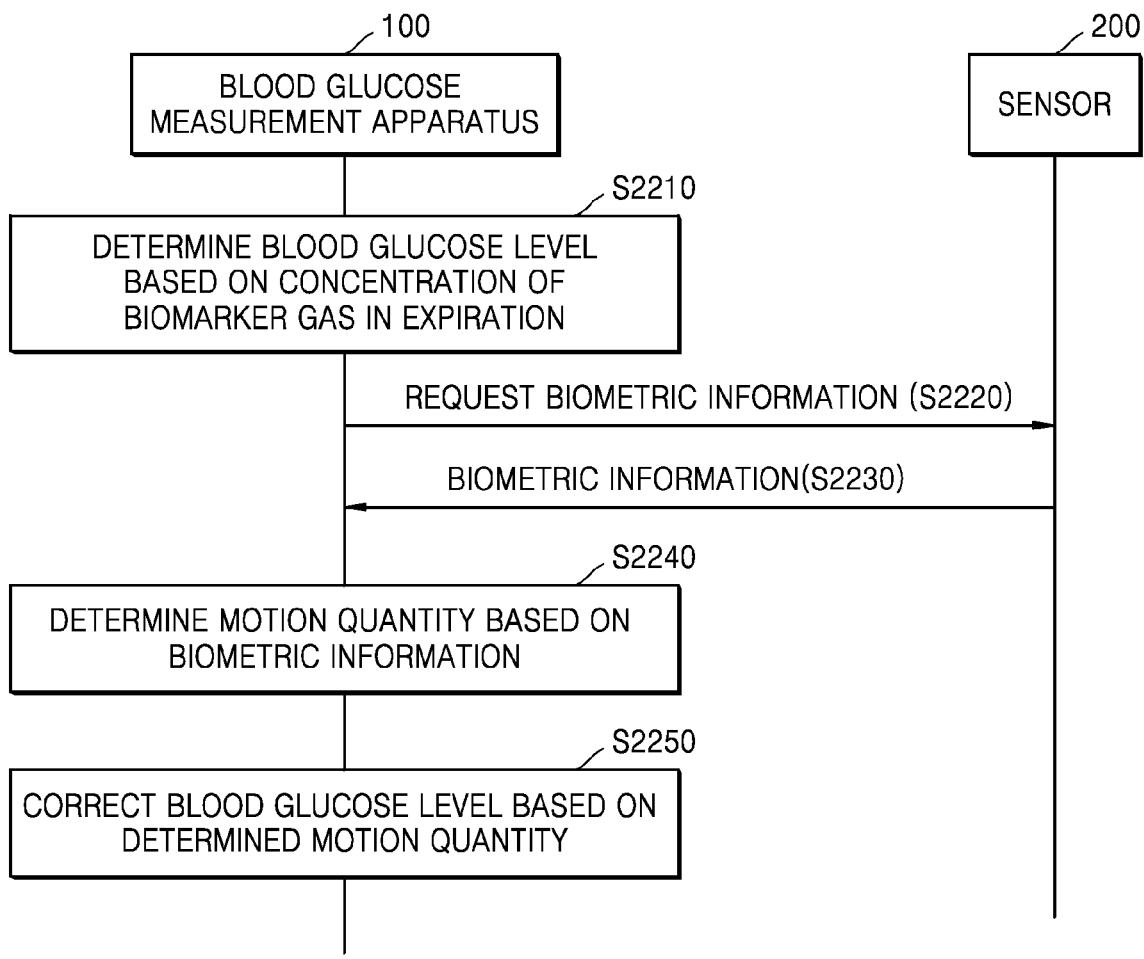
FIG. 22A is a flowchart of a method by which a blood glucose measurement apparatus corrects a blood glucose level measured based on a biomarker gas, based on a user's motion quantity, according to an exemplary embodiment.

FIG. 22A is a flowchart of a method by which a blood glucose measurement apparatus 100 corrects a blood glucose level measured based on a biometric marker gas, based on a user's motion quantity, according to an exemplary embodiment.

In operation S2210, the blood glucose measurement apparatus 100 may determine a user's blood glucose level based on a concentration of biomarker gas in a user's expiration.

The biomarker gas may be a gas component whose concentration discharged through the expiration is changed according to the blood glucose level among a plurality of gas components included in the expiration. The blood glucose measurement apparatus 100 may measure the concentration of the biomarker gas and determine the blood glucose level based on the measured concentration of the biomarker gas.

In operation S2220, the blood glucose measurement apparatus 100 may request biometric information from the sensor 200.

The identification information of the sensor 200 may be stored in the blood glucose measurement apparatus 100. The blood glucose measurement apparatus 100 may request biometric information from the sensor 200 by using a short-range wireless communication method.

In operation S2230, the sensor 200 may transmit the biometric information to the blood glucose measurement apparatus 100. The sensor 200 may transmit the measured biometric information to the blood glucose measurement apparatus 100. In this case, the sensor 200 may also transmit information about a type of the measured biometric information, a measured amount, and a measurement time to the blood glucose measurement apparatus 100.

In operation S2240, the blood glucose measurement apparatus 100 may determine the user's motion quantity based on the user's biometric information. The blood glucose measurement apparatus 100 may calculate the user's motion quantity based on the biometric information. The correlation between the biometric information and the motion quantity may previously determined in the blood glucose measurement apparatus 100. For example, the motion quantity may be determined in proportion to the size of the biometric information.

In operation S2250, the blood glucose measurement apparatus 100 may correct the blood glucose level based on the determined motion quantity. Components in the expiration gas, the concentration of which increases as the blood glucose level increases, may increase as the motion quantity increases. Therefore, the blood glucose measurement apparatus 100 may correct the blood glucose level based on the motion quantity.

Figure 22B:
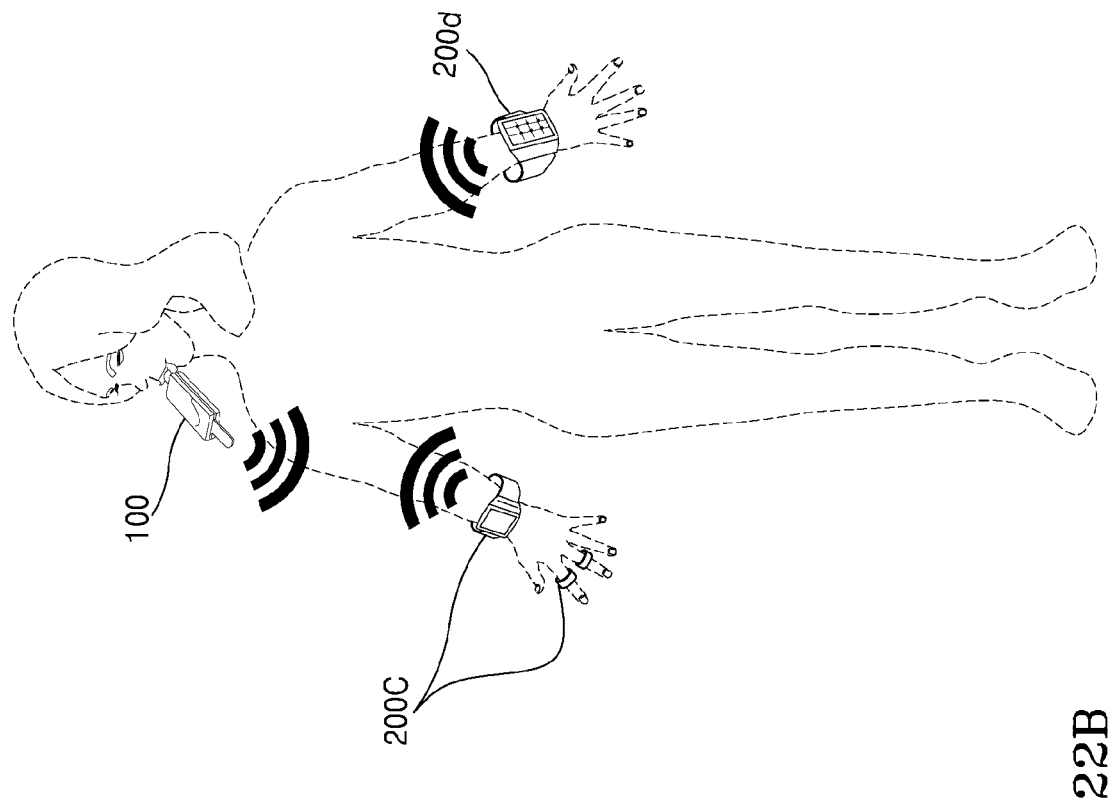
FIG. 22B is a diagram for describing a method by which a blood glucose measurement apparatus corrects a blood glucose level measured based on a motion quantity, according to an exemplary embodiment.
Figure 22B:
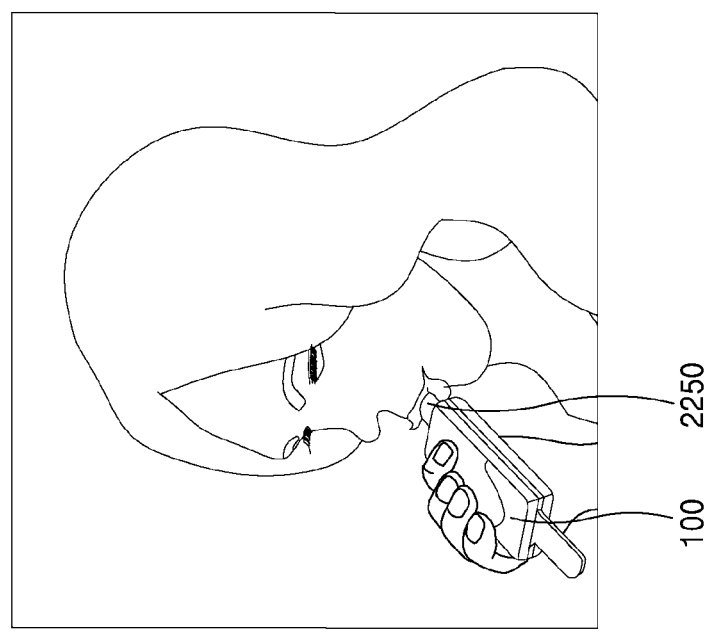

FIG. 22B is a diagram for describing a method by which the blood glucose measurement apparatus 100 corrects the blood glucose level measured based on the motion quantity, according to an exemplary embodiment.

Referring to FIG. 22B, the blood glucose measurement apparatus 100 may correct the blood glucose level measured based on the biomarker gas, based on the user's motion quantity.

For example, the blood glucose measurement apparatus 100 may include a collection member 2250 configured to collect the user's expiration. When the user blows the expiration into the collection member 2250, the blood glucose measurement apparatus 100 may measure a concentration of acetone in the expiration. Generally, 900 ppb of acetone gas may be included in an expiration of a person who is in a normal condition, and 1,800 ppb of acetone gas may be included in an expiration of a diabetic patient.

In addition, the blood glucose measurement apparatus 100 may include an adsorption member configured to adsorb acetone molecules in the expiration. When the acetone molecules in the user's expiration are adsorbed on the adsorption member, the blood glucose measurement apparatus 100 may calculate a concentration of acetone based on a change in a resistance of the adsorption member.

The blood glucose measurement apparatus 100 may measure the user's motion quantity based on the biometric information and correct the measured blood glucose level based on the measured motion quantity. For example, the blood glucose measurement apparatus 100 may receive information about a heart rate from the PPG sensor 200d attached to the user's body, receive information about a secreted amount of sweat from the GSR sensor 200c, and receive information about a motion quantity per unit time from the pedometer 200f. The blood glucose measurement apparatus 100 may determine a degree of the user's motion quantity based on the received information about the heart rate data, the secreted amount of the sweat, or the motion quantity per unit time.

The blood glucose measurement apparatus 100 may correct the measured blood glucose level based on the determined degree of the motion quantity. For example, when the user's motion quantity is high, the blood glucose measurement apparatus 100 may determine that a concentration of acetone in expiration is increased due to the motion as well as the blood glucose level, and reduce the measured blood glucose level.

Figure 23A:
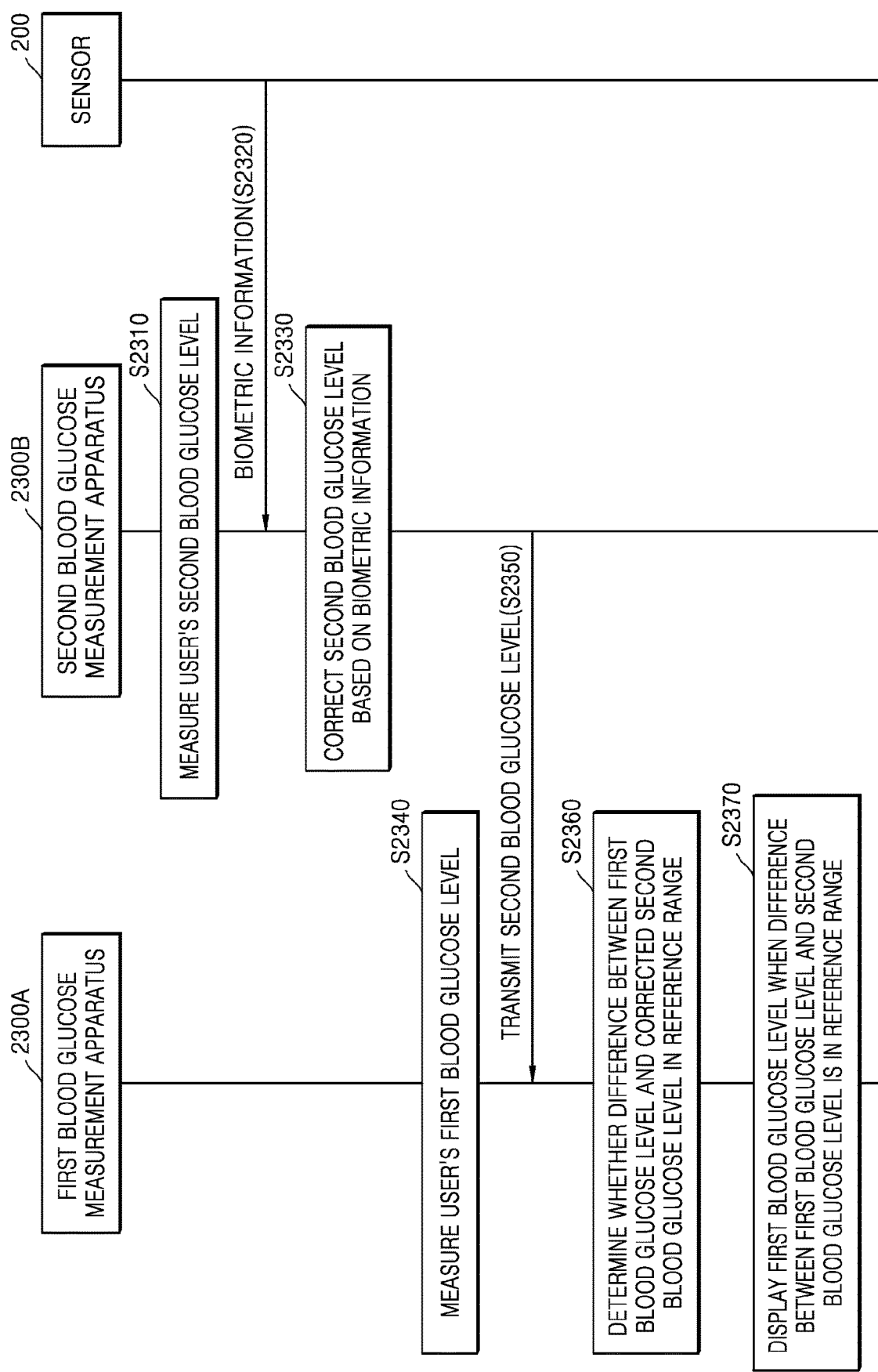
FIG. 23A is a flowchart of a method by which a first blood glucose measurement apparatus determines a user's blood glucose level based on a blood glucose level measured by a second blood glucose measurement apparatus, according to an exemplary embodiment.

FIG. 23A is a flowchart of a method by which a first blood glucose measurement apparatus 2300a determines a user's blood glucose level based on a blood glucose level measured by a second blood glucose measurement apparatus 2300b, according to an exemplary embodiment.

In operation S2310, the second blood glucose measurement apparatus 2300b may measure a user's second blood glucose level. The second blood glucose measurement apparatus 2300b may be an electrochemical blood glucose measurement apparatus. The electrochemical blood glucose measurement apparatus may be configured to measure the user's blood glucose level based on a concentration of glucose in secretions, such as sweat, tear, and saliva, which are discharged from a user's body.

In addition, the second blood glucose measurement apparatus 2300b may be the blood glucose measurement apparatus 100 configured measure the user's blood glucose level based on the concentration of the biomarker gas in the user's expiration.

In operation S2320, the second blood glucose measurement apparatus 2100b may receive biometric information from a sensor 200.

For example, the sensor 200 may transmit the measured biometric information to the second blood glucose measurement apparatus 2300b, based on a preset period.

In operation S2330, the second blood glucose measurement apparatus 2300b may correct the second blood glucose level based on biometric information.

The second blood glucose measurement apparatus 2300b may correct the measured second blood glucose level based on biometric information received from the sensor 200.

For example, the second blood glucose measurement apparatus 2300b may determine a status of a user's autonomic nervous system based on the biometric information. The status of the user's autonomic nervous system may include an activity degree of a user's sympathetic nerve and an activity degree of a user's parasympathetic nerve. In addition, when the status of the user's autonomic nervous system is determined, the second blood glucose measurement apparatus 2300b may determine a secretion velocity of body fluid based on the determined status of the user's autonomic nervous system. For example, the second blood glucose measurement apparatus 2300b may determine the secretion velocity of the body fluid based on the activity degree of the use's sympathetic nerve. The secretion velocity of the body fluid based on the activity degree of the sympathetic nerve may be previously determined in the second blood glucose measurement apparatus 2300b. In addition, when the secretion velocity of the body fluid is determined, the blood glucose measurement apparatus 100 may correct the second blood glucose level measured based on the concentration of glucose in the secretions, based on the secretion velocity of the body fluid.

In addition, for example, the second blood glucose measurement apparatus 2300b may determine a user's motion quantity based on the biometric information. When the user's motion quantity is determined, the second blood glucose measurement apparatus 2300b may correct the second blood glucose level measured based on the concentration of the biomarker gas in the user's expiration, based on the determined motion quantity.

In operation S2340, the first blood glucose measurement apparatus 2300a may measure a user's first blood glucose level.

The first blood glucose measurement apparatus 2300a may be an electrochemical blood glucose measurement apparatus. The electrochemical blood glucose measurement apparatus may be configured to measure a concentration of glucose by using optical characteristics of glucose in a body.

For example, the first blood glucose measurement apparatus 2300a may irradiate light on a body and calculate a concentration of a glucose component among glucose, albumin, RBC, collagen, and water in a body, based on a change in intensity of the light according to a frequency of reflected light.

The first blood glucose measurement apparatus 2300a may measure the blood glucose level once and determine the measured blood glucose level as the user's blood glucose level. In addition, the first blood glucose measurement apparatus 2300a may measure the blood glucose levels two or more times and determine an average value of the measured blood glucose levels as the user's blood glucose level only when a standard deviation of the measured blood glucose levels is in a reference range. For example, the first blood glucose measurement apparatus 2300a may measure the blood glucose levels five or more times within a preset time and determine an average value of the five measured blood glucose levels as the user's blood glucose level only when a standard deviation of the measured blood glucose levels is within 5%.

In operation S2350, the second blood glucose measurement apparatus 2300b may transmit the corrected second blood glucose level to the first blood glucose measurement apparatus 2300a.

When a request for the blood glucose level is received from the first blood glucose measurement apparatus 2300a, the second blood glucose measurement apparatus 2300b may transmit the blood glucose level to the first blood glucose measurement apparatus 2300a. In addition, when the measured second blood glucose level is out of the reference range, the second blood glucose measurement apparatus 2300b may transmit the second blood glucose level to the first blood glucose measurement apparatus 2300a.

In operation S2360, the first blood glucose measurement apparatus 2300a may determine whether a difference between the first blood glucose level and the corrected second blood glucose level is in the reference range.

For example, the first blood glucose measurement apparatus 2300a may determine whether the difference between the first blood glucose level measured by the optical method and the second blood glucose level measured by the electrochemical method or the method using the concentration of the biomarker gas in the expiration is within 10%.

In operation S2370, the first blood glucose measurement apparatus 2300a may display the first blood glucose level when the difference between the first blood glucose level and the second blood glucose level is in the reference range.

For example, when the difference between the first blood glucose level measured by the optical method and the second blood glucose level measured by the electrochemical method or the method using the concentration of the biomarker gas in the expiration is within 10%, the first blood glucose measurement apparatus 2300a may determine the first blood glucose level measured by the optical method as the user's blood glucose level and display the first blood glucose level.

Therefore, it is possible to calculate the user's blood glucose level more accurately by using the biometric information and to further improve the accuracy of the blood glucose level by using a plurality of blood glucose measurement apparatuses 100.

Figure 23B:
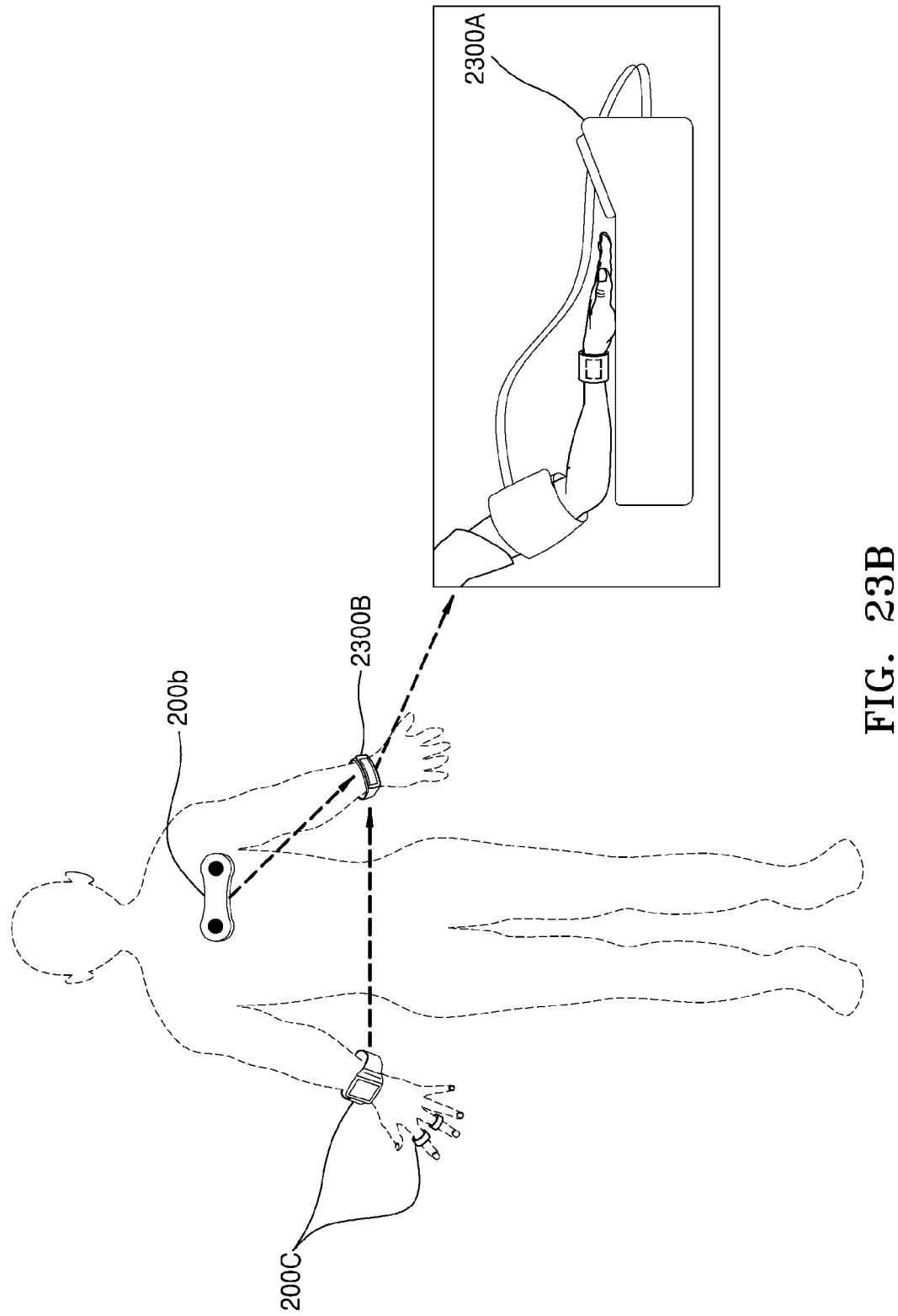
FIG. 23B is a diagram for describing a method by which a first blood glucose measurement apparatus determines a user's blood glucose level based on a blood glucose level measured by a second blood glucose measurement apparatus, according to an exemplary embodiment.

FIG. 23B is a diagram for describing a method by which the first blood glucose measurement apparatus 2300a determines the user's blood glucose level based on the blood glucose level measured by the second blood glucose measurement apparatus 2300b, according to an exemplary embodiment.

Referring to FIG. 23B, the first blood glucose measurement apparatus 2300a may determine the user's blood glucose level based on the blood glucose level measured by the second blood glucose measurement apparatus 2300b.

When a plurality of blood glucose measurement apparatuses capable of measuring the user's blood glucose level are provided, the reliability of the measured blood glucose level may be increased as a difference between blood glucose levels measured by the plurality of blood glucose measurement apparatuses is smaller.

Accordingly, the first blood glucose measurement apparatus 2300a may determine the reliability of the blood glucose level measured by the first blood glucose measurement apparatus 2300a by receiving the blood glucose levels measured by the second blood glucose measurement apparatuses 2300b and comparing the received blood glucose levels with the blood glucose level measured by the first blood glucose measurement apparatus 2300a. When the reliability of the blood glucose level measured by the first blood glucose measurement apparatus 2300a is a reference level or more, the first blood glucose measurement apparatus 2300a may determine the blood glucose level measured by the first blood glucose measurement apparatus 2300a as the user's blood glucose level.

The blood glucose level to be determined as the user's blood glucose level, which is measured by the first blood glucose measurement apparatus 2300a, may be a blood glucose level measured by the optical method. In addition, the blood glucose level, which is measured by the second blood glucose measurement apparatus 2300b so as to determine the reliability, may be a blood glucose level measured by the electrochemical method or the method using the expiration gas.

The second blood glucose measurement apparatus 2300b may measure a user's second blood glucose level. The second blood glucose measurement apparatus 2300b may receive biometric information from the sensor 200. The second blood glucose measurement apparatus 2300b may correct the measured second blood glucose level based on the biometric information received from the sensor 200.

The second blood glucose measurement apparatus 2300b may transmit the corrected second blood glucose level to the first blood glucose measurement apparatus 2300a. The first blood glucose measurement apparatus 2300a may determine whether a difference between the first blood glucose level and the corrected second blood glucose level is in the reference range. When the difference between the first blood glucose level and the second blood glucose level is in the reference range, the first blood glucose measurement apparatus 2300a may determine the first blood glucose level as the user's blood glucose level and display the first blood glucose level.

Figure 24A:
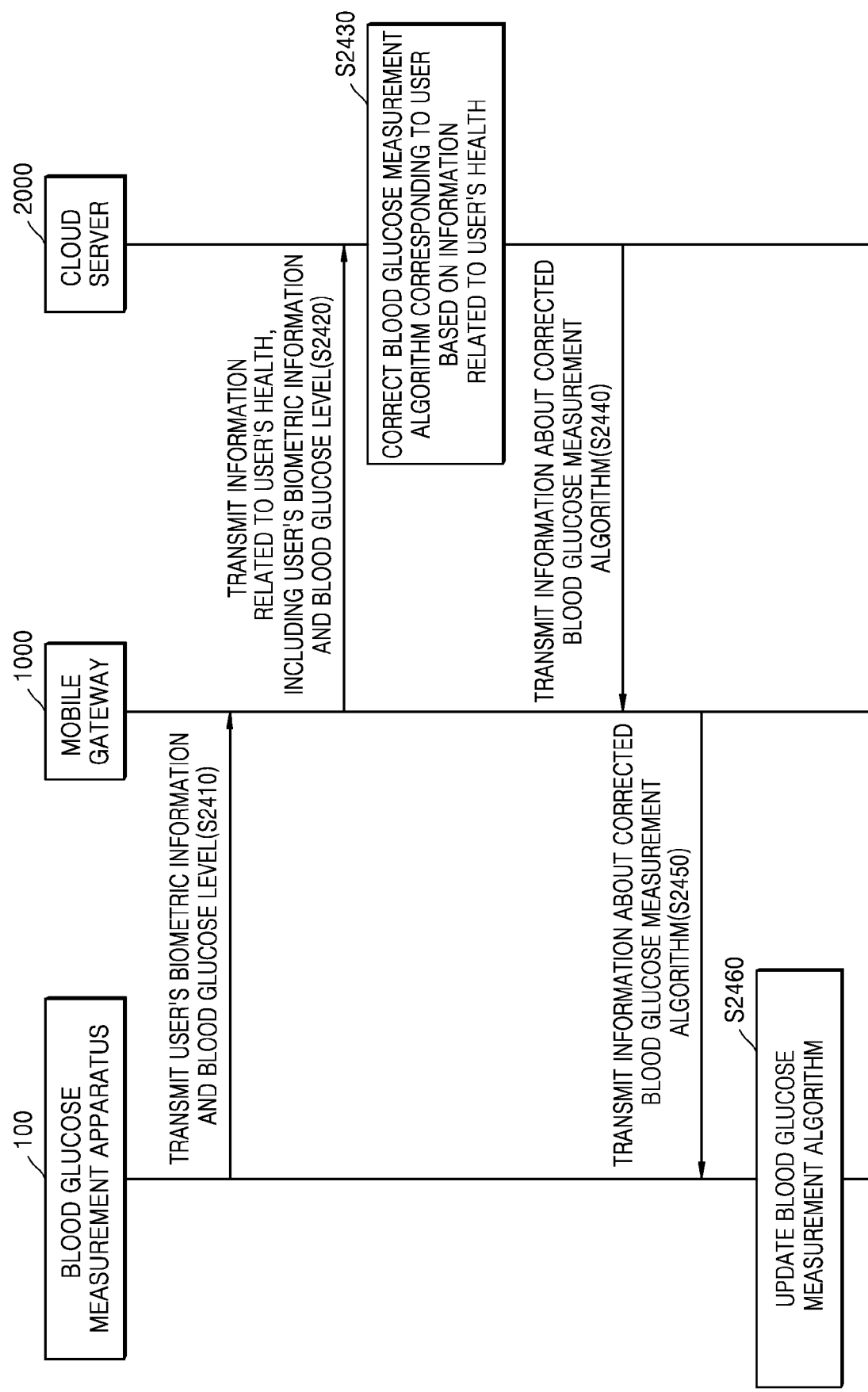
FIGS. 24A and 24B are respectively a flowchart and a diagram for describing a method by which a blood glucose measurement apparatus receives a blood glucose measurement algorithm from a cloud server, according to an exemplary embodiment.
Figure 24B:
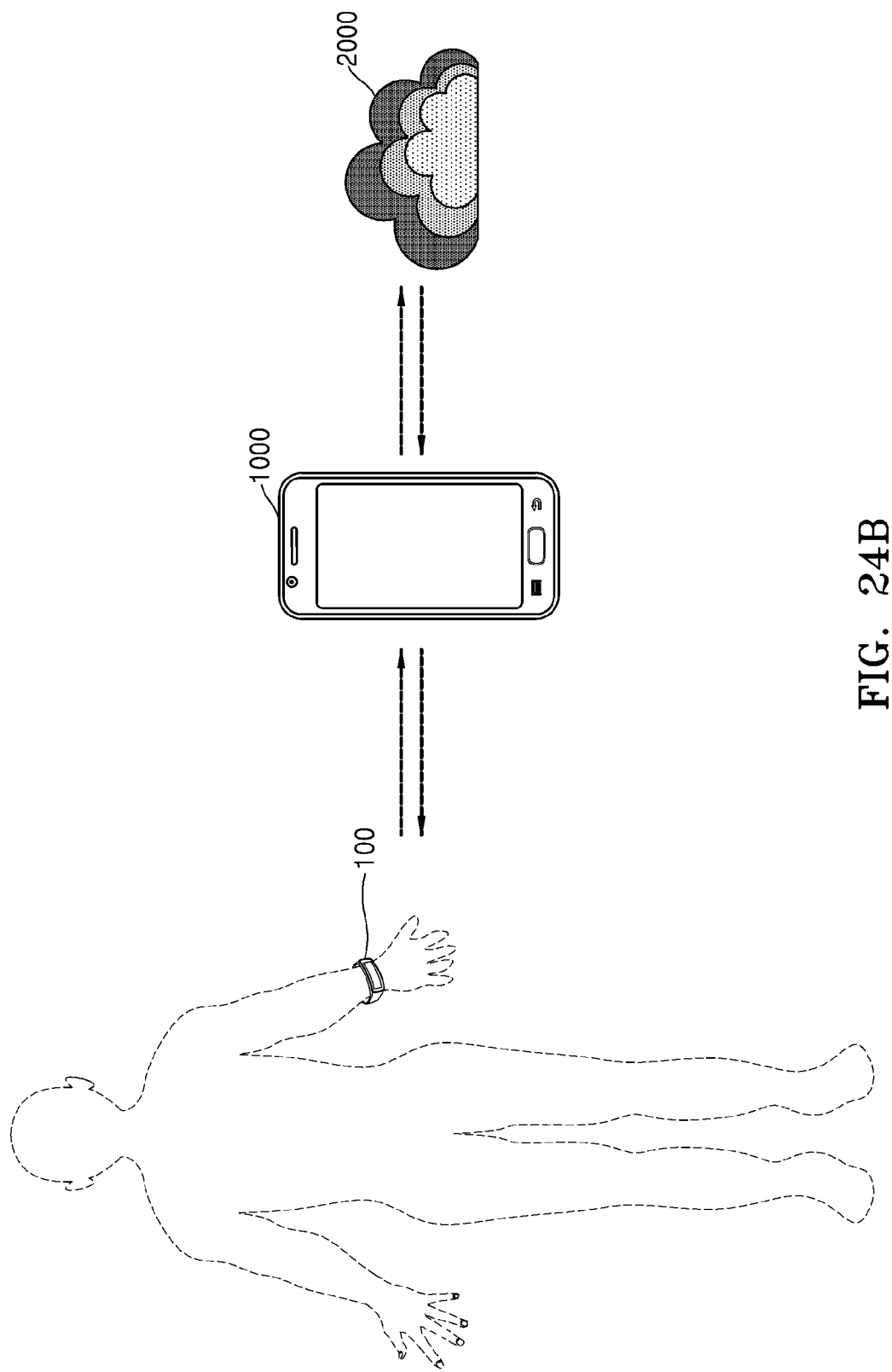

FIGS. 24A and 24B are respectively a flowchart and a diagram for describing a method by which a blood glucose measurement apparatus 100 receives a blood glucose measurement algorithm from a cloud server 2000, according to an exemplary embodiment.

In FIG. 24B, the blood glucose measurement apparatus 100 may include a noninvasive blood glucose measurement apparatus using an optical measurement method, an electrochemical measurement method, and a method using expiration gas, and an invasive blood glucose measurement apparatus 100 configured to collect a blood sample from a body and measure a concentration of glucose in the blood sample.

A mobile gateway 1000 may be one of user's mobile devices. The mobile gateway 1000 may receive a user's biometric information and a user's blood glucose level from the blood glucose measurement apparatus 100 and transmit the received biometric information and the received blood glucose level to the cloud server 2000.

The cloud server 2000 may store information related to a user's health and control a user's blood glucose measurement algorithm.

Referring to FIG. 24A, in operation S2410, the blood glucose measurement apparatus 100 may transmit the user's biometric information and the user's blood glucose level to the mobile gateway 1000.

The identification information of the mobile gateway 1000 may be stored in the blood glucose measurement apparatus 100. The blood glucose measurement apparatus 100 may transmit the user's biometric information and the user's blood glucose level to the mobile gateway 1000 by using a short-range wireless communication. The blood glucose measurement apparatus 100 may transmit the user's biometric information and the user's blood glucose level to the mobile gateway 1000 periodically or in response to a request from the mobile gateway 1000.

The biometric information may be data received from the sensor 200. In addition, the biometric information may be data measured by the blood glucose measurement apparatus 100. The biometric information may include information about the time when the biometric information was measured.

The user's blood glucose level may be a blood glucose level calculated by the blood glucose measurement apparatus 100. The user's blood glucose level may include information about the time when the blood glucose level was measured.

In operation S2420, the mobile gateway 1000 may transmit the information related to the user's health, including the user's biometric information and the user's blood glucose level, to the blood glucose measurement apparatus 100.

The mobile gateway 1000 may store a user's account information registered in the cloud server 2000. The mobile gateway 1000 may transmit the information related to the user's health to the cloud server 2000, based on the user's account information.

In addition, the information related to the user's health may include a user's medical records, an amount of a user's diet, a dietary ingredient, sleeping hours, motion quantity, and life habit, as well as the biometric information and the blood glucose level.

In operation S2430, the cloud server 2000 may correct the blood glucose measurement algorithm corresponding to the user, based on the information related to the user's health which is received from the mobile gateway 1000.

The cloud server 2000 may store the blood glucose measurement algorithm corresponding to the user. The cloud server 2000 may acquire the blood glucose measurement algorithm corresponding to the user's account information received from the mobile gateway 1000 and correct the acquired blood glucose measurement algorithm.

For example, the cloud server 2000 may compare the user's blood glucose level measured by the invasive method with the user's blood glucose level measured by the noninvasive method within a reference time and correct the blood glucose measurement algorithm by the noninvasive method. For example, the cloud server 2000 may correct the blood glucose measurement algorithm by the noninvasive method so that the user's blood glucose level measured by the noninvasive method exhibits the user's blood glucose level measured by the invasive method within the reference time.

The correction of the blood glucose measurement algorithm by the noninvasive method may include a correction of a coefficient determining a correlation between the biometric information and the status of the autonomic nervous system, and a correction of coefficients indicating a correlation between the status of the autonomic nervous system and a secreted amount of body fluid, a correlation between the secreted amount of the body fluid and the blood glucose level, a correlation between the biometric information and the motion quantity, or a correlation between the motion quantity and the blood glucose level.

In addition, the cloud server 2000 may correct the blood glucose measurement algorithm based on the user's medical records, the amount of the user's diet, the dietary ingredient, the sleeping hours, the motion quantity, and the life habit, as well as the biometric information and the blood glucose level.

For example, when the user rapidly gains weight, the cloud server 2000 may increase a coefficient indicating a secreted amount of sweat according to an activation of a sympathetic nerve.

In addition, for example, the cloud server 2000 may change a normal reference range of the blood glucose level according to the level, based on a pattern of the user's sleeping hours and mealtime. For example, the normal reference range of the blood glucose level immediately after the user gets up may be determined as about 80 mg/dL to about 100 mg/dL, which is a general fasting blood glucose level, the normal reference range of the blood glucose level 2 hours after a meal may be determined as about 80 mg/dL to about 140 mg/dL, and the normal reference range of the blood glucose level 3 hours after a meal may be determined as about 80 mg/dL to about 100 mg/dL In operation S2440, the cloud server 2000 may transmit information about the corrected blood glucose measurement algorithm to the mobile gateway 1000.

The information about the corrected blood glucose measurement algorithm may include information about a coefficient determining a correlation between the biometric information and the status of the autonomic nervous system, and information about coefficients indicating a correlation between the status of the autonomic nervous system and a secreted amount of body fluid, a correlation between the secreted amount of the body fluid and the blood glucose level, a correlation between the biometric information and the motion quantity, or a correlation between the motion quantity and the blood glucose level.

In operation S2450, the mobile gateway 1000 may transmit the information about the corrected blood glucose measurement algorithm to the blood glucose measurement apparatus 100.

In operation S2460, the blood glucose measurement apparatus 100 may update the blood glucose measurement algorithm.

For example, the blood glucose measurement apparatus 100 may update the blood glucose measurement algorithm by changing setting values of a blood glucose measurement program stored in the blood glucose measurement apparatus 100. For example, the blood glucose measurement apparatus 100 may change the coefficient determining the correlation between the biometric information and the status of the autonomic nervous system, and the coefficients indicating the correlation between the status of the autonomic nervous system and the secreted amount of the body fluid, the correlation between the secreted amount of the body fluid and the blood glucose level, the correlation between the biometric information and the motion quantity, or the correlation between the motion quantity and the blood glucose level. In addition, for example, the blood glucose measurement apparatus 100 may adjust the users' normal blood glucose range.

Figure 25:
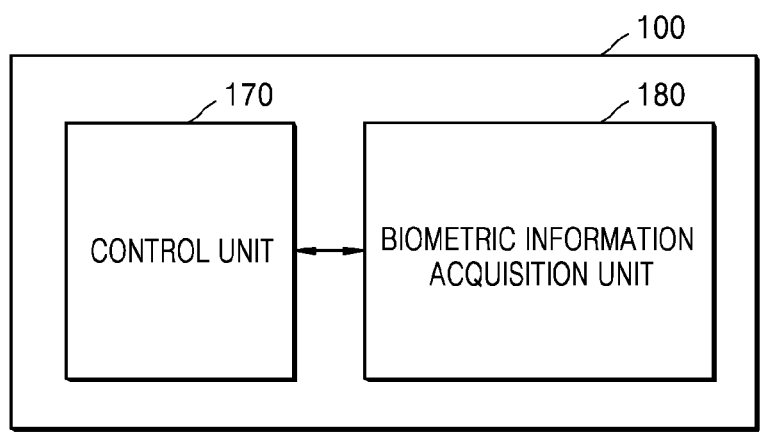
FIG. 25 is a block diagram of a blood glucose measurement apparatus according to an exemplary embodiment.

FIG. 25 is a block diagram of a blood glucose measurement apparatus 100 according to an exemplary embodiment.

Referring to FIG. 25, the blood glucose measurement apparatus 100 may include a control unit 170 and a biometric information acquisition unit 180.

The control unit 170 may determine a user's blood glucose level based on a concentration of glucose in body fluid secreted from a user.

In addition, the control unit 170 may correct the determined blood glucose level based on biometric information indicating a status of a user's autonomic nervous system.

In addition, the control unit 170 may determine the status of the autonomic nervous system based on the biometric information, determine a secretion velocity of the body fluid based on the determined status of the autonomic nervous system, and correct the determined blood glucose level based on the determined secretion velocity of the body fluid.

The biometric information acquisition unit 180 may acquire the biometric information indicating the status of the user's autonomic nervous system.

In addition, the biometric information acquisition unit 180 may include a communication unit configured to receive the biometric information indicating the status of the user's autonomic nervous system from a sensor attached to the user.

Figure 26A:
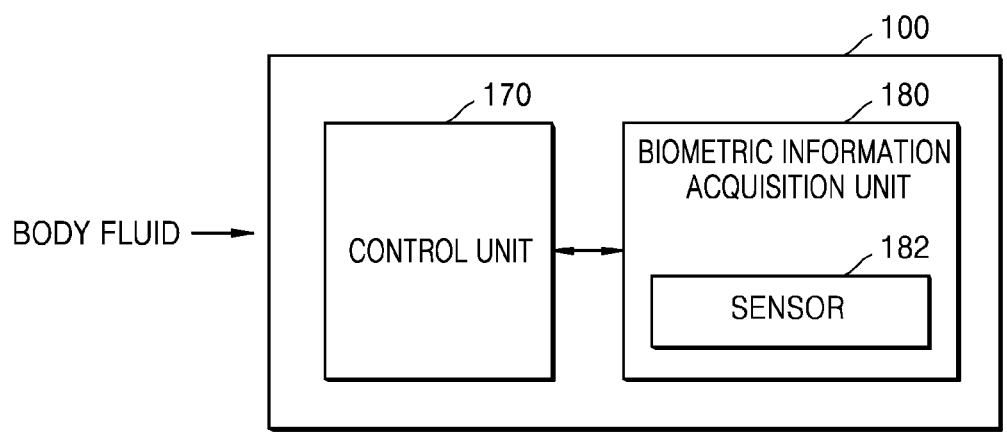
FIGS. 26A and 26B are block diagrams of a blood glucose measurement apparatus according to another exemplary embodiment.
Figure 26B:
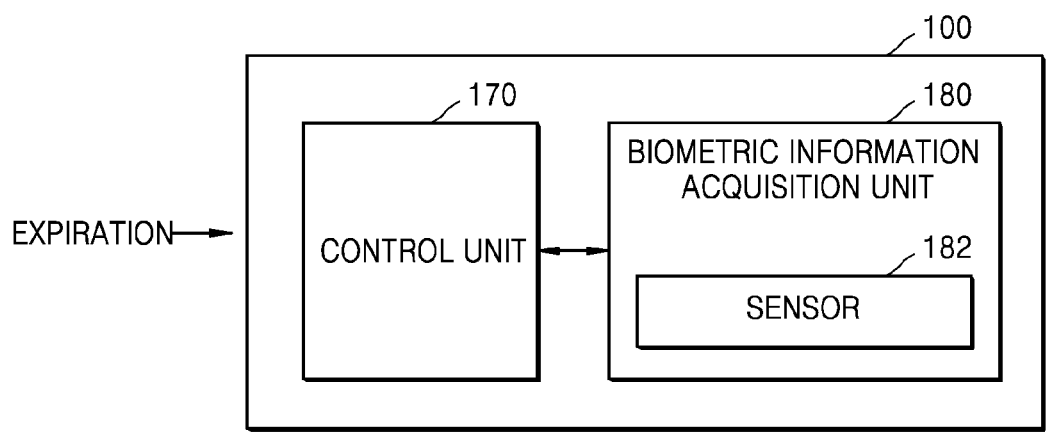

FIGS. 26A and 26B are block diagrams of a blood glucose measurement apparatus 100 according to another exemplary embodiment.

Referring to FIG. 26A, the blood glucose measurement apparatus 100 may collect body fluid secreted from a user. For example, the blood glucose measurement apparatus 100 may include a body fluid collection member. The body fluid collection member may mean a member configured to collect the body fluid secreted from the user. A control unit 170 may measure a concentration of glucose collected by the body fluid collection member and determine a user's blood glucose level based on the measured concentration of glucose in the body fluid.

Referring to FIG. 26B, the blood glucose measurement apparatus 100 may collect expiration discharged from the user. For example, the blood glucose measurement apparatus 100 may further include an expiration collection member. The expiration collection member may mean a member configured to collect the expiration discharged from the user. The control unit 170 may measure a concentration of biomarker gas collected by the expiration collection member and determine the user's blood glucose level based on the measured concentration of the biomarker gas.

In addition, the biometric information acquisition unit 180 may include a sensor 182. The sensor 182 may acquire a user's biometric data by measuring a user's biometric signal from the user. Examples of the sensor 182 may include glasses with a built-in camera 200a, an ECG sensor 200b, a GSR sensor 200c, a PPG sensor 200d, a thermometer 200e, a pedometer 200f and a GPS 200g.

The control unit 170 may determine the status of the user's autonomic nervous system based on the user's biometric data acquired by the sensor 182. The control unit 170 may correct the measured blood glucose level based on the determined status of the user's autonomic nervous system.

In addition, the control unit 170 may determine a user's motion quantity based on the user's biometric data acquired by the sensor 182. The control unit 170 may correct the measured blood glucose level based on the user's determined motion quantity.

Figure 27:
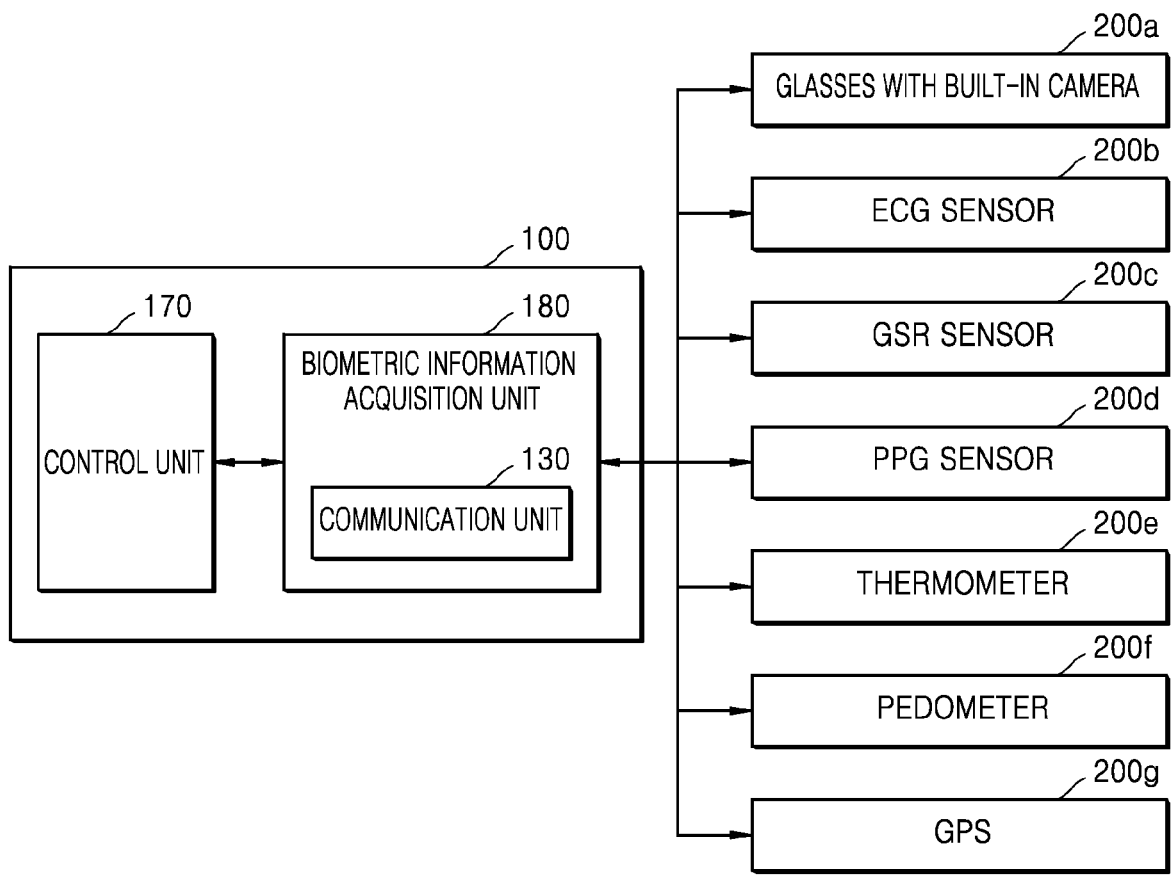
FIG. 27 is a block diagram of a blood glucose measurement apparatus according to another exemplary embodiment.

FIG. 27 is a block diagram of a blood glucose measurement apparatus 100 according to another exemplary embodiment.

Referring to FIG. 27, a biometric information acquisition unit 180 may further include a communication unit 130.

The communication unit 130 may perform short-range wireless communication with an external sensor.

The communication unit 130 may receive biometric information indicating a status of a user's autonomic nervous system from the sensor attached to the user.

The sensor may include glasses 200a with a built-in camera, an ECG sensor 200b, a GSR sensor 200c, a PPG sensor 200d, a thermometer 200e, a pedometer 200f, and a GPS 200g.

The control unit 170 may determine the status of the user's autonomic nervous system based on the user's biometric data acquired by the communication unit 130. The control unit 170 may correct the measured blood glucose level based on the determined status of the users' autonomic nervous system.

In addition, the control unit 170 may determine a user's motion quantity based on the user's biometric data acquired by the communication unit 130. The control unit 170 may correct the measured blood glucose level based on the user's determined motion quantity.

Figure 28:
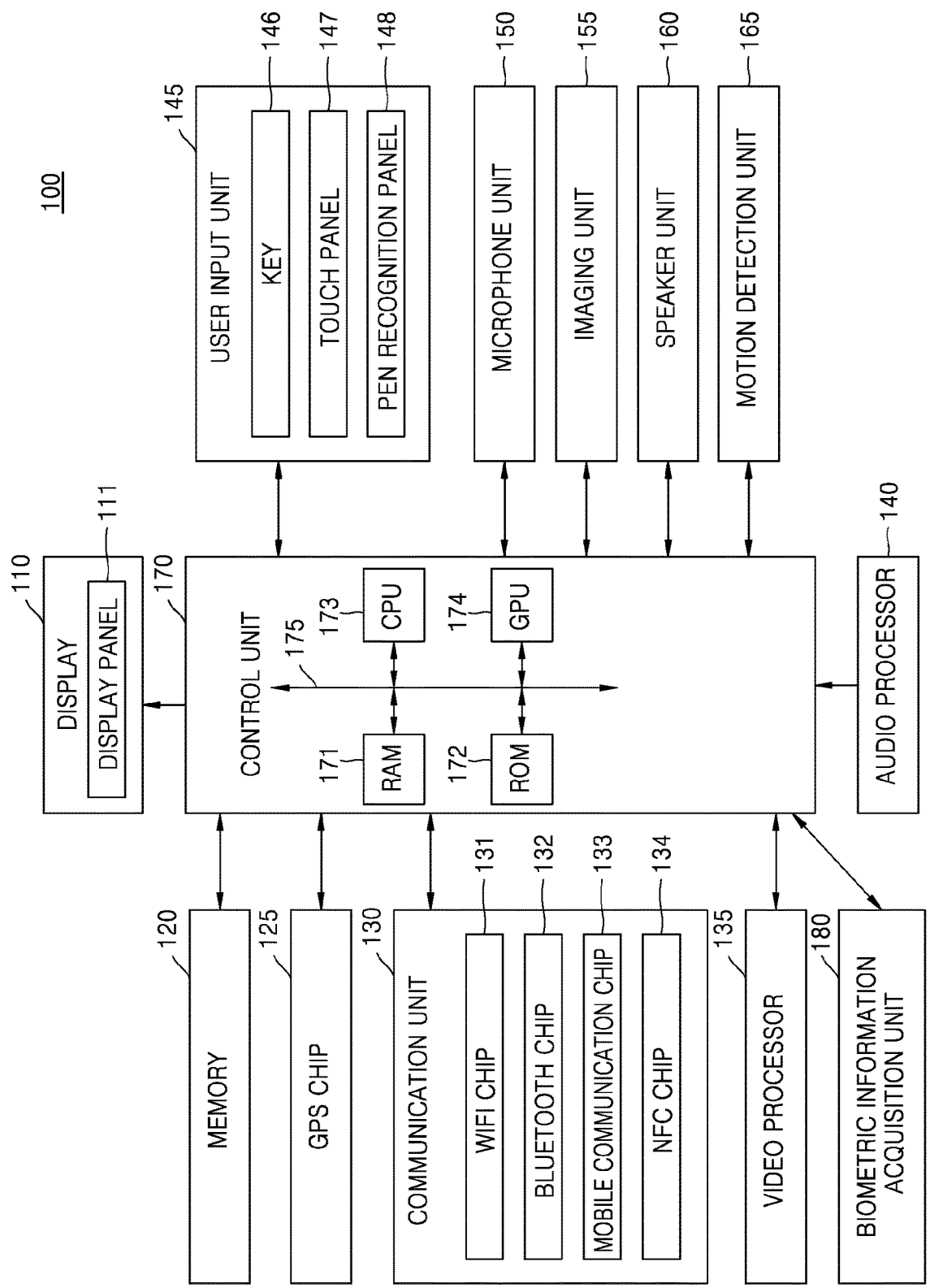
FIG. 28 is a block diagram of a blood glucose measurement apparatus according to another exemplary embodiment.

FIG. 28 is a block diagram of a blood glucose measurement apparatus 100 according to another exemplary embodiment.

Referring to FIG. 28, the blood glucose measurement apparatus 100 may includes a control unit 170, a biometric information acquisition unit 180, and at least one of a display unit 110, a memory 120, a GPS chip 125, a communication unit 130, a video processor 135, an audio processor 140, a user input unit 145, a microphone unit 150, an imaging unit 155, a speaker unit 160, and a motion detection unit 165.

The display unit 110 may include a display panel 111 and a display panel controller (not illustrated). The display panel 111 may be implemented by various types of displays, such as a liquid crystal display (LCD), an organic light emitting diode (OLED) display, an active-matrix organic light-emitting diode (AM-OLED), or a plasma display panel (PDP). The display panel 111 may be implemented to be flexible, transparent, or wearable. The display unit 110 may be integrated with a touch panel 147 of the user input unit 145 and provided as a touch screen (not illustrated). For example, the touch screen (not illustrated) may include an integrated module in which the display panel 111 and the touch panel 147 are integrated in a stacked structure.

The memory 120 may include at least one of an internal memory (not illustrated) or an external memory (not illustrated).

The internal memory may include at least one of a volatile memory (e.g., dynamic random access memory (DRAM), static RAM (SRAM), synchronous DRAM (SDRAM), etc.), a non-volatile memory (e.g., one time programmable read-only memory (OTPROM), programmable ROM (PROM), erasable and programmable ROM (EPROM, etc.), electrically erasable and programmable ROM (EEPROM), mask ROM, flash ROM, flash memory, etc.), hard disk drive (HDD), and solid state drive (SSD). According to an exemplary embodiment, the control unit 170 may load a command or data received from at least one of the non-volatile memory or other elements, and process the loaded command or data. In addition, the control unit 170 may store data, which is received from or generated by other elements, in the non-volatile memory.

The external memory may include at least one of compact flash (CF), secure digital (SD), micro secure digital (micro-SD), mini secure digital (mini-SD), extreme digital (xD), and memory stick.

The memory 120 may store various programs and data used for the operations of the blood glucose measurement apparatus 100. For example, the memory 120 may temporarily or semipermanently store at least a part of content to be displayed on a lock screen.

The control unit 170 may control the display unit 110 such that a part of the content stored in the memory 120 is displayed on the display unit 110. In other words, the control unit 170 may display a part of the content stored in the memory 120 on the display unit 110. Alternatively, when a user gestures in a predetermined region of the display unit 110, the control unit 170 may perform a control operation corresponding to the user's gesture.

The control unit 170 may include at least one of a RAM 171, a ROM 172, a CPU 173, a graphic processing unit (GPU) 174, and a bus 175. The RAM 171, the ROM 172, the CPU 173, and the GPU 174 are connected together through the bus 175.

The CPU 173 may access the memory 120 and perform booting by using an operating system (OS) stored in the memory 120. The CPU 173 may perform various operations by using various programs, data, content, and data stored in the memory 120.

The ROM 172 may store a set of commands for system booting. For example, in the blood glucose measurement apparatus 100, when a turn-on command is input and power is supplied, the CPU 173 may copy the OS stored in the memory 120 to the RAM 171 in response to the command stored in the ROM 172, execute the OS, and boot the system. When the booting of the blood glucose measurement apparatus 100 is completed, the CPU 173 may copy various programs stored in the memory 120 to the RAM 171, and execute various operations by executing the programs copied to the RAM 171. When the booting of the blood glucose measurement apparatus 100 is completed, the GPU 174 may display a user interface (UI) screen on the display unit 110. Specifically, the GPU 174 may generate a screen on which an electronic document, including various objects such as content, icons, or menus, is displayed. The GPU 174 may calculate attribute values, such as coordinate values, shapes, sizes, and colors of the objects, according to a layout of the screen. Specifically, the GPU 174 may generate a screen on which an electronic document, including various objects such as content, icons, or menus, is displayed. The screen generated by the GPU 174 may be provided to the display unit 110 and be displayed in each region of the display unit 110.

The GPS chip 125 may receive a GPS signal from a GPS satellite and calculate a current position of the blood glucose measurement apparatus 100. When a navigation program is used or when a current position of the user is needed, the control unit 170 may calculate the position of the user by using the GPS chip 125.

The communication unit 130 may communicate with various types of external devices according to various communication methods. The communication unit 130 may include at least one of a Wi-Fi chip 131, a Bluetooth chip 132, a wireless communication chip 133, and an NFC chip 134. The control unit 170 may communicate with various external devices by using the communication unit 130.

The Wi-Fi chip 131 and the Bluetooth chip 132 may perform communication by using a Wi-Fi scheme and a Bluetooth scheme, respectively. In the case of using the Wi-Fi chip 131 or the Bluetooth chip 132, it is possible to transmit and receive a variety of information after communication connection is made by first transmitting and receiving a variety of connection information such as SSID and session keys. The wireless communication chip 133 may mean a chip configured to perform communication in accordance with various communication protocols such as IEEE, ZigBee, a 3rd generation (3G) communication protocol, a 3rd Generation Partnership Project (3GPP) communication protocol, and a long term evolution (LTE) communication protocol. The NFC chip 134 may mean a chip configured to operate according to an NFC scheme using a frequency band of about 13.56 MHz among various RF-ID frequencies of about 135 kHz, about 13.56 MHz, about 433 MHz, about 860 MHz to about 960 MHz, and about 2.45 GHz.

The video processor 135 may process video data included in the content received through the communication unit 130 or the content stored in the memory 120. The video processor 135 may perform image processing, such as decoding, scaling, noise filtering, frame rate conversion, or resolution conversion, with respect to the video data.

The audio processor 140 may process audio data included in the content received through the communication unit 130 or the content stored in the memory 120. The audio processor 140 may perform audio processing, such as decoding, amplification, or noise filtering, with respect to the audio data.

When a multimedia content reproduction program is executed, the control unit 170 may reproduce corresponding content by driving the video processor 135 and the audio processor 140. The speaker unit 160 may output audio data generated by the audio processor 140.

The user input unit 145 may receive various commands from the user. The user input unit 145 may include at least one of a touch panel 147 and a pen recognition panel 148.

A key 146 may includes various types of keys, such as mechanical buttons or a wheel, in various regions, including a front surface, a side surface, or a rear surface of an outer body of the blood glucose measurement apparatus 100.

The touch panel 147 may detect a user's touch input and output an touch event value corresponding to the detected touch signal. In a case where the touch panel 147 is integrated with the display panel 111 to configure a touch screen (not illustrated), the touch screen may be implemented by various types of touch sensors, such as a capacitive touch sensor, a resistive touch sensor, and a piezoelectric touch sensor. The capacitive touch sensor may be configured to calculate touch coordinates by using a dielectric coated on a surface of the touch screen to detect fine electricity induced in a user's body when a user's body part comes into contact with the touch screen. The resistive touch sensor may include upper and lower electrode plates in the touch screen and be configured to calculate touch coordinates by detecting a current flowing when the upper and lower plates contact each other at a touched position when the user touches the touch screen. The touch event occurring in the touch screen may be frequently generated by a user's finger, but may be generated by any object made of a conductive material capable of causing a capacitance change.

The pen recognition panel 148 may sense a pen hovering or a pen touch input according to a user's action of operating a touch pen (e.g., a stylus pen, a digitizer pen, etc.), and output a sensed pen hovering event or a sensed pen touch event. The pen recognition panel 148 may be implemented by an EMR scheme and sense a touch or hovering input according to a change in the intensity of an electric field due to the pen hovering or touch. Specifically, the pen recognition panel 148 may include an electromagnetic induction coil sensor (not illustrated) having a grid structure, and an electronic signal processor (not illustrated) configured to sequentially providing an AC signal having a predetermined frequency to each loop coil of the electromagnetic induction coil. When a pen with a built-in resonance circuit is present near the loop coil of the pen recognition panel 148, a magnetic field transmitted from the corresponding loop coil may generate a current based on mutual electromagnetic induction in the resonance circuit inside the pen. Based on the generated current, an induction magnetic field may be generated from a coil constituting the resonance circuit inside the pen, and the pen recognition panel 148 may detect the induction magnetic field in the loop coil that is in a signal receivable state, and detect a hovering position or a touch position of the pen. The pen recognition panel 148 may be provided with an area capable of covering a predetermined lower portion of the display panel 111, for example, a display region of the display panel 111.

The microphone unit 150 may receive a user's voice or other sound and convert the received voice or sound into audio data. The control unit 170 may use the user's voice input through the microphone unit 150 during a call operation, or may convert the user's voice into audio data and store the audio data in the memory 120.

The imaging unit 155 may capture a still image or a moving image under the control of the user. The imaging unit 155 may include a plurality of imaging units, such as a front camera and a rear camera.

In a case where the imaging unit 155 and the microphone unit 150 are provided, the control unit 170 may perform control operations according to a user's voice input through the microphone unit 150 or a user's motion recognized by the imaging unit 155. For example, the blood glucose measurement apparatus 100 may operate in a motion control mode or a voice control mode. When the blood glucose measurement apparatus 100 operates in the motion control mode, the control unit 170 may activate the imaging unit 155 to capture an image of the user, track a change in a motion of the user, and perform a corresponding control operation. When the blood glucose measurement apparatus 100 operates in the voice control mode, the control unit 170 may analyze the user's voice input through the microphone unit 150 and operate in a voice recognition mode to execute a control operation according to the user's analyzed voice.

The motion detection unit 165 may detect a motion of the body of the blood glucose measurement apparatus 100. The blood glucose measurement apparatus 100 may be rotated or inclined in various directions. At this time, the motion detection unit 165 may detect motion characteristics, such as a rotating direction, a rotating angle, and a slope, by using at least one of various sensors, such as a terrestrial magnetism sensor, a gyro sensor, and an acceleration sensor.

Although not illustrated in FIG. 28, the blood glucose measurement apparatus 100 may further include a universal serial bus (USB) port to which a USB connector is connectable, various external input ports for connection with various external terminals (e.g., a headset, a mouse, a local area network (LAN), etc.), a digital multimedia broadcasting (DMB) chip configured to receive and process a DMB signal, and various sensors.

The names of the above-described elements of the blood glucose measurement apparatus 100 may be changed. In addition, the blood glucose measurement apparatus 100 according to the present exemplary embodiment may be configured to include at least one of the above-described elements, some elements may be omitted, or additional components may be further included.

Exemplary embodiments may be embodied in a storage medium including instruction codes executable by a computer, such as a program module executed by the computer. A computer-readable medium may be any available medium which is accessible by the computer and may include any volatile/non-volatile media and any removable/non-removable media. Furthermore, the computer-readable medium may include any computer storage and communication media. The computer storage medium may include any volatile/non-volatile and removable/non-removable media embodied by a certain method or technology for storing information such as computer-readable instruction code, a data structure, a program module or other data. The communication media may include computer-readable instruction code, a data structure, a program module, other data of modulated data signals such as a carrier wave, or other transmission mechanisms, and may include any information transmission media.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. For example, each element described as a singular form may be implemented in a distributed manner, and elements described as distributed may be implemented in an integrated manner.

While one or more exemplary embodiments have been described with reference to the figures, it will be understood by those of ordinary skill in the art that various changes in form and details may be made therein without departing from the spirit and scope as defined by the following claims.

What is claimed is:

1. A blood glucose measurement apparatus comprising:
   a processor configured to:
   determine a user's blood glucose level in a non-invasive manner based on a concentration of body fluid secreted from the user, without needing a blood sample from the user,
   correct the determined user's blood glucose level based on biometric information obtained from the user indicating a status of the user's autonomic nervous system,
   wherein the biometric information indicating the status of the autonomic nervous system includes at least one of a user's heart rate, a user's galvanic skin response, a contraction degree of a user's blood vessel, a size of a user's pupil, an amount of a user's tear, an amount of a user's saliva, and a user's body temperature, and
   wherein the body fluid includes at least one of a user's sweat, tear, saliva, and urine.

2. The blood glucose measurement apparatus of claim 1, wherein the processor is configured to determine the status of the autonomic nervous system based on the biometric information, determine a secretion velocity of the body fluid based on the determined status of the autonomic nervous system, and correct the determined user's blood glucose level based on the determined secretion velocity of the body fluid.

3. The blood glucose measurement apparatus of claim 1, wherein the status of the autonomic nervous system includes an activity degree of at least one of a user's sympathetic nerve and parasympathetic nerve.

4. The blood glucose measurement apparatus of claim 1, comprising a communication unit comprising a WiFi chip, NFC chip, Bluetooth chip, and/or wireless communication chip, configured to receive the biometric information indicating the status of the user's autonomic nervous system from a sensor attached to the user.

5. The blood glucose measurement apparatus comprising: of claim 4,
   wherein the processor is further configured to determine a user's blood glucose level based on a concentration of biomarker gas in an expiration of the user,
   wherein the communication unit is further configured to receive biometric information indicating a motion quantity of the user,
   wherein the processor is further configured to correct the determined user's blood glucose level based on the biometric information indicating the user's motion quantity.

6. The blood glucose measurement apparatus of claim 5, wherein the biomarker gas is a gas that is discharged through the user's expiration when a user's body fat is decomposed.

7. The blood glucose measurement apparatus of claim 5, wherein the biometric information indicating the user's motion quantity comprises at least one of a user's step count, a user's moving speed, a user's heart rate, a users' skin hydration, and a user's body temperature.

8. The blood glucose measurement apparatus of claim 5, wherein the processor is configured to determine a user's motion quantity per unit time based on the biometric information and correct the determined user's blood glucose level based on the determined motion quantity per unit time.

9. A blood glucose measurement method comprising:
determining a user's blood glucose level in a non-invasive manner based on a concentration of body fluid secreted from the user, without needing a blood sample from the user;
acquiring biometric information indicating a status of the user's autonomic nervous system; and
correcting the determined user's blood glucose level based on the biometric information obtained from the user indicating a status of the user's autonomic nervous system, wherein the biometric information indicating the status of the autonomic nervous system includes at least one of a user's heart rate, a user's galvanic skin response, a contraction degree of a user's blood vessel, a size of a user's pupil, an amount of a user's tear, an amount of a user's saliva, and a user's body temperature,
wherein the body fluid includes at least one of a user's sweat, tear, saliva, and urine;
wherein the blood glucose measurement method further comprises: updating a blood glucose measurement algorithm using a corrected blood glucose measurement algorithm received from a server, wherein the corrected blood glucose measurement algorithm is corrected based on information related to the user's health.

10. The blood glucose measurement method of claim 9, wherein the correcting of the determined user's blood glucose level based on the biometric information comprises:
determining the status of the autonomic nervous system based on the biometric information;
determining a secretion velocity of the body fluid based on the determined status of the autonomic nervous system; and
correcting the determined user's blood glucose level based on the determined secretion velocity of the body fluid.

11. The blood glucose measurement method of claim 9, wherein the status of the autonomic nervous system includes an activity degree of at least one of a user's sympathetic nerve and parasympathetic nerve.

12. The blood glucose measurement method of claim 9, wherein the acquiring of the biometric information indicating the status of the user's autonomic nervous system comprises receiving the biometric information indicating the status of the user's autonomic nervous system from a sensor attached to the user.

13. The blood glucose measurement method of claim 9, further comprising:
determining the user's blood glucose level based on a concentration of biomarker gas in an expiration of the user;
acquiring biometric information indicating a motion quantity of the user; and
correcting the determined user's blood glucose level based on the biometric information.

14. The blood glucose measurement method of claim 13, wherein the biomarker gas is a gas that is discharged through the user's expiration when a user's body fat is decomposed.

15. The blood glucose measurement method of claim 13, wherein the biometric information indicating the user's motion quantity comprises at least one of a user's step count, a user's moving speed, a user's heart rate, a user's skin hydration, and a user's body temperature.

16. The blood glucose measurement method of claim 13, wherein the correcting of the determined user's blood glucose level based on the biometric information comprises:
determining the user's motion quantity per unit time based on the biometric information; and
correcting the determined blood glucose level based on the determined motion quantity per unit time.

\* \* \* \* \*